(12) United States Patent
Kawaue et al.

(10) Patent No.: US 8,252,505 B2
(45) Date of Patent: Aug. 28, 2012

(54) COMPOUND AND METHOD OF PRODUCING SAME, ACID GENERATOR, RESIST COMPOSITION, AND METHOD OF FORMING RESIST PATTERN

(75) Inventors: Akiya Kawaue, Kawasaki (JP); Keita Ishiduka, Kawasaki (JP); Kensuke Matsuzawa, Kawasaki (JP); Yoshiyuki Utsumi, Kawasaki (JP); Hiroaki Shimizu, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 725 days.

(21) Appl. No.: 12/371,876

(22) Filed: Feb. 16, 2009

(65) Prior Publication Data
US 2009/0208871 A1 Aug. 20, 2009

(30) Foreign Application Priority Data
Feb. 18, 2008 (JP) ................................ 2008-036732

(51) Int. Cl.
*G03F 7/004* (2006.01)
*C07D 493/08* (2006.01)
*C07D 495/08* (2006.01)

(52) U.S. Cl. ..................... 430/270.1; 430/910; 430/921; 430/922; 560/150; 562/100; 562/109; 562/113; 549/269; 549/300

(58) Field of Classification Search ............... 430/270.1, 430/910, 921, 922; 560/150; 562/100, 109, 562/113; 549/269, 300
See application file for complete search history.

(56) References Cited

U.S. PATENT DOCUMENTS

| 5,945,517 A | 8/1999 | Nitta et al. |
| 6,153,733 A | 11/2000 | Yukawa et al. |
| 7,323,287 B2 | 1/2008 | Iwai et al. |
| 7,741,007 B2 * | 6/2010 | Yamaguchi et al. ....... 430/270.1 |
| 7,927,780 B2 * | 4/2011 | Kawaue et al. ............ 430/270.1 |
| 8,012,669 B2 * | 9/2011 | Shimizu et al. ............ 430/270.1 |
| 2007/0078269 A1 * | 4/2007 | Harada et al. .................. 549/266 |
| 2008/0085469 A1 * | 4/2008 | Ohsawa et al. ............ 430/286.1 |
| 2010/0119974 A1 * | 5/2010 | Hada et al. ................. 430/281.1 |

FOREIGN PATENT DOCUMENTS

| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2003-241385 | 8/2003 |
| WO | WO 2004-074242 | 9/2004 |

* cited by examiner

*Primary Examiner* — John Chu
(74) *Attorney, Agent, or Firm* — Knobbe Martens Olson & Bear LLP

(57) ABSTRACT

A resist composition including a base component (A) that exhibits changed solubility in an alkali developing solution under the action of acid, and an acid generator component (B) that generates acid upon exposure, wherein the acid generator component (B) includes an acid generator (B1) consisting of a compound represented by general formula (b1-2) shown below:

[Chemical Formula 1]

$$A^+ Z^- \qquad (b1\text{-}2)$$

wherein $A^+$ represents an organic cation; and $Z^-$ represents an anionic cyclic group, wherein the cyclic group includes an ester linkage within the ring structure, two mutually different groups are bonded to the ring structure, one of these groups includes an ester linkage in which a carbon atom that constitutes part of the ester linkage is bonded directly to the ring structure, and the other group includes an anion moiety.

12 Claims, No Drawings

COMPOUND AND METHOD OF PRODUCING SAME, ACID GENERATOR, RESIST COMPOSITION, AND METHOD OF FORMING RESIST PATTERN

BACKGROUND OF THE INVENTION

1. Field of the Invention

The present invention relates to a novel compound that is useful as an acid generator for a resist composition, a compound that is useful as a precursor to the novel compound and a method of producing the same, an acid generator, a resist composition, and a method of forming a resist pattern.

Priority is claimed on Japanese Patent Application No. 2008-036732, filed Feb. 18, 2008, the content of which is incorporated herein by reference.

2. Description of Related Art

In lithography techniques, for example, a resist film composed of a resist material is formed on a substrate, and the resist film is subjected to selective exposure of radial rays such as light or an electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

It recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use exposure light source having a wavelength shorter than these excimer lasers, such as $F_2$ excimer lasers, electron beams, EUV (extreme ultraviolet radiation), and X rays.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits changed solubility in an alkali developing solution under the action of acid and an acid generator that generates acid upon exposure. For example, a chemically amplified positive resist contains, as a base resin, a resin that exhibits increased solubility in an alkali developing solution under the action of acid, and an acid generator. In the formation of a resist pattern, when acid is generated from the acid generator upon exposure, the exposed portions become soluble in an alkali developing solution.

Until recently, polyhydroxystyrene (PHS) or derivative resins thereof in which the hydroxyl groups are protected with acid-dissociable, dissolution-inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm. As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from a (meth)acrylate ester including an aliphatic polycyclic group-containing tertiary alkyl ester-type acid dissociable, dissolution inhibiting group, such as a structural unit derived from a 2-alkyl-2-adamantyl (meth) acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

As acid generators usable in a chemically amplified resist, various types have been proposed including, for example, onium salt-based acid generators such as iodonium salts and sulfonium salts.

[Patent Document 1] Japanese Unexamined Patent Application, First Publication No. 2003-241385

SUMMARY OF THE INVENTION

Currently, as the anion moiety for the aforementioned type of onium salt-based acid generators, a perfluoroalkylsulfonic acid ion is generally used. It is considered that the perfluoroalkyl chain within the anion moiety is preferably long, as diffusion of the acid after exposure can be suppressed. However, a perfluoroalkyl chain of 6 to 10 carbon atoms is difficult to decompose, and hence, in consideration of safety in handling in terms of bioaccumulation, a nonafluorobutanesulfonic acid ion or the like is used. Accordingly, there is a demand for a novel acid generator for a resist composition that exhibits a high degree of safety and yet enables the reproduction of patterns of very fine dimensions, and the development of a novel compound able to satisfy these demands has been keenly sought.

The present invention takes the above circumstances into consideration, with an object of providing a novel compound that is useful as an acid generator for a resist composition, a compound that is useful as a precursor to the aforementioned novel compound and a method of producing the same, an acid generator, a resist composition, and a method of forming a resist pattern.

In order to achieve the aforementioned object, the inventors of the present invention propose the following aspects.

Specifically, a first aspect of the present invention is a resist composition including a base component (A) that exhibits changed solubility in an alkali developing solution under the action of acid, and an acid generator component (B) that generates acid upon exposure, wherein the acid generator component (B) includes an acid generator (B1) consisting of a compound represented by general formula (b1-2) shown below.

[Chemical Formula 1]

$$A^+Z^-$$ (b1-2)

wherein $A^+$ represents an organic cation; and $Z^-$ represents an anionic cyclic group, wherein the cyclic group includes an ester linkage within the ring structure, two mutually different groups are bonded to the ring structure, one of these groups includes an ester linkage in which a carbon atom that constitutes part of the ester linkage is bonded directly to the ring structure, and the other group includes an anion moiety.

A second aspect of the present invention is a method of forming a resist pattern, including: forming a resist film on a substrate using the resist composition according to the first aspect, conducting exposure of the resist film, and alkali-developing the resist film to form a resist pattern.

A third aspect of the present invention is a compound represented by general formula (I) shown below.

[Chemical Formula 2]

$$W^+Z^- \quad (I)$$

wherein $W^+$ represents an alkali metal ion or an ion represented by general formula (w-1) shown below; and $Z^-$ represents an anionic cyclic group, wherein the cyclic group includes an ester linkage within the ring structure, two mutually different groups are bonded to the ring structure, one of these groups includes an ester linkage in which a carbon atom that constitutes part of the ester linkage is bonded directly to the ring structure, and the other group includes an anion moiety.

[Chemical Formula 3]

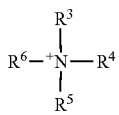

(w-1)

wherein $R^3$ to $R^6$ each independently represents a hydrogen atom or a hydrocarbon group that may have a substituent, at least one of $R^3$ to $R^6$ represents such a hydrocarbon group, and any two of $R^3$ to $R^6$ may be bonded together to form a ring in combination with the nitrogen atom in the formula.

A fourth aspect of the present invention is a method of producing a compound, including obtaining a compound represented by general formula (I-1) shown below by subjecting a compound represented by general formula (I-1-1) shown below and a compound represented by general formula (I-1-2) shown below to a dehydration/condensation.

[Chemical Formula 4]

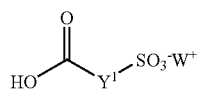

(I-1-1)

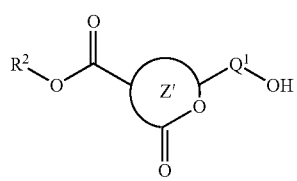

(I-1-2)

-continued

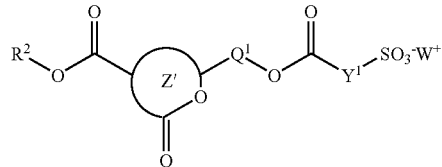

(I-1)

wherein $W^+$ represents an alkali metal ion or an ion represented by general formula (w-1) shown below, ring $Z'$ represents a cyclic group of 3 to 20 carbon atoms that may have a substituent, $R^2$ represents an alkyl group that may have a substituent, $Q^1$ represents an alkylene group of 1 to 12 carbon atoms or a single bond, and $Y^1$ represents an alkylene group or fluorinated alkylene group of 1 to 4 carbon atoms.

[Chemical Formula 5]

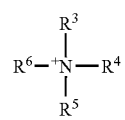

(w-1)

wherein $R^3$ to $R^6$ each independently represents a hydrogen atom or a hydrocarbon group that may have a substituent, at least one of $R^3$ to $R^6$ represents such a hydrocarbon group, and any two of $R^3$ to $R^6$ may be bonded together to form a ring in combination with the nitrogen atom in the formula.

Furthermore, a fifth aspect of the present invention is a compound represented by general formula (b1-2) shown below.

[Chemical Formula 6]

$$A^+Z^- \quad (b1-2)$$

wherein $A^+$ represents an organic cation; and $Z^-$ represents an anionic cyclic group, wherein the cyclic group includes an ester linkage within the ring structure, two mutually different groups are bonded to the ring structure, one of these groups includes an ester linkage in which a carbon atom that constitutes part of the ester linkage is bonded directly to the ring structure, and the other group includes an anion moiety.

Furthermore, a sixth aspect of the present invention is an acid generator consisting of a compound of the fifth aspect described above.

In the present description and claims, the term "structural unit" refers to a monomer unit that contributes to the formation of a resin component (polymer).

The term "exposure" is used as a general concept that includes irradiation with any form of radiation, including an ArF excimer laser, KrF excimer laser, $F_2$ excimer laser, as well as EUV (Extreme Ultra Violet), VUV (Vacuum Ultra Violet), EB (Electron Beam), X-ray or soft X-ray radiation.

The term "aliphatic cyclic group" refers to a monocyclic group or polycyclic group that has no aromaticity.

The term "alkyl group", unless otherwise specified, includes linear, branched or cyclic monovalent saturated hydrocarbon groups.

A "lower alkyl group" describes an alkyl group of 1 to 5 carbon atoms.

According to the present invention there are provided a novel compound that is useful as an acid generator for a resist composition, a compound that is useful as a precursor to the novel compound and a method of producing the same, an acid generator, a resist composition, and a method of forming a resist pattern.

DETAILED DESCRIPTION OF THE INVENTION

<<Compound (I)>>

A compound (I) of the present invention is represented by general formula (I) shown above.

In general formula (I), $W^+$ represents an alkali metal ion or an ion represented by general formula (w-1) shown above (hereafter frequently referred to as "ion (w-1)").

Examples of the alkali metal ion for $W^+$ include a sodium ion, lithium ion and potassium ion, and of these, a sodium ion or lithium ion is preferred.

In formula (w-1), $R^3$ to $R^6$ each independently represents a hydrogen atom or a hydrocarbon group that may have a substituent.

The hydrocarbon group for $R^3$ to $R^6$ may be either an aromatic hydrocarbon group or an aliphatic hydrocarbon group.

The aromatic hydrocarbon group for $R^3$ to $R^6$ is a hydrocarbon group having an aromatic ring, and the number of carbon atoms within the aromatic hydrocarbon group is preferably from 3 to 30, more preferably from 5 to 30, still more preferably from 5 to 20, still more preferably from 6 to 15, and most preferably from 6 to 12. This number of carbon atoms does not include any carbon atoms within the substituent.

Specific examples of the aromatic hydrocarbon group include aryl groups in which one hydrogen atom has been removed from an aromatic hydrocarbon ring such as a phenyl group, biphenyl group, fluorenyl group, naphthyl group, anthryl group or phenanthryl group, and arylalkyl groups such as a benzyl group, phenethyl group, 1-naphthylmethyl group, 2-naphthylmethyl group, 1-naphthylethyl group or 2-naphthylethyl group. The number of carbon atoms within the alkyl chain of the arylalkyl group is preferably from 1 to 4, more preferably from 1 to 2, and is most preferably 1.

The aromatic hydrocarbon group may have a substituent. For example, a carbon atom that constitutes part of the aromatic ring of the aromatic hydrocarbon group may be substituted with a hetero atom, and a hydrogen atom bonded to the aromatic ring of the aromatic hydrocarbon group may be substituted with a substituent.

Examples of the former case include heteroaryl groups in which a carbon atom that constitutes part of the aromatic ring of an aforementioned aryl group is substituted with a hetero atom such as an oxygen atom, sulfur atom or nitrogen atom, and heteroarylalkyl groups in which a carbon atom that constitutes part of the aromatic hydrocarbon ring within an aforementioned arylalkyl group is substituted with an aforementioned hetero atom.

Examples of the substituent within the aromatic hydrocarbon group in the latter case include an alkyl group, alkoxy group, halogen atom, halogenated alkyl group, hydroxyl group, oxygen atom (=O), nitrogen atom, cyano group (—CN), amino group (—NH$_2$), or amide group (—NH—C(=O)—).

As the alkyl group for the substituent within the aromatic hydrocarbon group, an alkyl group of 1 to 5 carbon atoms is preferred, and a methyl group, ethyl group, propyl group, n-butyl group or tert-butyl group is the most desirable.

As the alkoxy group for the substituent within the aromatic hydrocarbon group, an alkoxy group of 1 to 5 carbon atoms is preferred, a methoxy group, ethoxy group, n-propoxy group, iso-propoxy group, n-butoxy group or tert-butoxy group is more preferred, and a methoxy group or ethoxy group is the most desirable.

Examples of the halogen atom for the substituent within the aromatic hydrocarbon group include a fluorine atom, chlorine atom, bromine atom or iodine atom, and a fluorine atom is preferred.

Examples of the halogenated alkyl group for the substituent within the aromatic hydrocarbon group include groups in which some or all of the hydrogen atoms within an aforementioned alkyl group have been substituted with the aforementioned halogen atoms.

The aliphatic hydrocarbon group for $R^3$ to $R^6$ may be either a saturated aliphatic hydrocarbon group or an unsaturated aliphatic hydrocarbon group. Further, the aliphatic hydrocarbon group may be linear, branched or cyclic.

In the aliphatic hydrocarbon group for $R^3$ to $R^6$, a carbon atom that constitutes part of the aliphatic hydrocarbon group may be substituted with a substituent that includes a hetero atom, and some or all of the hydrogen atoms that constitute the aliphatic hydrocarbon group may be substituted with substituents that include a hetero atom.

As the "hetero atom" within $R^3$ to $R^6$, any atom other than a carbon atom or hydrogen atom may be used without any particular limitations, and examples include a halogen atom, oxygen atom, sulfur atom or nitrogen atom. Examples of the halogen atom include a fluorine atom, chlorine atom, iodine atom or bromine atom.

The substituent that includes a hetero atom may consist solely of the hetero atom, or may be a group that includes a group or atom other than the hetero atom.

Specific examples of the substituent that may substitute a carbon atom include —O—, —C(=O)—O—, —C(=O)—, —O—C(=O)—O—, —S—, —S(=O)$_2$—, —S(=O)$_2$—O—, or an amide group (—NH—C(=O)—). If the aliphatic hydrocarbon group is a cyclic group, then the substituent may be included within the ring structure.

Specific examples of the substituent that may substitute some or all of the hydrogen atoms include an alkoxy group, halogen atom, halogenated alkyl group, hydroxyl group, oxygen atom (=O), nitrogen atom, cyano group (—CN), amino group (—NH$_2$), or amide group (—NH—C(=O)—).

As the alkoxy group, an alkoxy group of 1 to 5 carbon atoms is preferred, a methoxy group, ethoxy group, n-propoxy group, iso-propoxy group, n-butoxy group or tert-butoxy group is more preferred, and a methoxy group or ethoxy group is the most desirable.

Examples of the halogen atom include a fluorine atom, chlorine atom, bromine atom or iodine atom, and a fluorine atom is preferred.

Examples of the halogenated alkyl group include groups in which some or all of the hydrogen atoms within an alkyl group of 1 to 5 carbon atoms such as a methyl group, ethyl group, propyl group, n-butyl group or tert-butyl group have been substituted with the aforementioned halogen atoms.

As the substituent that may substitute some or all of the hydrogen atoms, of the above, a hydroxyl group is particularly preferred.

As the aliphatic hydrocarbon group, a linear or branched saturated hydrocarbon group, a linear or branched monovalent unsaturated hydrocarbon group, or a cyclic aliphatic hydrocarbon group (an aliphatic cyclic group) is preferred.

The linear saturated hydrocarbon group (alkyl group) preferably contains 1 to 20 carbon atoms, more preferably 1 to 15 carbon atoms, and most preferably 1 to 12 carbon atoms. Specific examples include a methyl group, ethyl group, propyl group, butyl group, pentyl group, hexyl group, heptyl group, octyl group, nonyl group, decanyl group, undecyl group, dodecyl group, tridecyl group, isotridecyl group, tetradecyl group, pentadecyl group, hexadecyl group, isohexadecyl group, heptadecyl group, octadecyl group, nonadecyl group, eicosyl group, heneicosyl group, or docosyl group.

The branched saturated hydrocarbon group (alkyl group) preferably contains 3 to carbon atoms, more preferably 3 to 15 carbon atoms, and most preferably 3 to 10 carbon atoms. Specific examples include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group, or 4-methylpentyl group.

The unsaturated hydrocarbon group preferably contains 2 to 10 carbon atoms, more preferably 2 to 5 carbon atoms, still more preferably 2 to 4 carbon atoms, and most preferably 3 carbon atoms. Examples of the linear monovalent unsaturated hydrocarbon group include a vinyl group, propenyl group (allyl group) or butenyl group. Examples of the branched monovalent unsaturated hydrocarbon group include a 1-methylpropenyl group or 2-methylpropenyl group.

As the unsaturated hydrocarbon group, of the above, a propenyl group is particularly preferred.

The aliphatic cyclic group may be either a monocyclic group or a polycyclic group. The number of carbon atoms is preferably from 3 to 30, more preferably from 5 to 30, still more preferably from 5 to 20, still more preferably from 6 to 15, and is most preferably from 6 to 12. Cyclic alkyl groups are particularly desirable.

Examples include groups in which one or more hydrogen atoms have been removed from a monocycloalkane, and groups in which one or more hydrogen atoms have been removed from a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

In those cases where the aliphatic cyclic group does not include a substituent having a hetero atom within the ring structure, the aliphatic cyclic group is preferably a polycyclic group, is more preferably a group in which one or more hydrogen atoms have been removed from a polycycloalkane, and is most preferably a group in which one or more hydrogen atoms have been removed from adamantane.

In those cases where the aliphatic cyclic group includes a substituent having a hetero atom within the ring structure, the substituent having a hetero atom is preferably —O—, —C(=O)—O—, —S—, —S(=O)$_2$—, or —S(=O)$_2$—O—. Specific examples of this type of aliphatic cyclic group include the groups shown below in formulas (L1) to (L5) and (S1) to (S4).

[Chemical Formula 7]

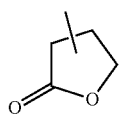
(L1)

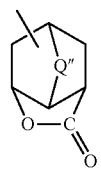
(L2)

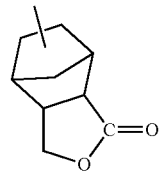
(L3)

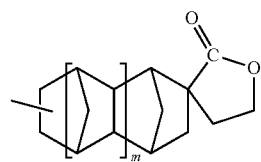
(L4)

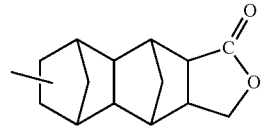
(L5)

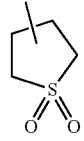
(S1)

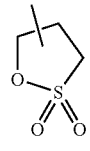
(S2)

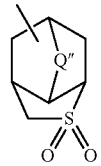
(S3)

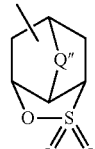
(S4)

wherein Q" represents an alkylene group of 1 to 5 carbon atoms, —O—, —S—, —O—R$^{94}$— or —S—R$^{95}$—, wherein R$^{94}$ and R$^{95}$ each independently represents an alkylene group of 1 to 5 carbon atoms, and m represents an integer of 0 or 1.

As the alkylene group for Q", a linear or branched alkylene group is preferred, and specific examples include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—$CH_2CH_2CH_2$—]; alkyltrimethylene groups such as —$CH(CH_3)CH_2CH_2$— and —$CH_2CH(CH_3)CH_2$—; a tetramethylene group [—$CH_2CH_2CH_2CH_2$—]; alkyltetramethylene groups such as —$CH(CH_3)CH_2CH_2CH_2$— and —$CH_2CH(CH_3)CH_2CH_2$—; and a pentamethylene group [—$CH_2CH_2CH_2CH_2CH_2$—]. The number of carbon atoms within the alkylene group is preferably from 1 to 4, and more preferably from 1 to 3.

Examples of the alkylene group for $R^{94}$ and $R^{95}$ include the same alkylene groups as those exemplified for Q".

Within these aliphatic cyclic groups, some of the hydrogen atoms bonded to the carbon atoms that constitute the ring structure may be substituted with substituents. Examples of these substituents include an alkyl group, alkoxy group, halogen atom, halogenated alkyl group, hydroxyl group, or oxygen atom (=O).

As the alkyl group, an alkyl group of 1 to 5 carbon atoms is preferred, and a methyl group, ethyl group, propyl group, n-butyl group or tert-butyl group is particularly desirable.

Examples of the alkoxy group or halogen atom include the same alkoxy groups or halogen atoms as those exemplified above for the substituent that substitutes some or all of the hydrogen atoms.

In the present invention, as $R^3$ to $R^6$, linear alkyl groups that may have a substituent and cyclic groups that may have a substituent are preferred. The cyclic group may be either an aromatic hydrocarbon group that may have a substituent, or an aliphatic cyclic group that may have a substituent, and is most preferably an aliphatic cyclic group that may have a substituent.

As the aromatic hydrocarbon group, a naphthyl group that may have a substituent or a phenyl group that may have a substituent is preferred.

As the aliphatic cyclic group that may have a substituent, a polycyclic aliphatic cyclic group that may have a substituent is preferred. As this polycyclic aliphatic cyclic group, the aforementioned groups in which one or more hydrogen atoms have been removed from a polycycloalkane, and the groups represented by formulas (L2) to (L5) and (S3) to (S4) above are preferred, and of these, an adamantyl group is particularly desirable.

Any two of $R^3$ to $R^6$ may be bonded together to form a ring in combination with the nitrogen atom in the formula. For example, two of $R^3$ to $R^6$ may be bonded together to form a single ring, three of $R^3$ to $R^6$ may be bonded together to form a single ring, or two different sets of $R^3$ to $R^6$ may be bonded together separately to form two rings.

The ring formed when any two of $R^3$ to $R^6$ are bonded together to form a ring in combination with the nitrogen atom in the formula (namely, a heterocycle including the nitrogen atom as a hetero atom) may be either an aliphatic heterocycle or an aromatic heterocycle. Further, the heterocycle may be either monocyclic or polycyclic.

Specific examples of the ion (w-1) include ammonium ions derived from an amine.

Here, the expression "ammonium ions derived from an amine" includes cations in which a hydrogen atom is bonded to the nitrogen atom of an amine, and quaternary ammonium ions in which an additional substituent is bonded to the nitrogen atom of an amine.

The amine that gives rise to the above ammonium ion may be either an aliphatic amine or an aromatic amine.

As the aliphatic amine, an amine in which at least one hydrogen atom of ammonia ($NH_3$) has been substituted with an alkyl group or hydroxyalkyl group of not more than 12 carbon atoms (namely, an alkylamine or alkyl alcohol amine), or a cyclic amine is preferred.

Specific examples of such alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably contains 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of the aromatic amine include aniline, pyridine, 4-dimethylaminopyridine (DMAP), pyrrole, indole, pyrazole, and imidazole.

Examples of the quaternary ammonium ion include a tetramethylammonium ion, tetraethylammonium ion and tetrabutylammonium ion.

In the ion (w-1), at least one of $R^3$ to $R^6$ represents a hydrocarbon group that may have a substituent, and two or three of $R^3$ to $R^6$ preferably represent hydrocarbon groups that may have a substituent. Moreover, ions in which at least one of $R^3$ to $R^6$ represents an alkyl group and at least one of $R^3$ to $R^6$ represents a hydrogen atom are particularly preferred.

Of these, ions in which three of $R^3$ to $R^6$ represent alkyl groups and the remaining one group represents a hydrogen atom (namely, trialkylammonium ions), or ions in which two of $R^3$ to $R^6$ represent alkyl groups and one of the remaining groups represents a hydrogen atom (namely, dialkylammonium ions) are preferred.

The alkyl groups within these trialkylammonium ions or dialkylammonium ions preferably each contains 1 to 10 carbon atoms, more preferably 1 to 8 carbon atoms, and most preferably 1 to 5 carbon atoms. Specific examples thereof include a methyl group, ethyl group, propyl group, butyl group, pentyl group, hexyl group, heptyl group, octyl group, nonyl group or decanyl group. Of these, an ethyl group is the most desirable.

In formula (I), $Z^-$ represents an anionic cyclic group.

The cyclic group includes an ester linkage within the ring structure, and also has two mutually different groups bonded to the ring structure. Of these two groups, one group includes an ester linkage in which the carbon atom that constitutes part of the ester linkage is bonded directly to the ring structure (hereafter frequently referred to as "the ester linkage-containing group"), and the other group includes an anion moiety (hereafter frequently referred to as "the anion moiety-containing group").

In the ester linkage-containing group, there are no particular limitations on the group bonded to the oxygen atom adjacent to the carbonyl group within the ester linkage, although a group that does not include an anion moiety is preferred, and a hydrocarbon group that may have a substituent is more preferable. Examples of the hydrocarbon group include aromatic hydrocarbon groups or aliphatic hydrocarbon groups that may have a substituent, and specific examples include the same groups as those exemplified for the hydrocarbon group for $R^3$ to $R^6$ in formula (w-1) above. Of these, an aliphatic hydrocarbon group that may have a substituent is preferred, an aliphatic hydrocarbon group that does not have a substituent is more preferred, and as the aliphatic hydrocarbon group, a saturated hydrocarbon group (alkyl group) is particularly desirable. This saturated hydrocarbon group (alkyl group) may be a linear, branched or cyclic group, but an alkyl group of 1 to 10 carbon atoms is preferred, and an alkyl group of 1 to 5 carbon atoms is more preferred. Specific examples thereof include a methyl group, ethyl group, n-propyl group, isopropyl group, n-butyl group, isobutyl group, n-pentyl group or cyclopentyl group, of these, an ethyl group or methyl group is particularly preferred, and a methyl group is the most desirable.

The number of ester linkage-containing groups in $Z^-$ is preferably either 1 or 2, and is most preferably 1.

The anion moiety-containing group preferably has an anionic group at the opposite end from the region where the group is bonded to the ring structure, and the anionic group is preferably a sulfonic acid group. Further, the anion moiety-containing group preferably includes an ester linkage, and the carbon atom that constitutes part of the ester linkage is preferably not bonded directly to the ring structure, so that the oxygen atom adjacent to the carbonyl group of the ester linkage is bonded to the ring structure, either directly (namely, via a single bond) or via a divalent linking group. Examples of this divalent linking group include linear, branched or cyclic alkylene groups, and examples thereof include the same alkylene groups as those exemplified above for Q" in the groups $R^3$ to $R^6$ within general formula (w-1). Further, in the alkylene group, some of the carbon atoms that constitute the group may be substituted with an oxygen atom, the number of such substituted carbon atoms is preferably not more than 2, and is most preferably 1. As the alkylene group bonded to the oxygen atom adjacent to the carbonyl group of the ester linkage, an alkylene group of 1 to 12 carbon atoms is preferred.

Furthermore, the anionic group is preferably bonded to the carbon atom that constitutes part of the ester linkage via a divalent linking group. Examples of this divalent linking group include linear, branched and cyclic alkylene groups, and specific examples include the same groups as those exemplified for the alkylene group bonded to the oxygen atom adjacent to the carbonyl group of the ester linkage. Some of the carbon atoms that constitute the alkylene group may be substituted with an oxygen atom, and some or all of the hydrogen atoms bonded to the carbon atoms may be substituted with halogen atoms. Examples of the halogen atoms include fluorine atoms, chlorine atoms, bromine atoms and iodine atoms, and of these, fluorine atoms are preferred.

The number of anion moiety-containing groups in $Z^-$ is preferably either 1 or 2, and is most preferably 1.

The aforementioned ring structure may be any ring structure that includes an ester linkage, and may be either a monocyclic group or a polycyclic group, but preferably contains no anion moieties.

There are no particular limitations on the number of ester linkages within the ring structure. For example, in those cases where the ring structure is a polycyclic group, an ester linkage may be included within each of the ring structures, within only one of the ring structures or within a plurality of ring structures, or a plurality of ester linkages may be included within a single ring structure. In those cases where the ring structure is a monocyclic group, the ring may include a plurality of ester linkages. Regardless of whether the ring structure is a monocyclic group or a polycyclic group, the number of ester linkages included within the ring structure is preferably either 1 or 2, and is most preferably 1.

The ring structure may also include other substituents besides the ester linkage-containing group and the anion moiety-containing group. Examples of these other substituents include alkyl groups of 1 to 5 carbon atoms, alkoxy groups of 1 to 5 carbon atoms, and hydroxyalkyl groups.

The number of these other substituents within the compound (I) is preferably from 0 to 2, is more preferably 0 or 1, and is most preferably 0. In the case of a plurality of substituents, the plurality of substituents may be either the same or different.

In the above ring structure, a portion of the carbon atoms of a cyclic hydrocarbon group are preferably substituted with the ester linkage (—C(=O)—O—). The cyclic hydrocarbon group may be either a cyclic aliphatic hydrocarbon group or an aromatic hydrocarbon group, but is preferably a cyclic aliphatic hydrocarbon group. Examples thereof include groups in which two or more hydrogen atoms have been removed from a monocycloalkane, and groups in which two or more hydrogen atoms have been removed from a polycycloalkane such as a bicycloalkane, tricycloalkane or tetracycloalkane. More specific examples include groups in which two or more hydrogen atoms have been removed from a monocycloalkane such as cyclopentane or cyclohexane, and groups in which two or more hydrogen atoms have been removed from a polycycloalkane such as adamantane, norbornane, isobornane, tricyclodecane or tetracyclododecane.

The ring structure may include a hetero atom besides the oxygen atoms that constitute the ester linkage within the structure, and examples of this other hetero atom include the same atoms as those exemplified above for the hetero atom in $R^3$ to $R^6$ within general formula (w-1).

Of the compounds represented by general formula (I) shown above, examples of preferred compounds include compounds represented by general formula (I-1) shown below (hereafter referred to as "compound (I-1)").

(I-1)

[Chemical Formula 8]

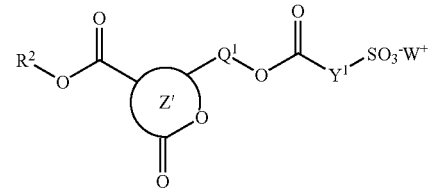

wherein $W^+$ is as defined above for $W^+$ in general formula (I), ring $Z'$ represents a cyclic group of 3 to 20 carbon atoms that may have a substituent and may include a hetero atom besides the oxygen atoms within the structure, $R^2$ represents an alkyl group that may have a substituent, $Q^1$ represents an alkylene group of 1 to 12 carbon atoms or a single bond, and $Y^1$ represents an alkylene group or fluorinated alkylene group of 1 to 4 carbon atoms.

In other words, the above ring structure is preferably the ring $Z'$, the ester linkage-containing group is preferably represented by general formula $R^2$—O—C(=O)—, and the anion moiety-containing group is preferably represented by general formula -$Q^1$—O—C(=O)—$Y^1$—$SO_3^-W^+$.

In formula (I-1), $W^+$ is as defined above for $W^+$ in general formula (I).

The ring Z' represents a cyclic group of 3 to 20 carbon atoms that includes an ester linkage and may also have a substituent, and examples include those ring structures described above that have a corresponding number of carbon atoms. The number of carbon atoms within the cyclic group exclusive of any carbon atoms within substituents is preferably from 5 to 20, and more preferably from 8 to 20.

The substituent which the cyclic group of 3 to 20 carbon atoms may have is a group besides the aforementioned ester linkage-containing group and anion moiety-containing group, and examples thereof include the same substituents that the aforementioned ring structure may have. Further, the number of these substituents is the same as the number of substituents that the aforementioned ring structure may have.

Furthermore, examples of preferred hetero atoms that may be included within the structure of the ring Z' include an oxygen atom and a sulfur atom.

The ring Z' is preferably a ring in which some of the carbon atoms of an aliphatic cyclic group have been substituted with an ester linkage. The aliphatic cyclic group is preferably a polycyclic group.

$R^2$ represents an alkyl group of 1 to 30 carbon atoms that may have a substituent.

The alkyl group of $R^2$ may be a linear, branched or cyclic group, and examples thereof include the same groups as those exemplified above for the linear, branched or cyclic alkyl group for $R^3$ to $R^6$ in general formula (w-1). Of these, a linear or branched alkyl group is preferred, a linear or branched alkyl group of 1 to 6 carbon atoms is more preferred, and specific examples thereof include a methyl group, ethyl group, propyl group, isopropyl group, n-butyl group, isobutyl group, tert-butyl group, pentyl group, isopentyl group, neopentyl group, or hexyl group. Of these, a methyl group or ethyl group is particularly preferred, and a methyl group is the most desirable.

Examples of the substituent that the alkyl group of $R^2$ may have include a hydroxyl group, cyano group, or halogen atom. Examples of the halogen atom include a fluorine atom, chlorine atom, iodine atom or bromine atom. There are no particular limitations on the number of hydrogen atoms of alkyl group substituted with these substituents, and all of the hydrogen atoms of the alkyl group may be substituted, but the number of substituents is preferably from 0 to 2, more preferably either 0 or 1, and is most preferably 0. In the case of a plurality of substituents, the plurality of substituents may be either the same or different.

Further, in the alkyl group of $R^2$, a carbon atom other than the carbon atom bonded directly to the oxygen atom of the ester linkage that is bonded to the ring Z' may be substituted with a hetero atom. This substituent hetero atom is preferably an oxygen atom or a sulfur atom, and is most preferably an oxygen atom. Moreover, although there are no particular limitations on the number of these substituent hetero-atoms, the number is preferably from 0 to 2, more preferably either 0 or 1, and is most preferably 0. In the case of a plurality of substituent hetero atoms, the plurality of hetero atoms may be either the same or different.

$Q^1$ represents an alkylene group of 1 to 12 carbon atoms or a single bond.

The alkylene group for $Q^1$ may be linear, branched or cyclic, but is preferably a linear or branched group. The alkylene group preferably has 1 to 5 carbon atoms, and more preferably 1 to 3 carbon atoms. Examples of this alkylene group include the same groups as those exemplified above for the alkylene group of Q" in $R^3$ to $R^6$ within the aforementioned general formula (w-1).

As $Q^1$, a methylene group, ethylene group, n-propylene group or single bond is preferred, and a single bond is particularly desirable.

$Y^1$ represents an alkylene group or fluorinated alkylene group of 1 to 4 carbon atoms.

Examples of $Y^1$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —CH$(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$— and —$C(CH_3)(CH_2CH_3)$—.

As $Y^1$, a fluorinated alkylene group is preferable, and a fluorinated alkylene group in which the carbon atom bonded to the adjacent sulfur atom is fluorinated is particularly desirable. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$— and —$CH_2CF_2CF_2CF_2$—.

Among these, —$CF_2$—, —$CF_2CF_2$—, —$CF_2CF_2CF_2$— and $CH_2CF_2CF_2$— are preferable, —$CF_2$—, —$CF_2CF_2$— and —$CF_2CF_2CF_2$— are more preferable, and —$CF_2$— is particularly desirable.

As the compound (I-1), a compound represented by general formula (I-10) shown below (hereafter referred to as "compound (I-10)") is preferred.

[Chemical Formula 9]

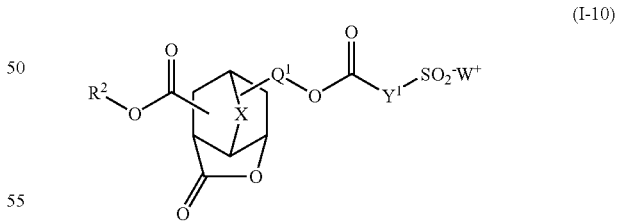

(I-10)

wherein $W^+$, $R^2$, $Q^1$ and $Y^1$ are as defined above for general formula (I-1); and X represents an alkylene group, —O—, —S—, —O—$R^7$— or —S—$R^8$—, wherein $R^7$ and $R^8$ each independently represents an alkylene group of 1 to 5 carbon atoms.

In formula (I-10), $W^+$, $R^2$, $Q^1$ and $Y^1$ are the same as $W^+$, $R^2$, $Q^1$ and $Y^1$ in general formula (I-1).

X represents an alkylene group, —O—, —S—, —O—$R^7$— or —S—$R^8$—, wherein $R^7$ and $R^8$ each independently represents an alkylene group of 1 to 5 carbon atoms.

As the alkylene group for X, a linear or branched alkylene group is preferred, and examples thereof include the same groups as those exemplified above for the alkylene group in $R^3$ to $R^6$ within general formula (w-1). Of the various possibilities, the number of carbon atoms within the alkylene group is preferably from 1 to 5, more preferably from 1 to 3, still more preferably from 1 to 2, and is most preferably 1.

The alkylene group of 1 to 5 carbon atoms for $R^7$ or $R^8$ is the same as the alkylene group for X. In the case of a —O—$R^7$— group, either O (the oxygen atom) or $R^7$ may be bonded to the carbon atom that constitutes part of the 5-membered ring that includes the ester linkage. Similarly, in the case of a —S—$R^8$— group, either S (the sulfur atom) or $R^8$ may be bonded to the carbon atom that constitutes part of the 5-membered ring that includes the ester linkage.

As X, an alkylene group or —O— is preferred, an alkylene group is more preferred, a methylene group or ethylene group is still more preferred, and a methylene group is the most desirable.

The compound (I) is a novel compound.

The compound (I) is useful as a precursor during the production of a compound (B1) described below.

<<Method of Producing Compound (I)>>

An example of a method of producing the compound (I) of the present invention is a method in which, as described below, a compound represented by general formula G-$(Z^{01})^-$W$^+$ is reacted with a compound represented by general formula $Z^{02}$-H.

G-$(Z^{01})^-$W$^+$+$Z^{02}$-H→$Z^{02}$-$(Z^{01})^-$W$^+$+G-H wherein $Z^{01}$-$(Z^{01})^-$ represents $Z^-$ in the above general formula (I), $(Z^{01})^-$ represents the anion moiety-containing portion of the anion moiety-containing group in $Z^-$, $Z^{02}$ represents the group obtained when $(Z^{01})^-$ is excluded from $Z^-$, G represents a dissociable group, and W$^+$ is as defined for W$^+$ in general formula (I).

In the formula, G represents a dissociable group, and an example thereof is a hydroxyl group.

W$^+$ is the same as W$^+$ in general formula (I).

$(Z^{01})^-$ represents the anion moiety-containing portion of the anion moiety-containing group in $Z^-$ within the above formula (I).

$Z^{02}$ represents the group obtained when $(Z^{01})^-$ is excluded from $Z^-$ in the formula (I), and includes the ring structure and the ester linkage-containing group in $Z^-$ within formula (I).

Specifically, a preferred compound (I-1) of the compound (I) of the present invention can be produced by subjecting a compound represented by general formula (I-1-1) shown below (hereafter referred to as "compound (I-1-1)") and a compound represented by general formula (I-1-2) shown below (hereafter referred to as "compound (I-1-2)") to a dehydration/condensation.

[Chemical Formula 10]

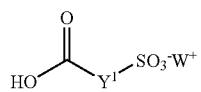
(I-1-1)

-continued

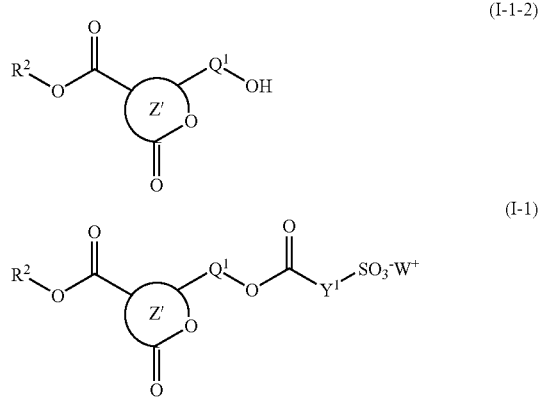

wherein W$^+$, the ring Z', $R^2$, $Q^1$ and $Y^1$ are as defined above for general formula (I-1).

W$^+$ and $Y^1$ in formula (I-1-1), and the ring Z', $R^2$ and $Q^1$ in formula (I-1-2) are the same as W$^+$, $Y^1$, the ring Z', $R^2$ and $Q^1$ respectively within the above general formula (I-1).

As the compound (I-1-1) and the compound (I-1-2), commercially available compounds may be used, or the compounds may be synthesized.

For example, of the various compounds (I-1-1), in the case of a compound (I-1-1A) in which W$^+$ represents an alkali metal ion, although there are no particular limitations, the compound can be synthesized by a method including the steps of subjecting a compound represented by general formula (I-1-1a) shown below (hereafter referred to as "compound (I-1-1a)") to an alkali treatment to obtain a compound represented by general formula (I-1-1b) shown below (hereafter referred to as "compound (I-1-1b)") (hereafter, this step is referred to as "step (i)"), and then heating the compound (I-1-1b) in the presence of an acid to obtain the compound (I-1-1A) (hereafter, this step is referred to as "step (ii)"),

[Chemical Formula 11]

(I-1-1-1a)

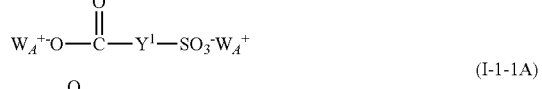
(I-1-1b)

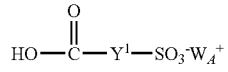
(I-1-1A)

wherein $R^1$ represents an alkyl group of 1 to 5 carbon atoms, $W_A^+$ represents an alkali metal ion, and $Y^1$ is as defined above in general formula (I-1).

In the formula, $R^1$ represents an alkyl group of 1 to 5 carbon atoms.

$W_A^+$ represents an alkali metal ion, and is the same as the alkali metal ions exemplified for W$^+$.

$Y^1$ is as defined above in general formula (I-1).

In step (i) above, as the compound (I-1-1a), a commercially available compound may be used.

In step (i), the alkali treatment can be conducted, for example, by heating the compound (I-1-1a) in the presence of an alkali. More specifically, the alkali treatment can be conducted by dissolving the compound (I-1-1a) in a solvent such as water or tetrahydrofuran or the like, adding an alkali to the resulting solution, and then heating the solution.

Examples of the alkali include sodium hydroxide, potassium hydroxide and lithium hydroxide.

The amount of the alkali used is preferably 1 to 5 mols, and more preferably 2 to 4 mols, per 1 mol of the compound (I-1-1a).

The heating temperature is preferably 20 to 130° C., and more preferably about 50 to 110° C. The heating time depends on factors such as the heating temperature, but in general, the heating time is preferably 0.5 to 12 hours, and more preferably 1 to 5 hours.

After the alkali treatment, neutralization may be conducted. The neutralization can be conducted by adding an acid such as hydrochloric acid, sulfuric acid or p-toluenesulfonic acid or the like to the reaction liquid obtained after the alkali treatment. It is preferable to conduct the neutralization so that the pH of the reaction liquid after addition of the acid is within the range of 6 to 8.

After the reaction, the compound (I-1-b) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

Step (ii) above may be performed, for example, by dissolving the compound (I-1-1b) in a solvent such as acetonitrile or methyl ethyl ketone or the like, adding an acid to the resulting solution, and then heating the solution.

In step (ii), as the acid, an acid which exhibits stronger acidity than the compound (I-1-1A) is used. Here, the expression "an acid which exhibits stronger acidity than the compound (I-1-1A)" describes an acid that has a larger pKa (25° C.) value than the —COOH group within the compound (I-1-1A). By using such an acid, the —COO$^-$W$_A{}^+$ moiety within the compound (I-1-1b) is converted to —COOH, thus yielding the compound (I-1-1A). Examples of such an acid include p-toluenesulfonic acid, sulfuric acid and hydrochloric acid.

The amount of the acid used is preferably 0.5 to 3 mols, and more preferably 1 to 2 mols, per 1 mol of the compound (I-1-1b).

The heating temperature is preferably 20 to 150° C., and more preferably about 50 to 120° C. The heating time depends on factors such as the heating temperature, but in general, the heating time is preferably 0.5 to 12 hours, and more preferably 1 to 5 hours.

After the reaction, the compound (I-1-1A) within the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

The compound (I-1-1B), in which W$^+$ is the ion (w-1), can be produced, for example, by dissolving the compound (I-1-1A) in a solvent, and then adding an amine or ammonium salt corresponding with the ion (w-1) to the solution.

Furthermore, in the production process for the compound (I-1) described below, by mixing the compound (I-1-1A), the amine or ammonium salt mentioned above, and the compound (I-1-2) within a reaction solvent, the entire process from the production of the compound (I-1-1B) through to the production of the compound (I-1) via a dehydration/condensation reaction can be conducted in a single batch. In such a case, the reaction solvent may be any solvent capable of dissolving the compound (I-1-1A) and the compound (I-1-2), and specific examples thereof include tetrahydrofuran (THF), acetone, dimethylformamide (DMF), dimethylacetamide, dimethylsulfoxide (DMSO) and acetonitrile.

In the case where the amine or ammonium salt mentioned above is mixed with the solution and the dehydration/condensation reaction is then conducted, the amount added of the compound (I-1-2) is preferably 1 to 3 mols, and more preferably 1 to 2 mols, per 1 mol of the compound (I-1-1A).

The amount added of the amine or ammonium salt is preferably about 1 to 3 mols, and more preferably 1 to 2 mols, per 1 mol of the compound (I-1-1A).

The reaction temperature is preferably within a range from −20 to 40° C., and is more preferably from 0 to 30° C. The reaction time depends on factors such as the reactivity of the compound (I-1-1A) and the compound (I-1-2), and the reaction temperature, but in general, the heating time is preferably 1 to 120 hours, and more preferably 1 to 48 hours.

In the case where the dehydration/condensation reaction is conducted without mixing the amine or ammonium salt into the solution, the dehydration/condensation reaction of the compound (I-1-1) and the compound (I-1-2) can be conducted, for example, by dissolving the compound (I-1-1) and the compound (I-1-2) in an aprotic organic solvent such as dichloroethane, benzene, toluene, ethylbenzene, chlorobenzene, acetonitrile or N,N-dimethylformamide, and then stirring the resulting solution.

In the dehydration/condensation reaction, as the organic solvent, it is particularly desirable to use an aromatic organic solvent such as toluene, xylene or chlorobenzene, as the yield and purity and the like of the obtained compound (I-1) are improved.

The reaction temperature for the dehydration/condensation reaction is preferably about 20 to 200° C., and more preferably 70 to 170° C. The reaction time varies depending on the reactivity of the compound (I-1-1) and the compound (I-1-2), and the reaction temperature and the like, but in general, the reaction time is preferably 1 to 40 hours, and more preferably 10 to 35 hours.

In the dehydration/condensation reaction, the amount used of the compound (I-1-1) is not particularly limited, but in general, the amount of the compound (I-1-1) is preferably 0.2 to 3 mols, more preferably 0.5 to 2 mols, and most preferably 0.75 to 1.5 mols, per 1 mol of the compound (I-1-2).

The dehydration/condensation reaction is preferably conducted in the presence of an acidic catalyst.

Examples of the acidic catalyst include organic acids such as p-toluenesulfonic acid, and inorganic acids such as sulfuric acid and hydrochloric acid. These acidic catalysts may be used individually, or in a combination of two or more acids.

In the dehydration/condensation reaction, the acidic catalyst may be used in a catalyst amount, or in an amount corresponding to the solvent. In general, the amount of the acidic catalyst is 0.001 to 5 mols per 1 mol of the compound (I-1-2).

The dehydration/condensation reaction may be conducted while removing the generated water by using a Dean-Stark apparatus. In this manner, the reaction time can be shortened.

Further, in the dehydration/condensation reaction, a dehydrating agent such as 1,1'-carbonyldiimidazole or N,N'-dicyclohexylcarbodiimide may also be used. When a dehydrating agent is used, in general, the amount of the dehydrating agent is preferably 0.2 to 5 mols, and more preferably 0.5 to 3 mols, per 1 mol of the compound (I-1-2).

In a similar manner, a particularly preferred compound (I-10) of the compound (I) of the present invention can be produced by subjecting the compound (I-1-1) and a compound represented by general formula (I-10-2) shown below (hereafter referred to as "compound (I-10-2)") to a dehydration/condensation.

[Chemical Formula 12]

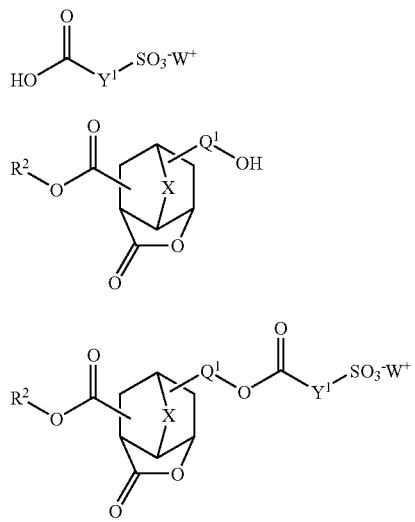

wherein $W^+$, $X$, $R^2$, $Q^1$ and $Y^1$ are as defined above for general formula (I).

Specific examples of preferred compounds of the compound (I-1-1) include the compounds represented by formulas (I-1-101) to (I-1-112) shown below. Of these, the compound represented by formula (I-1-101) is particularly desirable.

[Chemical Formula 13]

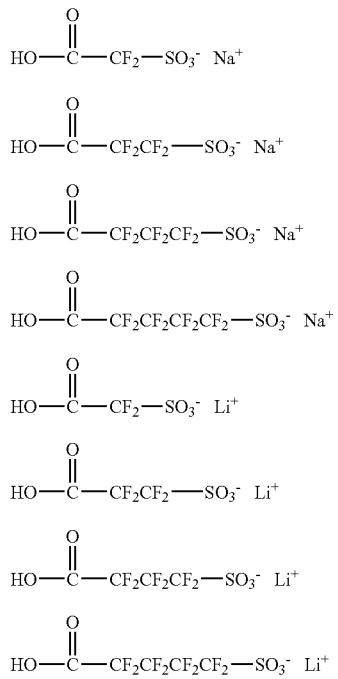

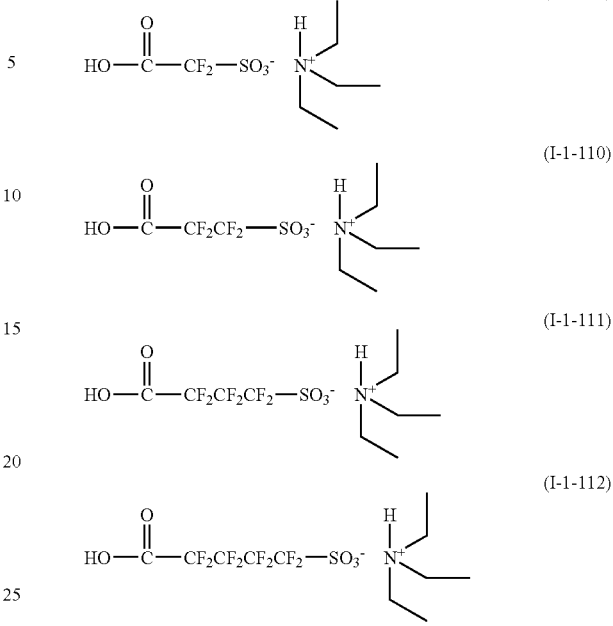

Furthermore, specific examples of preferred compounds of the compound (I-10-2) include the compounds represented by formulas (I-10-201) to (I-10-248) shown below. Of these, the compound represented by formula (I-10-201) is particularly desirable.

[Chemical Formula 14]

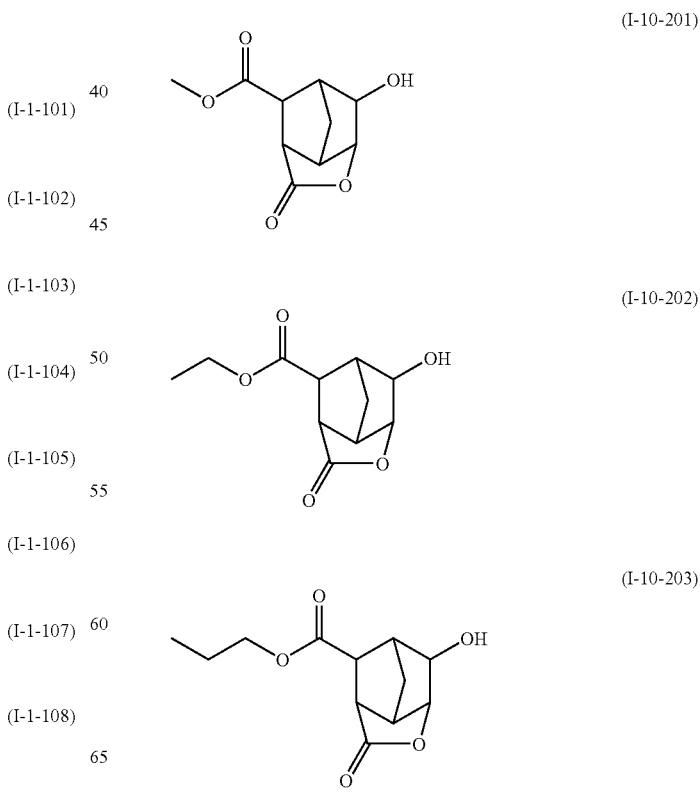

(I-10-204)
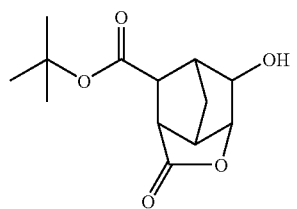
(I-10-205)
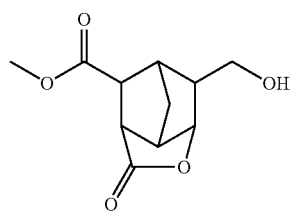
(I-10-206)
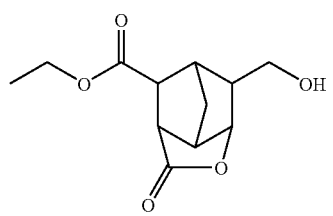
(I-10-207)
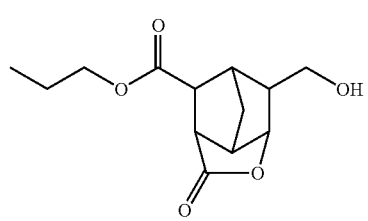
(I-10-208)
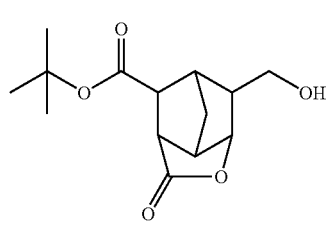
(I-10-209)
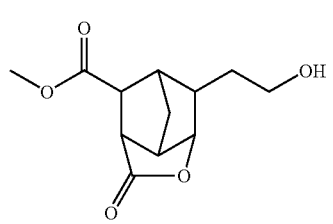
(I-10-210)
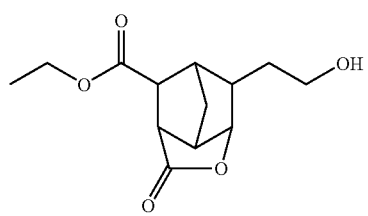
(I-10-211)
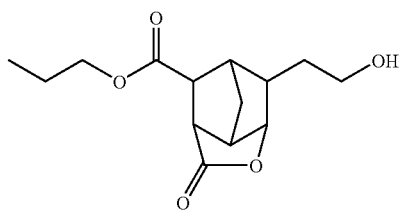
(I-10-212)
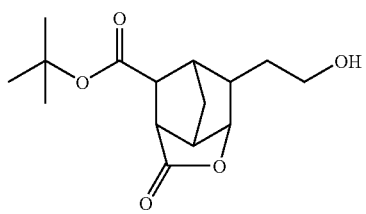
(I-10-213)
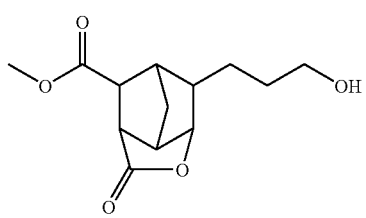
(I-10-214)
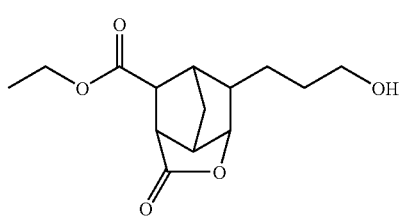
(I-10-215)
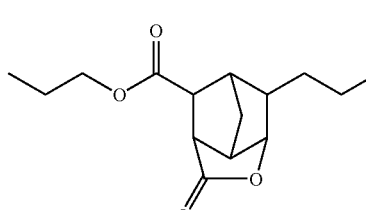
(I-10-216)
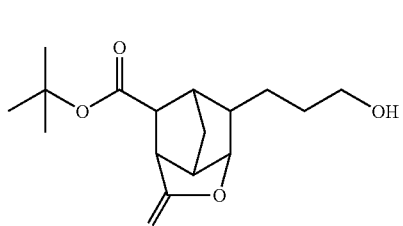
[Chemical Formula 15]
(I-10-217)
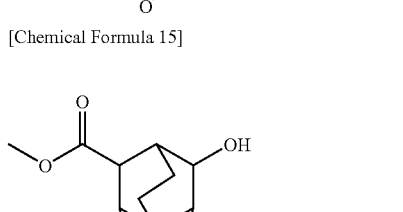

(I-10-218)
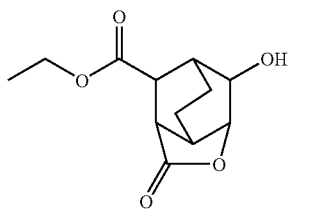
(I-10-219)
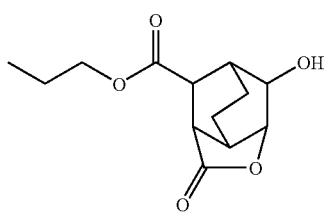
(I-10-220)
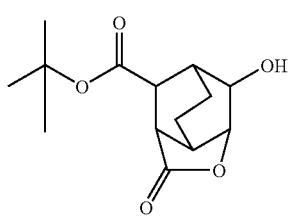
(I-10-221)
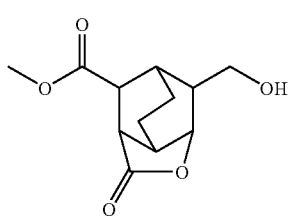
(I-10-222)
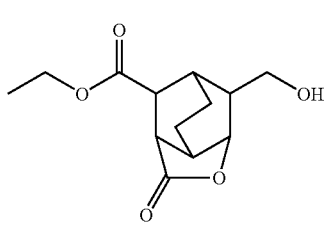
(I-10-223)
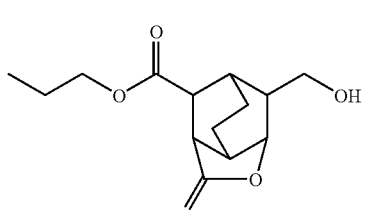
(I-10-224)
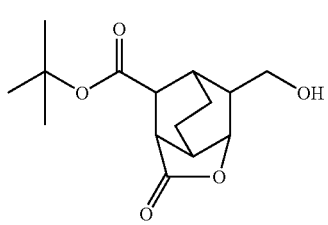
(I-10-225)
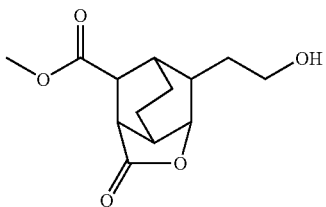
(I-10-226)
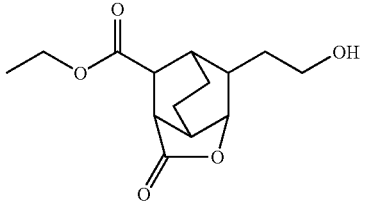
(I-10-227)
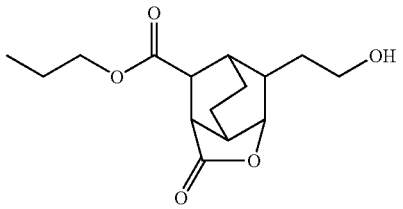
(I-10-228)
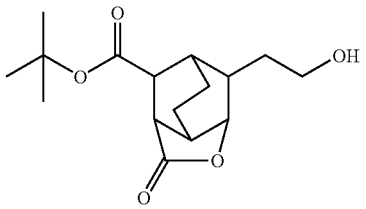
(I-10-229)
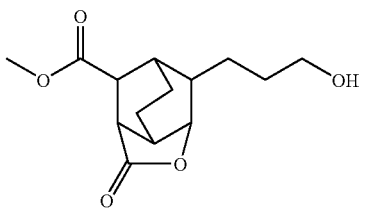
(I-10-230)
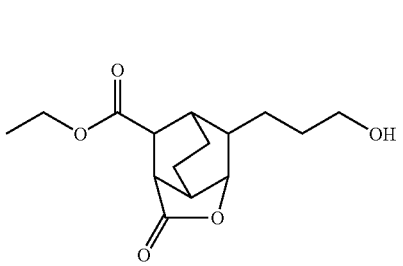
(I-10-231)
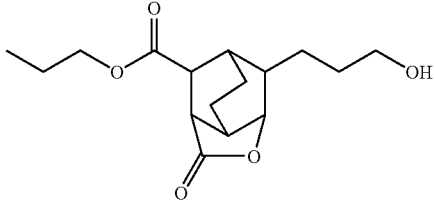

(I-1-232)
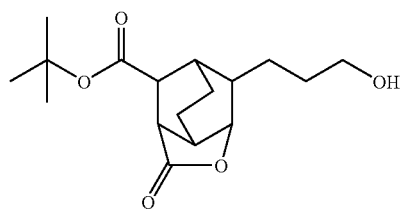
[Chemical Formula 16]
(I-10-233)
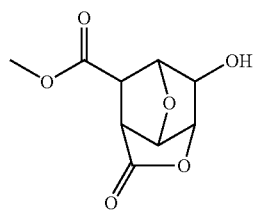
(I-10-234)
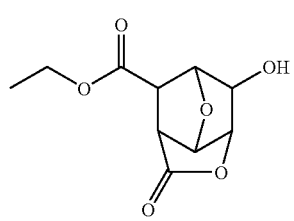
(I-1-235)
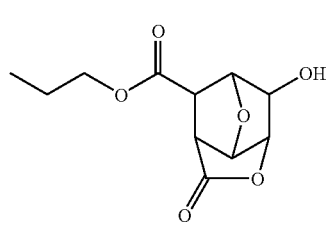
(I-10-236)
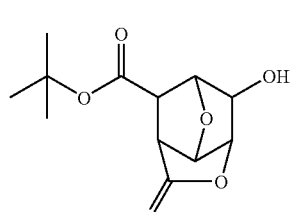
(I-10-237)
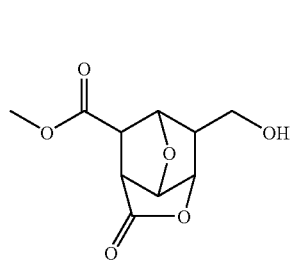
(I-10-238)
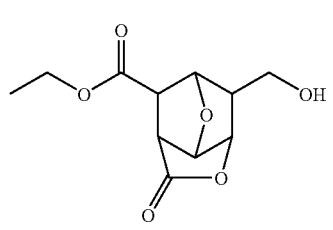
(I-1-239)
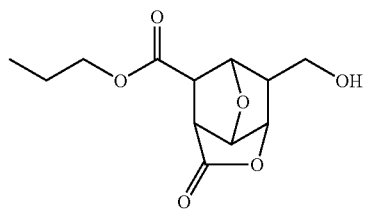
(I-10-240)
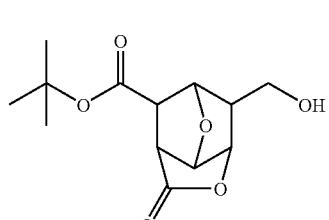
(I-10-241)
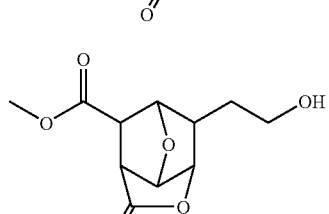
(I-10-242)
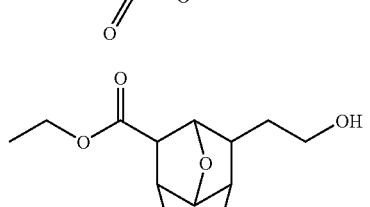
(I-10-243)
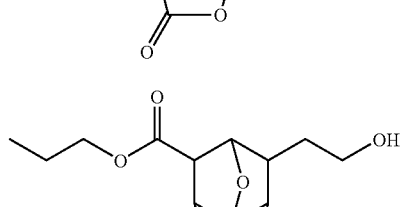
(I-10-244)
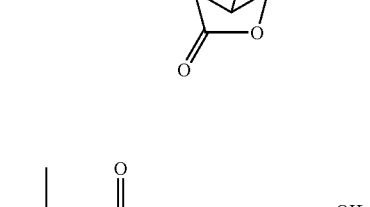
(I-10-245)
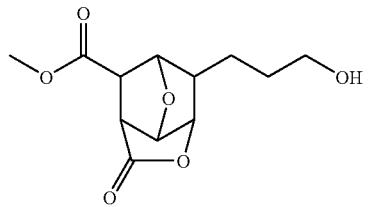

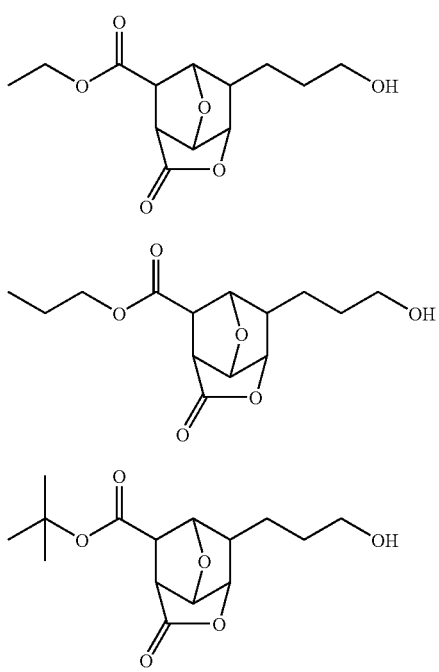

(I-10-246)

(I-10-247)

(I-10-248)

The structure of the compound (I) obtained in the above-described manner can be confirmed by a general organic analysis methods such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elemental analysis and X-ray diffraction analysis.

<<Compound (B1)>>

The compound (B1) of the present invention is represented by general formula (b1-2) above.

In general formula (b1-2), $Z^-$ is as defined for $Z^-$ in general formula (I).

As the organic cation for $A^+$, there is no particular limitation, and any cation conventionally known as a cation moiety for an onium salt-based acid generator can be appropriately selected for use. More specifically, a cation moiety represented by general formula (b'-1), (b'-2), (b-6) or (b-7) show below can be favorably used.

[Chemical Formula 17]

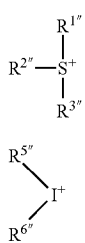

(b'-1)

(b'-2)

wherein $R^{1'''}$ to $R^{3'''}$, $R^{5'''}$ and $R^{6'''}$ each independently represents an aryl group or alkyl group, and two of $R^{1'''}$ to $R^{3'''}$ may be bonded to each other to form a ring with the sulfur atom in the formula, with the proviso that at least one of $R^{1'''}$ to $R^{3'''}$ represents an aryl group, and at least one of $R^{5'''}$ and $R^{6'''}$ represents an aryl group.

[Chemical Formula 18]

(b-6)

(b-7)

wherein $R^{40}$ represents a hydrogen atom or an alkyl group; $R^{41'}$ represents an alkyl group, acetyl group, carboxyl group or hydroxyalkyl group; each of $R^{42'}$, $R^{43'}$ and $R^{44}$ to $R^{46}$ independently represents an alkyl group, acetyl group, alkoxy group, carboxyl group or hydroxyalkyl group; each of $n_0$, $n_1'$ to $n_3'$, $n_4$ and $n_5$ independently represents an integer of 0 to 3, with the proviso that $n_0+n_1'$ is 5 or less; and $n_6$ represents an integer of 0 to 2.

In formula (b'-1), $R^{1'''}$ to $R^{3'''}$ each independently represents an aryl group or an alkyl group. In formula (b'-1), two of $R^{1'''}$ to $R^{3'''}$ may be bonded to each other to form a ring with the sulfur atom in the formula.

Further, among $R^{1'''}$ to $R^{3'''}$, at least one group represents an aryl group. Among $R^{1'''}$ to $R^{3'''}$, two or more groups are preferably aryl groups, and it is particularly desirable that all of $R^{1'''}$ to $R^{3'''}$ are aryl groups.

The aryl group for $R^{1'''}$ to $R^{3'''}$ is not particularly limited. Examples thereof include an unsubstituted aryl group having 6 to 20 carbon atoms, a substituted aryl group in which some or all of the hydrogen atoms of an aforementioned unsubstituted aryl group have been substituted with alkyl groups, alkoxy groups, alkoxyalkyloxy groups, alkoxycarbonylalkyloxy groups, halogen atoms, or hydroxyl groups or the like, and —$(R^{4'})$—C—(=O)—$R^{5'}$. $R^{4'}$ represents an alkylene group of 1 to 5 carbon atoms. $R^{5'}$ represents an aryl group. As the aryl group for $R^{5'}$, the same groups as the aryl group for $R^{1'''}$ to $R^{3'''}$ can be exemplified.

The unsubstituted aryl group is preferably an aryl group having 6 to 10 carbon atoms because it can be synthesized at a low cost. Specific examples thereof include a phenyl group or a naphthyl group.

The alkyl group as the substituent for the substituted aryl group is preferably an alkyl group having 1 to 5 carbon atoms, and is most preferably a methyl group, ethyl group, propyl group, n-butyl group or tert-butyl group.

The alkoxy group as the substituent for the substituted aryl group is preferably an alkoxy group having 1 to 5 carbon atoms, and is most preferably a methoxy group, ethoxy group, n-propoxy group, iso-propoxy group, n-butoxy group or tert-butoxy group.

The halogen atom as the substituent for the substituted aryl group is preferably a fluorine atom.

Examples of the alkoxyalkyloxy group as the substituent for the substituted aryl group include groups represented by a general formula: —O—C($R^{47}$)($R^{48}$)—O—$R^{49}$ (wherein each of $R^{47}$ and $R^{48}$ independently represents a hydrogen atom or a linear or branched alkyl group, and $R^{49}$ represents an alkyl group).

The alkyl group for $R^{47}$ and $R^{48}$ preferably has 1 to 5 carbon atoms, and may be either linear or branched, and is preferably an ethyl group or a methyl group, and most preferably a methyl group.

It is preferable that at least one of $R^{47}$ and $R^{48}$ is a hydrogen atom, and it is particularly desirable that either one of $R^{47}$ and $R^{48}$ is a hydrogen atom, and the other is a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, ethyl group, propyl group, n-butyl group and tert-butyl group.

The cyclic alkyl group for $R^{49}$ preferably has 4 to 15 carbon atoms, more preferably 4 to 12 carbon atoms, and most preferably 5 to 10 carbon atoms. Specific examples thereof include groups in which one or more hydrogen atoms have been removed from a monocycloalkane or a polycycloalkane such as a bicycloalkane, tricycloalkane or tetracycloalkane, and which may or may not be substituted with alkyl groups of 1 to 5 carbon atoms, fluorine atoms or fluorinated alkyl groups. Examples of the monocycloalkane include cyclopentane and cyclohexane. Examples of the polycycloalkane include adamantane, norbornane, isobornane, tricyclodecane and tetracyclododecane. Among these, groups in which one or more hydrogen atoms have been removed from adamantane are preferable.

Examples of the alkoxycarbonylalkyloxy group as the substituent for the substituted aryl group include groups represented by a general formula: —O—$R^{50}$—C(=O)—O—$R^{51}$ (wherein $R^{50}$ represents a linear or branched alkylene group, and $R^{51}$ represents a tertiary alkyl group).

The linear or branched alkylene group for $R^{50}$ preferably has 1 to 5 carbon atoms, and examples thereof include a methylene group, ethylene group, trimethylene group, tetramethylene group and 1,1-dimethylethylene group.

Examples of tertiary alkyl groups for $R^{51}$ include a 2-methyl-2-adamantyl group, 2-ethyl-2-adamantyl group, 1-methyl-1-cyclopentyl group, 1-ethyl-1-cyclopentyl group, 1-methyl-1-cyclohexyl group, 1-ethyl-1-cyclohexyl group, 1-(1-adamantyl)-1-methylethyl group, 1-(1-adamantyl)-1-methylpropyl group, 1-(1-adamantyl)-1-methylbutyl group, 1-(1-adamantyl)-1-methylpentyl group, 1-(1-cyclopentyl)-1-methylethyl group, 1-(1-cyclopentyl)-1-methylpropyl group, 1-(1-cyclopentyl)-1-methylbutyl group, 1-(1-cyclopentyl)-1-methylpentyl group, 1-(1-cyclohexyl)-1-methylethyl group, 1-(1-cyclohexyl)-1-methylpropyl group, 1-(1-cyclohexyl)-1-methylbutyl group, 1-(1-cyclohexyl)-1-methylpentyl group, tert-butyl group, tert-pentyl group and tert-hexyl group.

The aryl group for $R^{1\prime\prime\prime}$ to $R^{3\prime\prime\prime}$ is preferably a phenyl group or a naphthyl group.

The alkyl group for $R^{1\prime\prime\prime}$ to $R^{3\prime\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, ethyl group, n-propyl group, isopropyl group, n-butyl group, isobutyl group, n-pentyl group, cyclopentyl group, hexyl group, cyclohexyl group, nonyl group, and decanyl group. Among these, a methyl group is most preferable because it yields excellent resolution and can be synthesized at a low cost.

When two of $R^{1\prime\prime\prime}$ to $R^{3\prime\prime\prime}$ are bonded to each other to form a ring with the sulfur atom in the formula, it is preferable that the two of $R^{1\prime\prime\prime}$ to $R^{3\prime\prime\prime}$ form a 3- to 10-membered ring including the sulfur atom, and it is particularly desirable that the two of $R^{1\prime\prime\prime}$ to $R^{3\prime\prime\prime}$ form a 5- to 7-membered ring including the sulfur atom.

When two of $R^{1\prime\prime\prime}$ to $R^{3\prime\prime\prime}$ are bonded to each other to form a ring with the sulfur atom, the remaining one of $R^{1\prime\prime\prime}$ to $R^{3\prime\prime\prime}$ is preferably an aryl group. As examples of the aryl group, the same groups as the above-mentioned aryl groups for $R^{1\prime\prime\prime}$ to $R^{3\prime\prime\prime}$ can be exemplified.

Specific examples of cation moiety represented by formula (b'-1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethyloxy)phenyl)diphenylsulfonium, (4-(tert-butoxycarbonylmethyloxy)-3,5-dimethyl)diphenylsulfonium, (4-(2-methyl-2-adamantyloxycarbonylmethyloxy)phenyl)diphenylsulfonium, (4-(2-methyl-2-adamantyloxycarbonylmethyloxy)-3,5-dimethylphenyl)diphenylsulfonium, tri(4-methylphenyl)sulfonium, dimethyl(4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl)phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiophenium, 1-(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl)tetrahydrothiopyranium and 1-(4-methylphenyl)tetrahydrothiopyranium.

In formula (b'-2), $R^{5\prime\prime\prime}$ and $R^{6\prime\prime\prime}$ each independently represents an aryl group or an alkyl group. At least one of $R^{5\prime\prime\prime}$ and $R^{6\prime\prime\prime}$ represents an aryl group. It is preferable that both of $R^{5\prime\prime\prime}$ and $R^{6\prime\prime\prime}$ represent an aryl group.

As the aryl group for $R^{5\prime\prime\prime}$ and $R^{6\prime\prime\prime}$, the same groups as the aryl groups for $R^{1\prime\prime\prime}$ to $R^{3\prime\prime\prime}$ can be exemplified.

As the alkyl group for $R^{5\prime\prime\prime}$ and $R^{6\prime\prime\prime}$, the same groups as the alkyl groups for $R^{1\prime\prime\prime}$ to $R^{3\prime\prime\prime}$ can be exemplified.

It is particularly desirable that both $R^{5\prime\prime\prime}$ and $R^{6\prime\prime\prime}$ represent phenyl groups.

Specific examples of the cation moiety represented by general formula (b'-2) include diphenyliodonium and bis(4-tert-butylphenyl)iodonium.

In general formulas (b-6) and (b-7), with respect to $R^{40}$, $R^{41\prime}$ to $R^{43\prime}$, and $R^{44}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably an aforementioned alkyl group in which one or more hydrogen atoms have been substituted with hydroxyl groups, and examples thereof include a hydroxymethyl group, hydroxyethyl group and hydroxypropyl group.

$n_0$ is preferably 0 or 1.

$n_1'$ is preferably 0 to 2.

It is preferable that each of $n_2'$ and $n_3'$ independently represents 0 or 1, and more preferably 0.

$n_4$ is preferably 0 to 2, and is more preferably 0 or 1.

$n_5$ is preferably 0 or 1, and is most preferably 0.

$n_6$ is preferably 0 or 1.

In the present invention, as $A^+$, a cation moiety represented by formula (b'-1) is preferred, and cation moieties represented by formulas (b'-1-1) to (b'-1-10) shown below are particularly desirable.

[Chemical Formula 19]

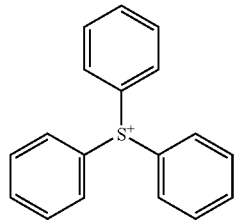
(b'-1-1)

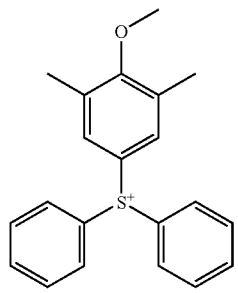
(b'-1-2)

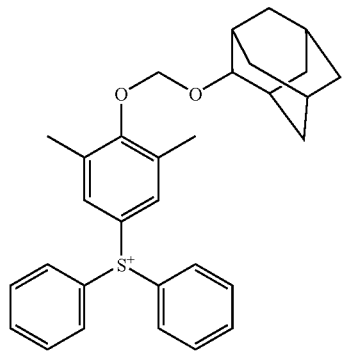
(b'-1-3)

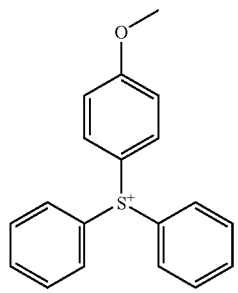
(b'-1-4)

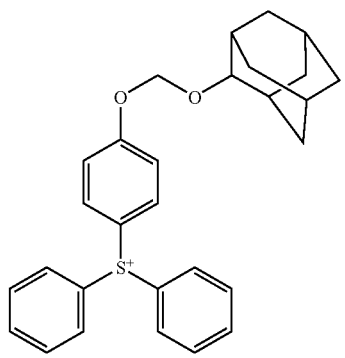
(b'-1-5)

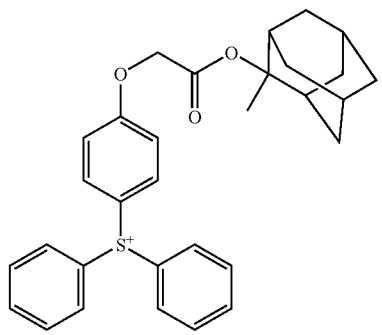
(b'-1-6)

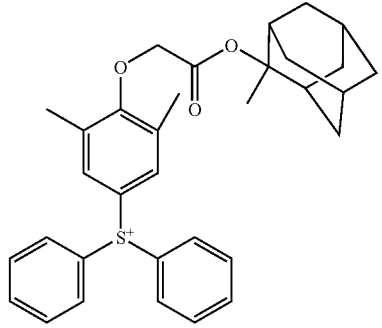
(b'-1-7)

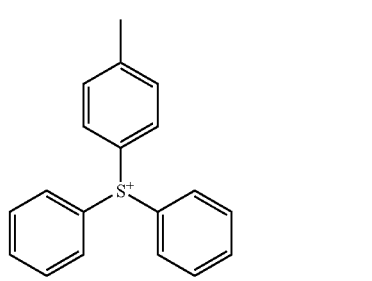
(b'-1-8)

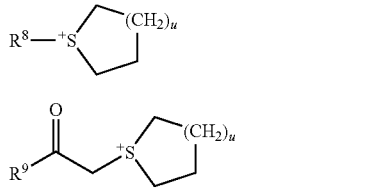
(b'-1-9)

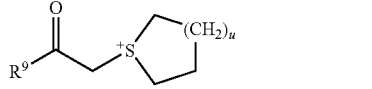
(b'-1-10)

In formulas (b'-1-9) and (b'-1-10), $R^8$ and $R^9$ each independently represents a phenyl group or naphthyl group that may have a substituent, an alkyl group or alkoxy group of 1 to 5 carbon atoms, or a hydroxyl group.

u represents an integer of 1 to 3, and is most preferably 1 or 2.

The compound (B1) is a compound in which the cation moiety W⁺ in the aforementioned compound (I) is substituted with the aforementioned organic cation moiety A⁺, and preferred examples of the compound (B1) include compounds represented by formula (b1-2-1) shown below. Particularly preferred compounds include those compounds represented by general formula (b1-2-10) shown below.

[Chemical Formula 20]

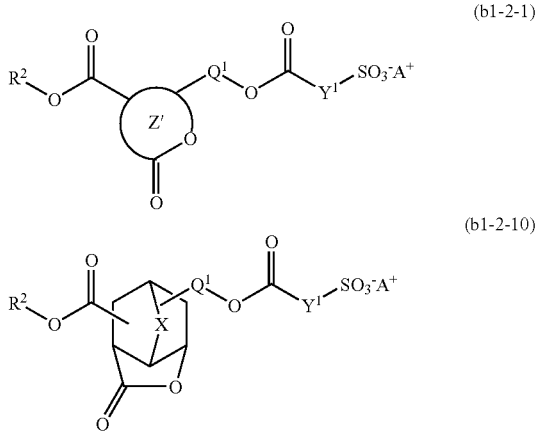

wherein A⁺ is as defined above for formula (b1-2), and the ring Z', $R^2$, $Q^1$, $Y^1$, and X are as defined above for formula (I-10).

<<Method of Producing Compound (B1)>>

An example of the method of producing the compound (B1) involves reacting the aforementioned compound (I) with a compound (II) represented by general formula (II) shown below.

[Chemical Formula 21]

wherein A⁺ is as defined for A⁺ in general formula (b1-2) above, and U⁻ represents a low nucleophilic halogen ion, an ion which is capable of generating an acid exhibiting a lower acidity than the compound (I), $BF_4^-$, $AsF_6^-$, $SbF_6^-$, $PF_6^-$ or $ClO_4^-$.

As the low nucleophilic halogen ion for U⁻, a bromine ion and a chlorine ion can be exemplified.

As the ion for U⁻ which is capable of generating an acid exhibiting a lower acidity than the compound (I), a p-toluenesulfonic acid ion, a methanesulfonic acid ion, a benzenesulfonic acid ion and a trifluoromethanesulfonic acid ion can be exemplified.

The compound (I) can be reacted with the compound (II), for example, by dissolving a mixture of the compound (I) and the compound (II) in a solvent such as water, dichloromethane, acetonitrile, methanol, chloroform or methylene chloride, and then stirring the resulting solution to effect a reaction.

The reaction temperature is preferably 0 to 150° C., and more preferably 0 to 100° C. The reaction time varies depending on the reactivity of the compound (I) and the compound (II), and the reaction temperature and the like, but in general, the reaction time is preferably 0.5 to 10 hours, and more preferably 1 to 5 hours.

Generally, the amount of the compound (II) used in the reaction is preferably 0.3 to 2 mols per 1 mol of the compound (I).

Following reaction, the compound (B1) can be extracted, for example, by extracting the product into an organic layer, washing with water, and then concentrating the organic layer.

The structure of the compound obtained in the above-described manner can be confirmed by a general organic analysis methods such as ¹H-nuclear magnetic resonance (NMR) spectrometry, ¹³C-NMR spectrometry, ¹⁹F-NMR spectrometry, infrared absorption (IR) spectrometry, mass spectrometry (MS), elementary analysis and X-ray diffraction analysis.

The compound (B1) is a novel compound that is useful as an acid generator, and can be blended within a resist composition as an acid generator.

<<Acid Generator>>

The acid generator of the present invention consists of the compound (B1) according to the present invention.

The acid generator is useful as an acid generator for a chemically amplified resist composition, for example, as an acid generator component (B) for the resist composition of the present invention described below.

<<Resist Composition>>

The resist composition of the present invention includes a base component (A) (hereafter, referred to as "component (A)") that exhibits changed solubility in an alkali developing solution under the action of acid, and an acid generator component (B) (hereafter, referred to as "component (B)") that generates acid upon exposure, wherein the component (B) includes an acid generator (B1) consisting of a compound represented by general formula (b1-2) above.

With respect to a resist film formed using the resist composition, when a selective exposure is conducted during formation of a resist pattern, acid is generated from the component (B), and the generated acid acts upon the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a nano-level resist pattern can be more easily formed.

Organic compounds having a molecular weight of 500 or more are broadly classified into low molecular weight organic compounds having a molecular weight of 500 to less than 2,000 (hereafter, frequently referred to as "low molecular weight compounds") and high molecular weight resins (polymer materials) having a molecular weight of 2,000 or more. Generally, as the aforementioned low molecular weight compound, a non-polymer is used. With respect to the aforementioned resin (polymer or copolymer), the molecular weight refers to the polystyrene equivalent value determined by gel permeation chromatography (GPC). Hereafter, the term "resin" refers to a resin having a molecular weight of 2,000 or more.

As the component (A), a resin that exhibits changed solubility in an alkali developing solution under the action of acid may be used. Alternatively, as the component (A), a low molecular weight material that exhibits changed solubility in an alkali developing solution under the action of acid may be used.

When the resist composition of the present invention is a negative resist composition, a base component that is soluble in an alkali developing solution is used as the component (A), and a cross-linking agent is blended into the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as an "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, as such resins enable the formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount added of the cross-linking agent is preferably within a range from 1 to 50 parts by weight, relative to 100 parts by weight of the alkali-soluble resin.

When the resist composition of the present invention is a positive resist composition, as the component (A), a base component that exhibits increased solubility in an alkali developing solution under the action of acid is used. The component (A) is insoluble in an alkali developing solution prior to exposure, but when acid is generated from the component (B) upon exposure, the solubility of the component (A) in an alkali developing solution increases. Therefore, in the formation of a resist pattern, by conducting selective exposure of a resist film formed by applying the positive resist composition onto a substrate, the exposed portions change from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component that exhibits increased solubility in an alkali developing solution under the action of acid. That is, the resist composition of the present invention is preferably a positive resist composition.

The component (A) may be a resin component (A1) that exhibits increased solubility in an alkali developing solution under the action of acid (hereafter, referred to as "component (A1)"), a low molecular weight compound (A2) that exhibits increased solubility in an alkali developing solution under the action of acid (hereafter, referred to as "component (A2)"), or a mixture of the component (A1) and the component (A2).

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned.

With respect to the "structural unit derived from an acrylate ester", the "α-position" (the carbon atom on the α-position) refers to the carbon atom having the carbonyl group bonded thereto, unless specified otherwise.

With respect to the acrylate ester, specific examples of the lower alkyl group for the substituent at the α-position include linear or branched lower alkyl groups such as a methyl group, ethyl group, propyl group, isopropyl group, n-butyl group, isobutyl group, tert-butyl group, pentyl group, isopentyl group and neopentyl group.

Specific examples of the halogenated lower alkyl group include groups in which some or all of the hydrogen atoms of an aforementioned "lower alkyl group for the substituent at the α-position" are substituted with halogen atoms. Examples of the halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group, and more preferably a hydrogen atom, a lower alkyl group or a fluorinated lower alkyl group is bonded to the α-position of the acrylate ester. In terms of industrial availability, a hydrogen atom or a methyl group is particularly desirable.

It is particularly desirable that the component (A1) have a structural unit (a1) derived from an acrylate ester containing an acid-dissociable, dissolution-inhibiting group.

Further, it is preferable that the component (A1) have a structural unit (a2) derived from an acrylate ester that contains a lactone-containing cyclic group, in addition to the structural unit (a1).

Furthermore, it is preferable that the component (A1) have a structural unit (a3) derived from an acrylate ester that contains a polar group-containing aliphatic hydrocarbon group, either in addition to the structural unit (a1), or in addition to the structural unit (a1) and the structural unit (a2).

Structural Unit (a1)

The structural unit (a1) is a structural unit derived from an acrylate ester containing an acid-dissociable, dissolution-inhibiting group.

As the acid-dissociable, dissolution-inhibiting group in the structural unit (a1), any of the groups that have been proposed as acid-dissociable, dissolution-inhibiting groups for the base resins of chemically amplified resists can be used, provided the group has an alkali dissolution-inhibiting effect that renders the entire component (A1) insoluble in an alkali developing solution prior to dissociation, and then following dissociation under the action of acid, increases the solubility of the entire component (A1) in the alkali developing solution.

Generally, groups that form either a cyclic or chain-like tertiary alkyl ester with the carboxyl group of the (meth) acrylic acid, and acetal-type acid-dissociable, dissolution-inhibiting groups such as alkoxyalkyl groups are widely known. The term "(meth)acrylate ester" is a generic term that includes both the acrylate ester having a hydrogen atom bonded on the α-position, and the methacrylate ester having a methyl group bonded on the α-position.

Here, a "tertiary alkyl ester" describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid-dissociable, dissolution-inhibiting groups".

Examples of tertiary alkyl ester-type acid-dissociable, dissolution-inhibiting groups include aliphatic branched, acid-dissociable, dissolution-inhibiting groups and aliphatic cyclic group-containing acid-dissociable, dissolution-inhibiting groups.

In the present description and claims, the term "aliphatic" is a relative concept used in relation to the term "aromatic", and defines a group or compound or the like that has no aromaticity.

The term "aliphatic branched" refers to a branched structure having no aromaticity.

The "aliphatic branched, acid-dissociable, dissolution-inhibiting group" is not limited to structures constituted of only carbon atoms and hydrogen atoms (namely, not limited to hydrocarbon groups), but is preferably a hydrocarbon group.

Further, the "hydrocarbon group" may be either saturated or unsaturated, but is preferably saturated.

As the aliphatic branched, acid-dissociable, dissolution-inhibiting group, tertiary alkyl groups of 4 to 8 carbon atoms are preferred, and specific examples thereof include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, lower alkoxy groups of 1 to 5 carbon atoms, a fluorine atom, fluorinated lower alkyl groups of 1 to 5 carbon atoms, and an oxygen atom (=O).

The basic ring of the "aliphatic cyclic group" exclusive of substituents is not limited to structures constituted from only carbon and hydrogen (namely, not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

Examples of such aliphatic cyclic groups include groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

As the aliphatic cyclic group-containing acid-dissociable, dissolution-inhibiting group, for example, a group that has a tertiary carbon atom on the ring structure of the cycloalkyl group can be mentioned. Specific examples include a 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, such as the groups bonded to the oxygen atom of the carbonyl group (—C(O)—O—) within the structural units represented by general formulas (a1"-1) to (a1"-6) shown below, can also be exemplified.

[Chemical Formula 22]

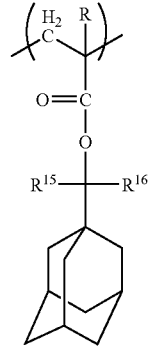

(a1"-1)

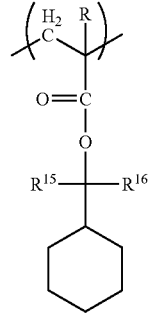

(a1"-2)

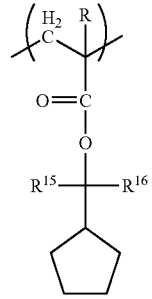

(a1"-3)

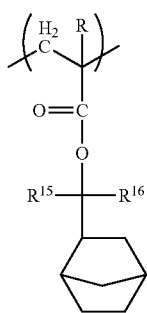
(a1″-4)

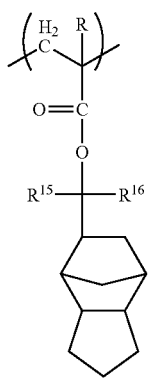
(a1″-5)

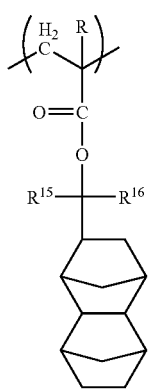
(a1″-6)

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group that may be bonded to the α-position of the aforementioned acrylate ester.

An "acetal-type acid-dissociable, dissolution-inhibiting group" generally substitutes a hydrogen atom at the terminal of an alkali-soluble group such as a carboxyl group or hydroxyl group, so as to be bonded with an oxygen atom. When acid is generated upon exposure, the generated acid acts to break the bond between the acetal-type acid-dissociable, dissolution-inhibiting group and the oxygen atom to which the acetal-type acid-dissociable, dissolution-inhibiting group is bonded.

Examples of acetal-type acid-dissociable, dissolution-inhibiting groups include groups represented by general formula (p1) shown below.

[Chemical Formula 23]

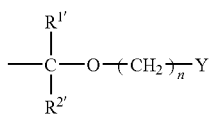
(p1)

wherein $R^{1\prime}$ and $R^{2\prime}$ each independently represents a hydrogen atom or a lower alkyl group, n represents an integer of 0 to 3, and Y represents a lower alkyl group or an aliphatic cyclic group.

In general formula (p1) above, n is preferably an integer of 0 to 2, more preferably 0 or 1, and is most preferably 0.

As the lower alkyl group for $R^{1\prime}$ and $R^{2\prime}$, the same groups as the lower alkyl groups for R above can be exemplified. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ is a hydrogen atom. That is, it is preferable that the acid-dissociable, dissolution-inhibiting group (p1) is a group represented by general formula (p1-1) shown below.

[Chemical Formula 24]

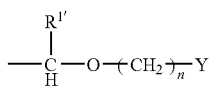
(p1-1)

wherein $R^{1\prime}$, n and Y are as defined above in general formula (p1).

As the lower alkyl group for Y, the same groups as the lower alkyl groups for R above can be exemplified.

As the aliphatic cyclic group for Y, any of the multitude of aliphatic monocyclic or polycyclic groups that have been proposed for conventional ArF resists and the like can be appropriately selected for use. For example, the same groups described above in connection with the "aliphatic cyclic group" can be exemplified.

Further, as the acetal-type acid-dissociable, dissolution-inhibiting group, groups represented by general formula (p2) shown below can also be exemplified.

[Chemical Formula 25]

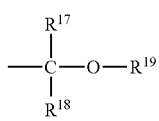
(p2)

wherein $R^{17}$ and $R^{18}$ each independently represents a linear or branched alkyl group or a hydrogen atom; and $R^{19}$ represents a linear, branched or cyclic alkyl group; or alternatively, $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferred, and a methyl group is most preferable.

It is particularly desirable that either one of $R^{17}$ and $R^{18}$ is a hydrogen atom, and the other is a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and is most preferably an ethyl group.

When $R^{19}$ represents a cyclic group, it preferably has 4 to 15 carbon atoms, more preferably 4 to 12 carbon atoms, and most preferably 5 to 10 carbon atoms. Examples of the cycloalkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of this cyclic group include tetrahydropyranyl group and tetrahydrofuranyl group.

As the structural unit (a1), it is preferable to use at least one unit selected from the group consisting of structural units represented by formula (a1-0-1) shown below and structural units represented by formula (a1-0-2) shown below.

[Chemical Formula 26]

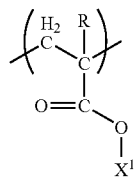

(a1-0-1)

wherein R represents a hydrogen atom, a lower alkyl group or a halogenated lower alkyl group; and $X^1$ represents an acid-dissociable, dissolution-inhibiting group.

[Chemical Formula 27]

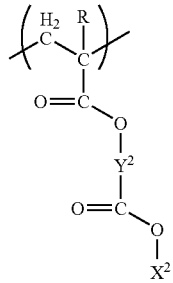

(a1-0-2)

wherein R represents a hydrogen atom, a lower alkyl group or a halogenated lower alkyl group; $X^2$ represents an acid-dissociable, dissolution-inhibiting group; and $Y^2$ represents an alkylene group or an aliphatic cyclic group.

In general formula (a1-0-1) shown above, the lower alkyl group or halogenated lower alkyl group for R is as defined for the lower alkyl group or halogenated lower alkyl group that may be bonded to the α-position of the aforementioned acrylate ester.

$X^1$ is not particularly limited as long as it is an acid-dissociable, dissolution-inhibiting group. Examples thereof include the aforementioned tertiary alkyl ester-type acid-dissociable, dissolution-inhibiting groups and acetal-type acid-dissociable, dissolution-inhibiting groups, and of these, tertiary alkyl ester-type acid-dissociable, dissolution-inhibiting groups are preferred.

In general formula (a1-0-2), R is as defined above for the lower alkyl group or halogenated lower alkyl group that may be bonded to the α-position of the aforementioned acrylate ester.

$X^2$ is the same as $X^1$ in formula (a1-0-1).

$Y^2$ is preferably an alkylene group of 1 to 10 carbon atoms or a divalent aliphatic cyclic group. As the aliphatic cyclic group, the same groups as those exemplified above in connection with the description of the "aliphatic cyclic group" can be used, with the exception that two hydrogen atoms have been removed from the group.

When $Y^2$ represents an alkylene group of 1 to 10 carbon atoms, it is more preferable that the number of carbons is 1 to 6, still more preferably 1 to 4, and most preferably 1 to 3.

When $Y^2$ represents a divalent aliphatic cyclic group, it is particularly desirable that the divalent aliphatic cyclic group is a group in which two or more hydrogen atoms have been removed from cyclopentane, cyclohexane, norbornane, isobornane, adamantane, tricyclodecane or tetracyclododecane.

Specific examples of the structural unit (a1) include structural units represented by general formulas (a1-1) to (a1-4) shown below.

[Chemical Formula 28]

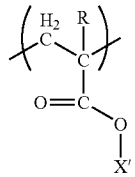

(a1-1

-continued (a1-2)
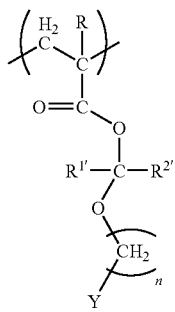

(a1-3)
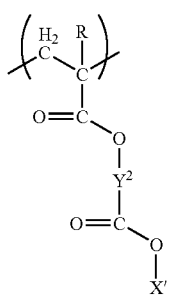

(a1-4)
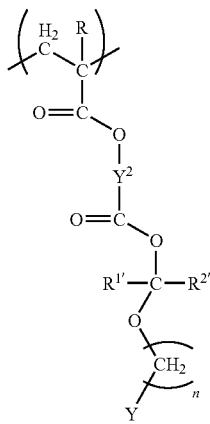

wherein X' represents a tertiary alkyl ester-type acid-dissociable, dissolution-inhibiting group; Y represents a lower alkyl group of 1 to 5 carbon atoms or an aliphatic cyclic group; n represents an integer of 0 to 3; $Y^2$ represents an alkylene group or aliphatic cyclic group that may have a substituent; R is as defined above in formula (a1-0-1); and $R^{1'}$ and $R^{2'}$ each independently represents a hydrogen atom or a lower alkyl group of 1 to 5 carbon atoms.

Examples of the tertiary alkyl ester-type acid-dissociable, dissolution-inhibiting group for X' include the same groups as those exemplified above for the tertiary alkyl ester-type acid-dissociable, dissolution-inhibiting group $X^1$ in formula (a1-0-1).

Examples of $R^{1'}$, $R^{2'}$, n and Y, include the same groups as those exemplified above for $R^{1'}$, $R^{2'}$, n and Y in general formula (p1) in connection with the description of the "acetal-type acid-dissociable, dissolution-inhibiting group".

Examples of $Y^2$ include the same groups as those exemplified above for $Y^2$ in general formula (a1-0-2).

Examples of the substituent within $Y^2$ include an alkyl group, oxygen atom, carbonyl group or ester linkage.

Specific examples of structural units represented by general formula (a1-1) to (a1-4) are shown below.

[Chemical Formula 29]

(a1-1-1)
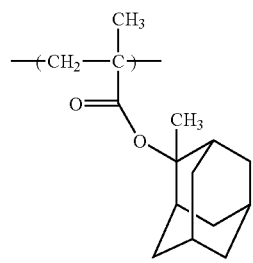

(a1-1-2)
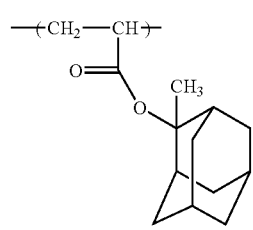

(a1-1-3)
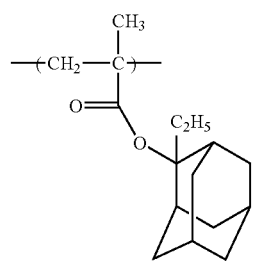

(a1-1-4)
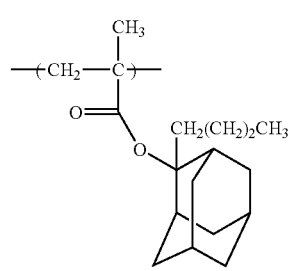

(a1-1-5)
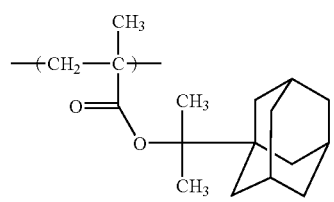

(a1-1-6)
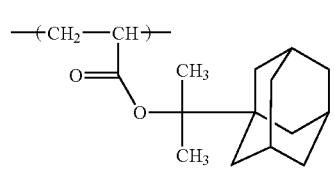

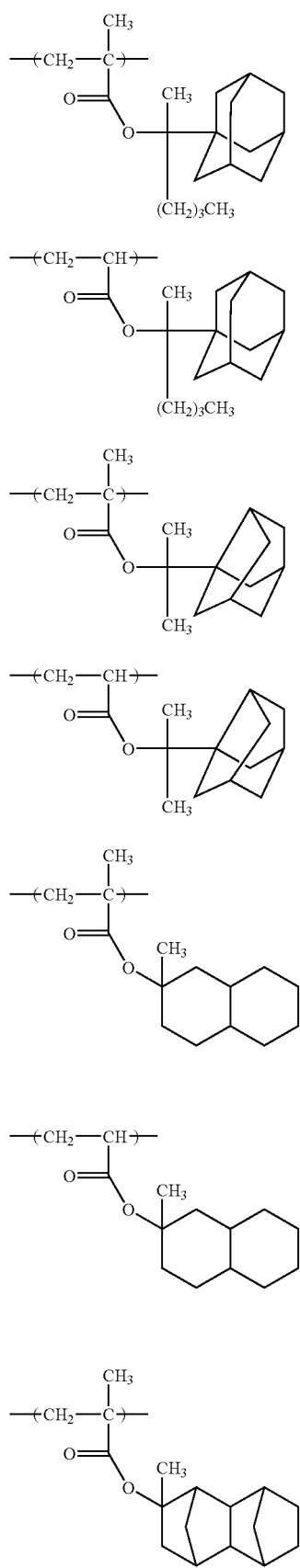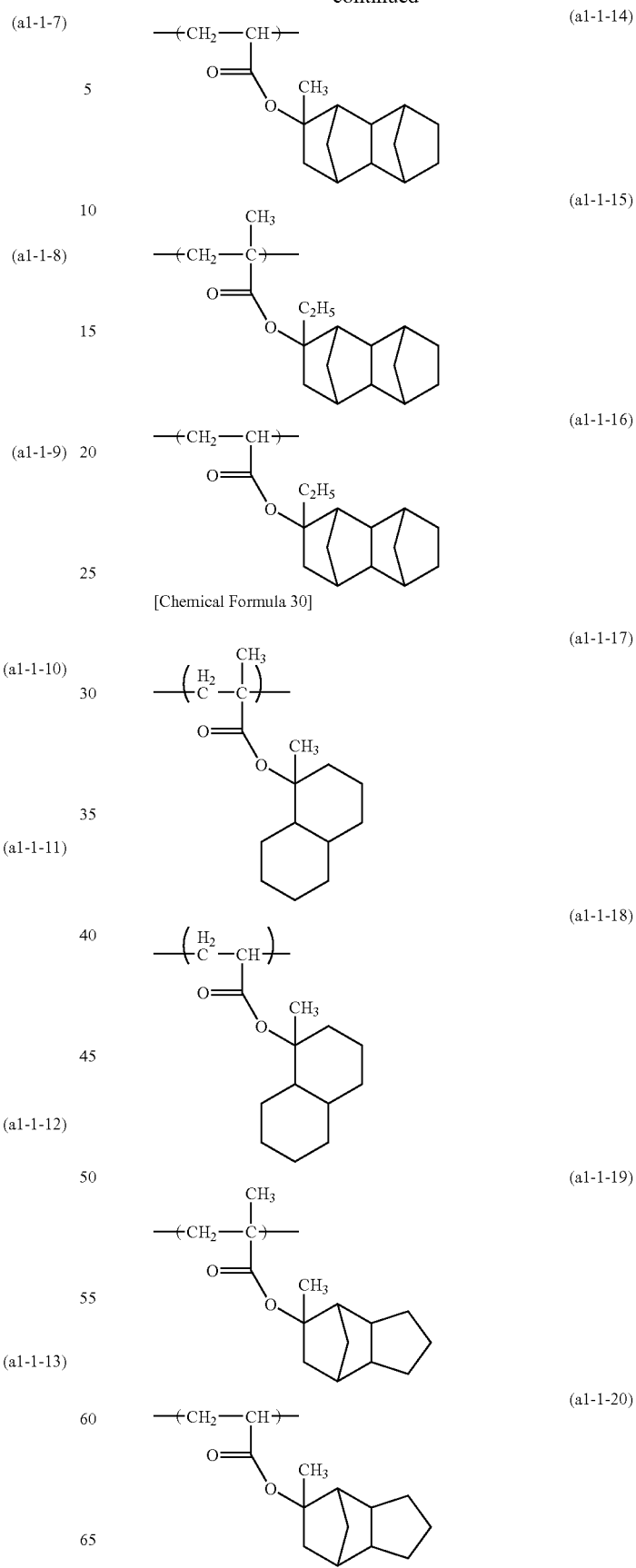

(a1-1-21) 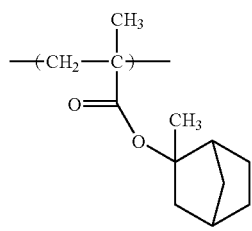
(a1-1-22) 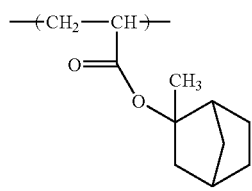
(a1-1-23) 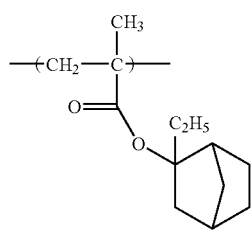
(a1-1-24) 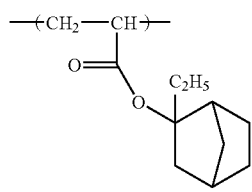
(a1-1-25) 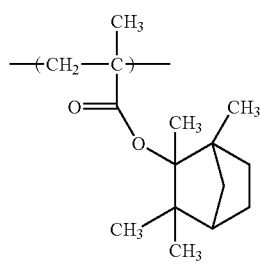
(a1-1-26) 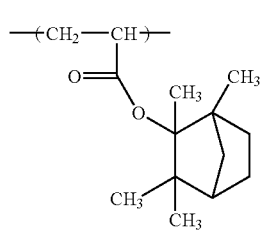
(a1-1-27) 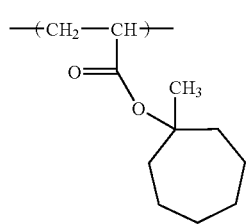
(a1-1-28) 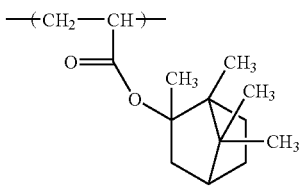
(a-1-1-29) 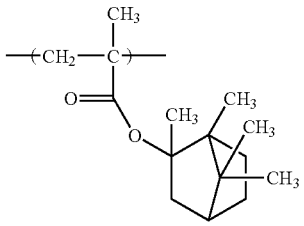
(a1-1-30) 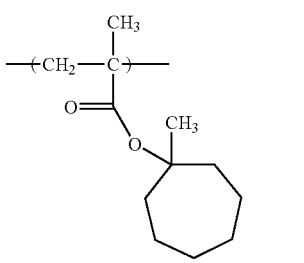
(a1-1-31) 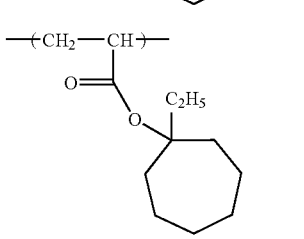
(a1-1-32) 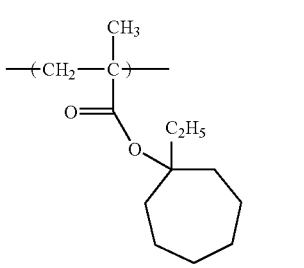
[Chemical Formula 31]
(a1-1-33) 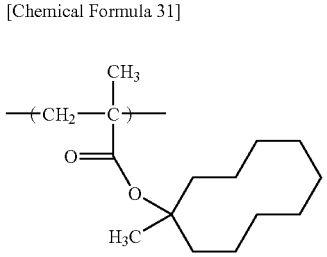
(a1-1-34) 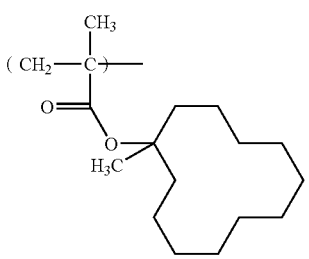

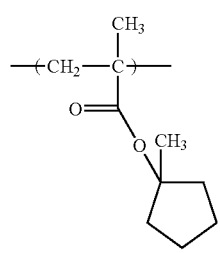 (a1-1-35)
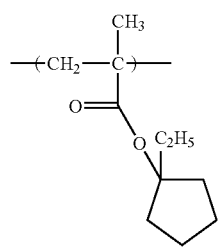 (a1-1-36)
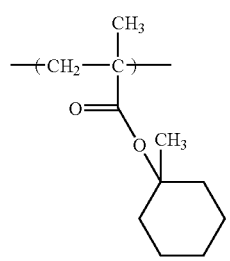 (a1-1-37)
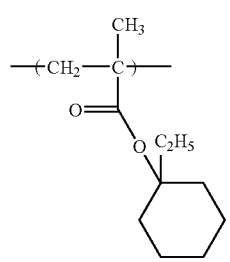 (a1-1-38)
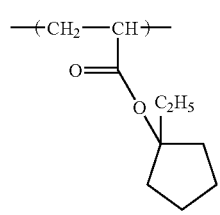 (a1-1-39)
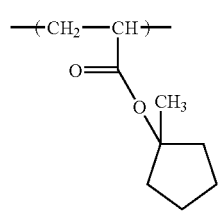 (a1-1-40)
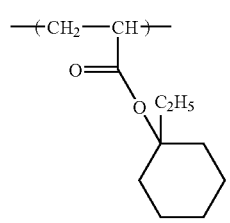 (a1-1-41)
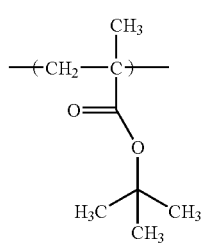 (a1-1-42)
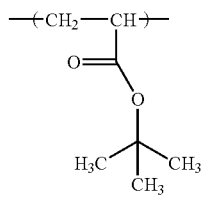 (a1-1-43)
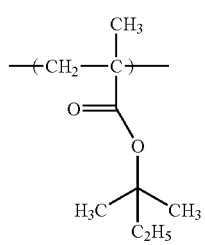 (a1-1-44)
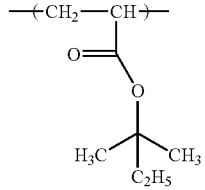 (a1-1-45)
[Chemical Formula 32]
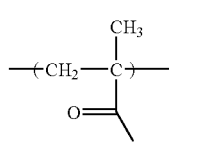 (a1-2-1)
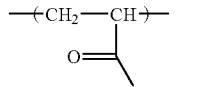 (a1-2-2)
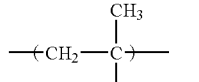 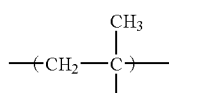 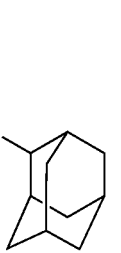 (a1-2-3)

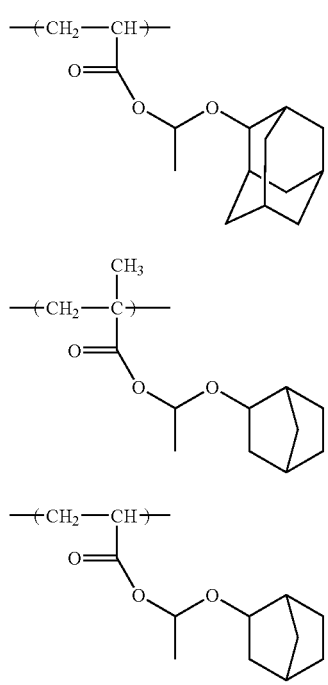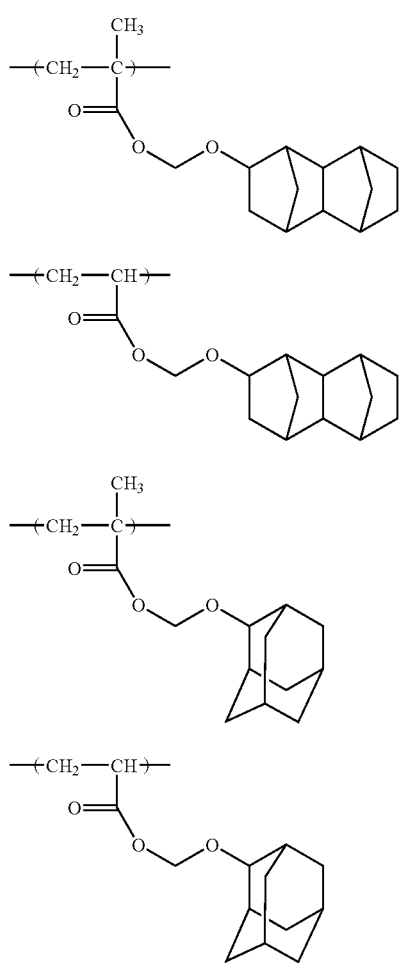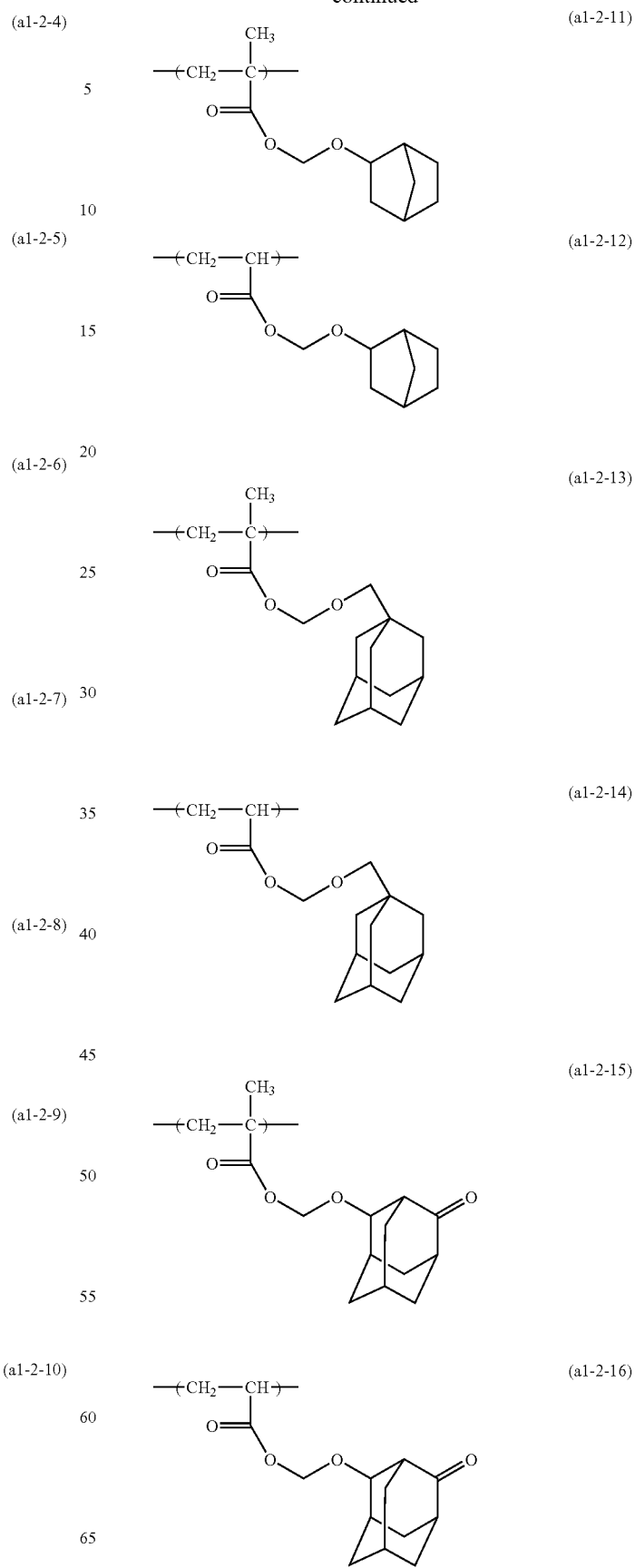

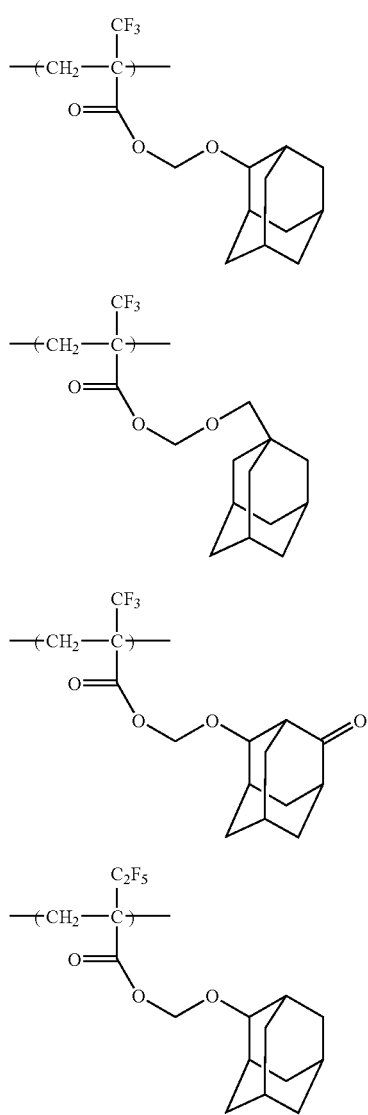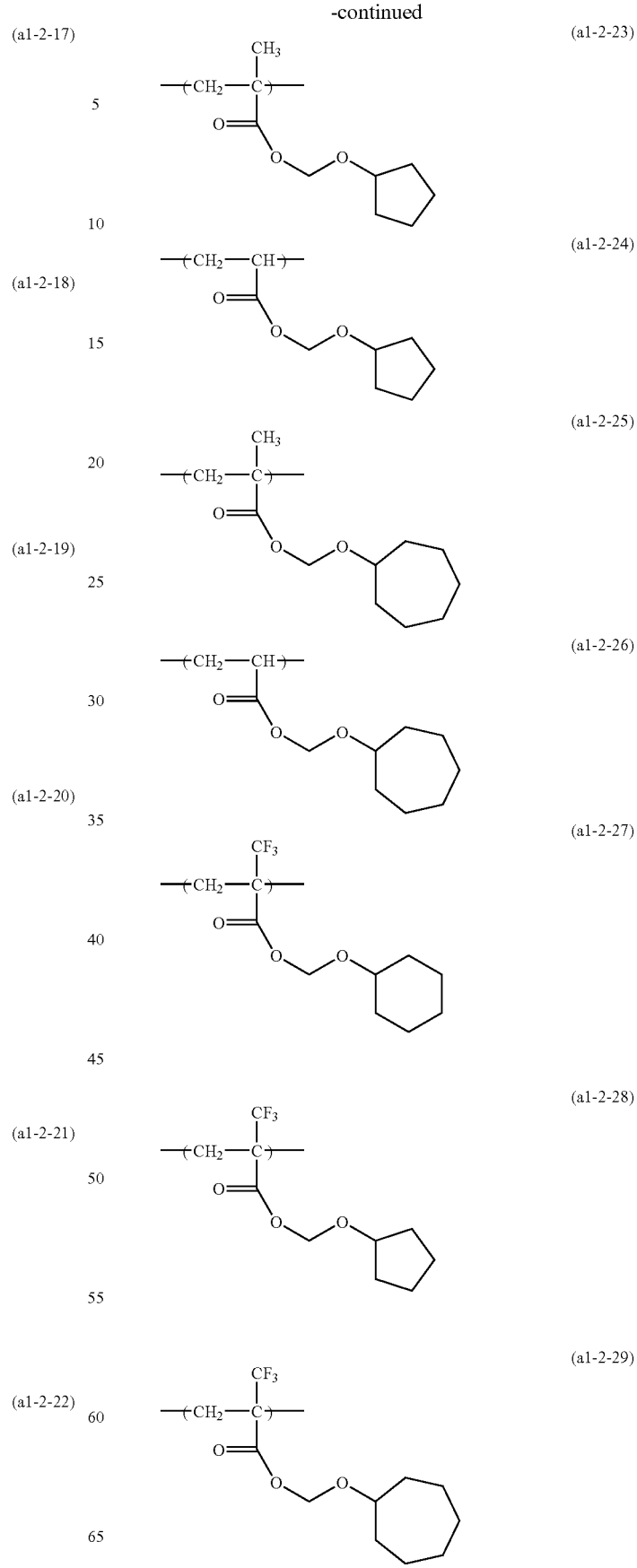

(a1-2-30)
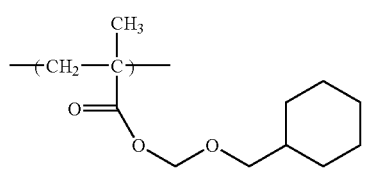
(a1-2-31)
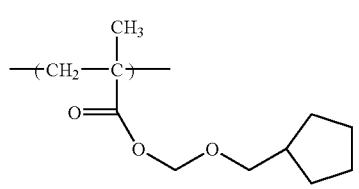
[Chemical Formula 35]
(a1-2-32)
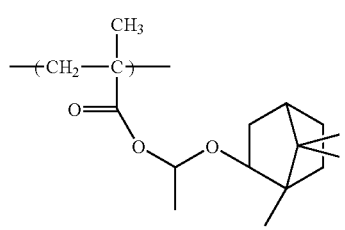
(a1-2-33)
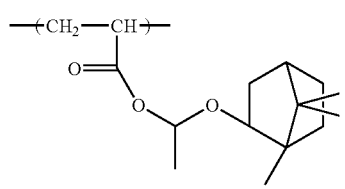
(a1-2-34)
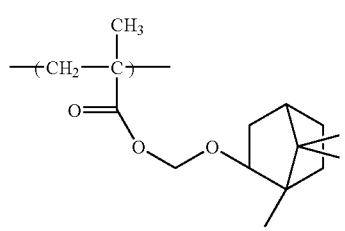
(a1-2-35)
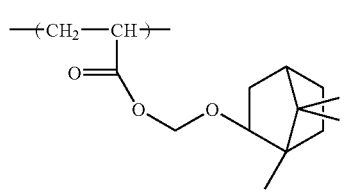
(a1-2-36)
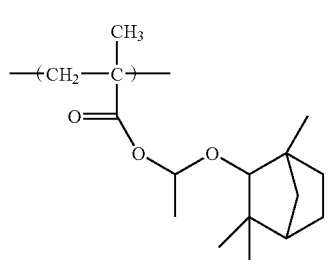
(a1-2-37)
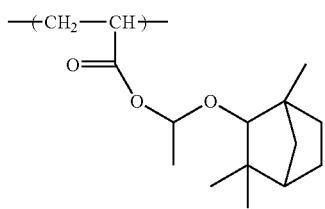
(a1-2-38)
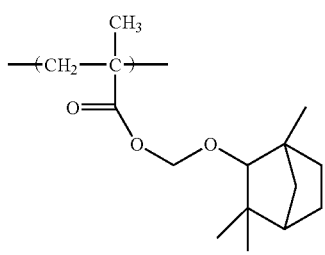
(a1-2-39)
[Chemical Formula 36]
(a1-3-1)
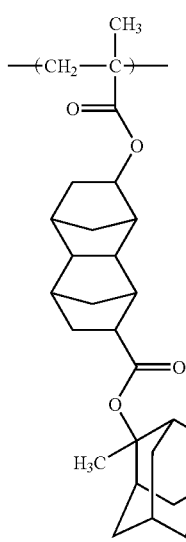

(a1-3-2) 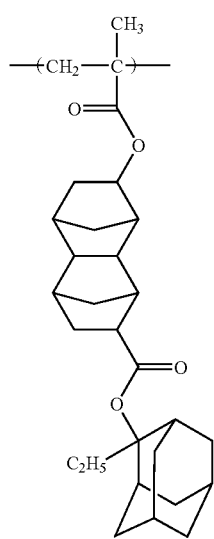
(a1-3-3) 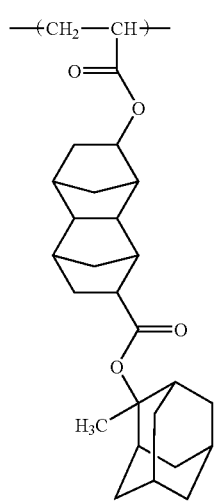
(a1-3-4) 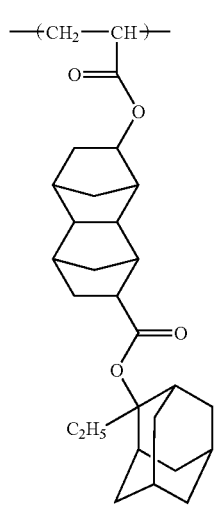
(a1-3-5) 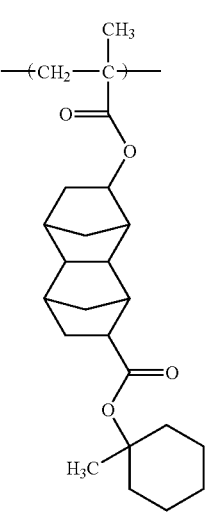
(a1-3-6) 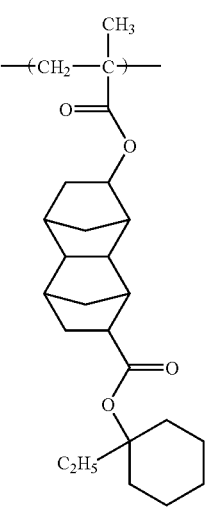
(a1-3-7) 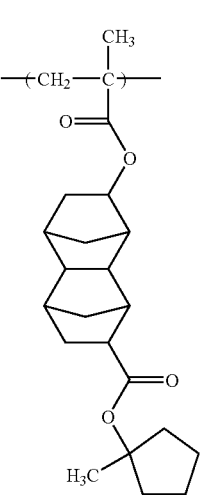

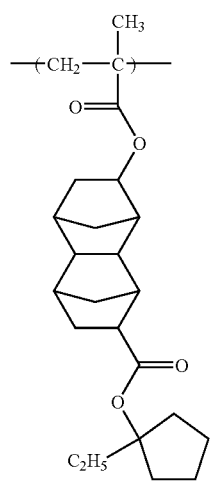 (a1-3-8)
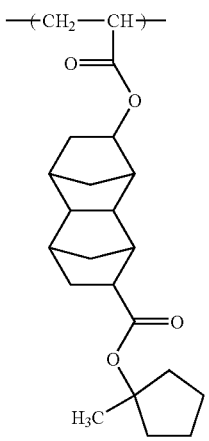 (a1-3-11)
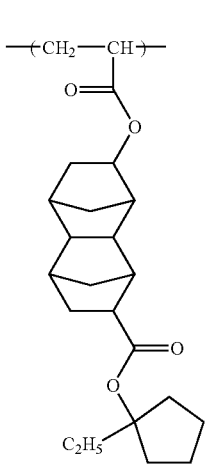 (a1-3-9)
(a1-3-12)
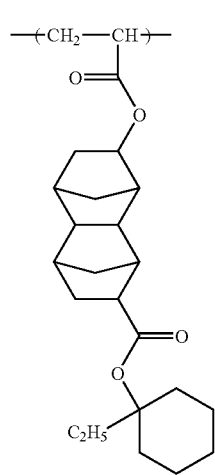 (a1-3-10)
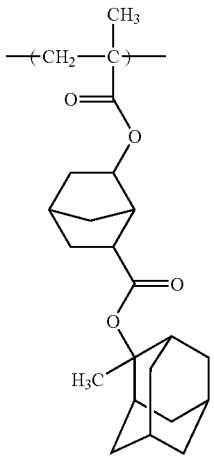 (a1-3-13)

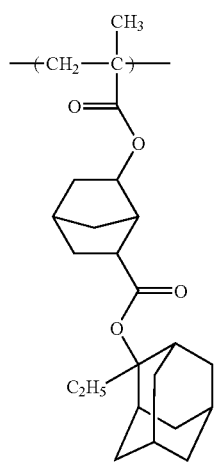 (a1-3-14)
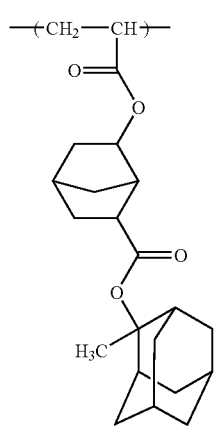 (a1-3-15)
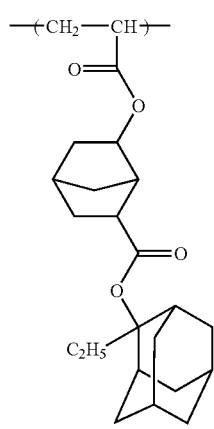 (a1-3-16)
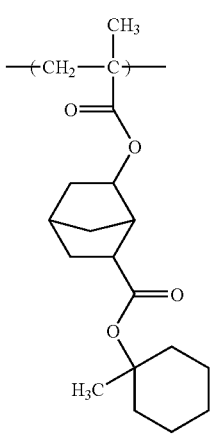 (a1-3-17)
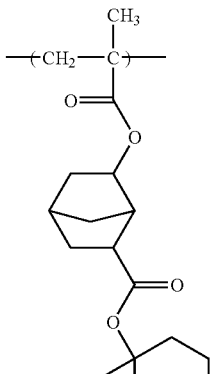 (a1-3-18)
[Chemical Formula 37]
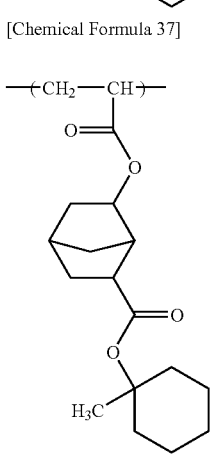 (a1-3-19)
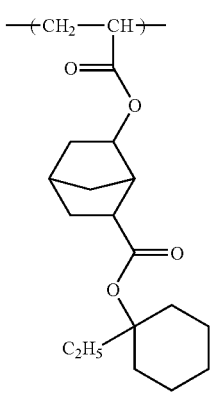 (a1-3-20)

(a1-3-21)
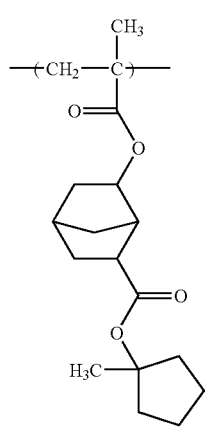
(a1-3-22)
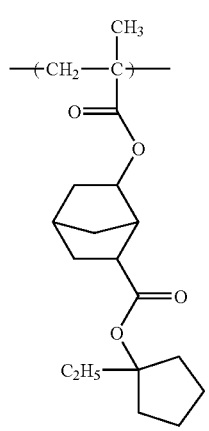
(a1-3-23)
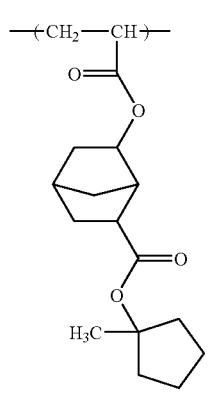
(a1-3-24)
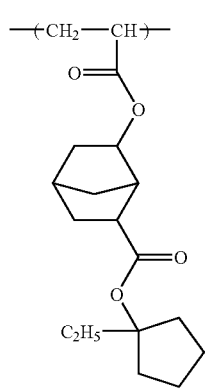
[Chemical Formula 38]
(a1-3-25)
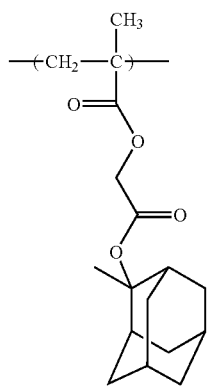
(a1-3-26)
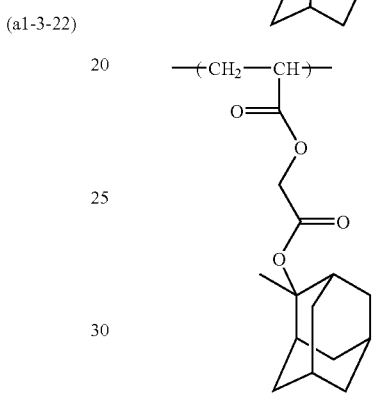
(a1-3-27)
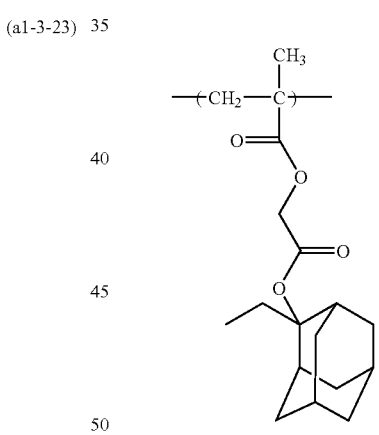
(a1-3-28)
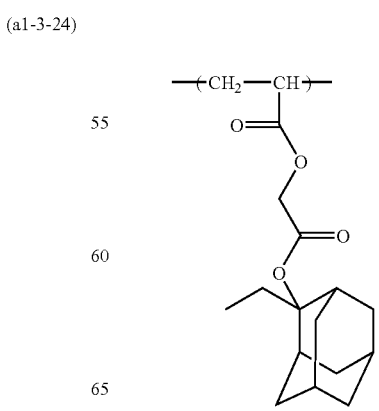

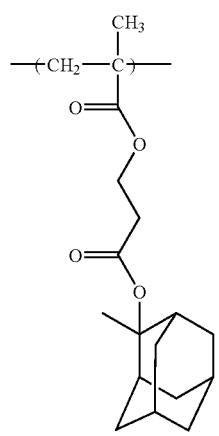 (a1-3-29)
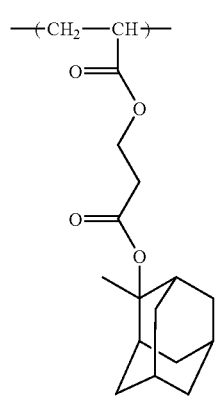 (a1-3-30)
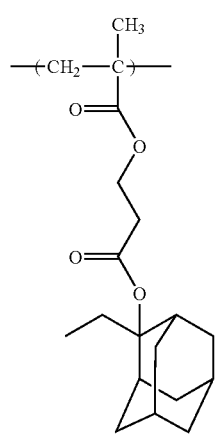 (a1-3-31)
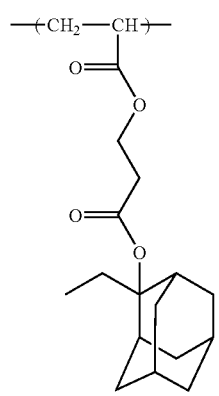 (a1-3-32)
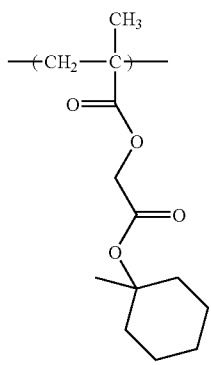 (a1-3-33)
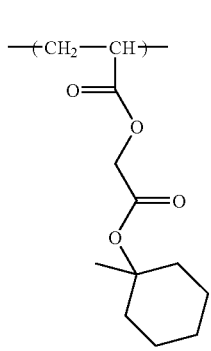 (a1-3-34)
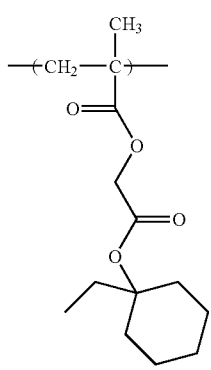 (a1-3-35)
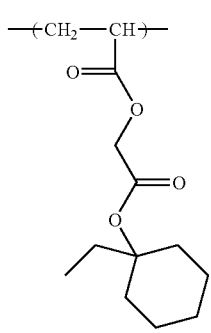 (a1-3-36)

(a1-3-37) 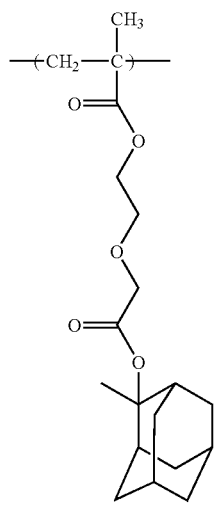
(a1-3-38) 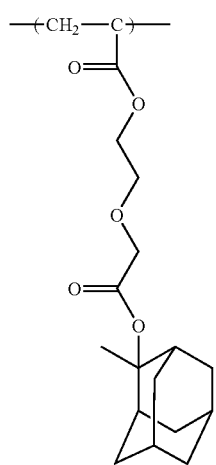
(a1-3-39) 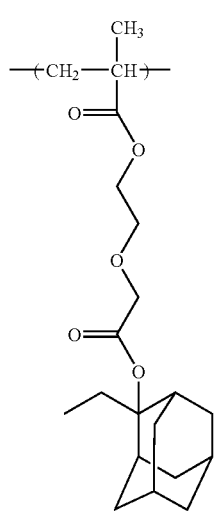
(a1-3-40) 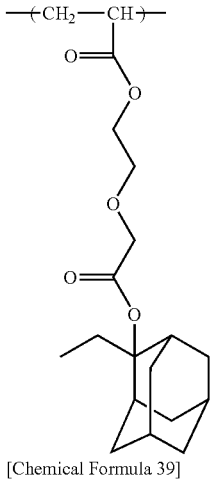
[Chemical Formula 39]
(a1-3-41) 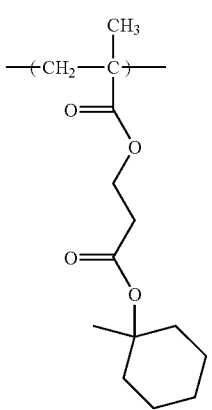
(a1-3-42) 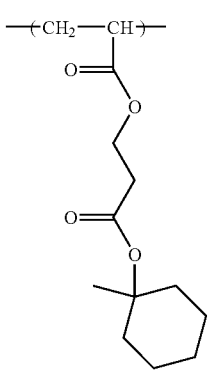
(a1-3-43) 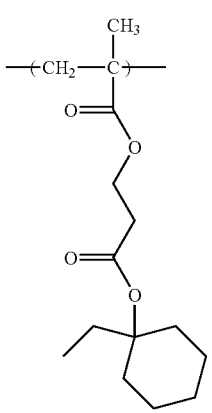

(a1-3-44) 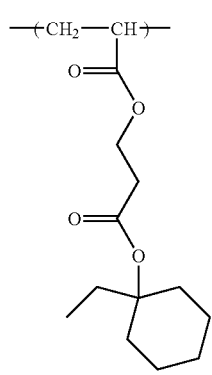
(a1-3-45) 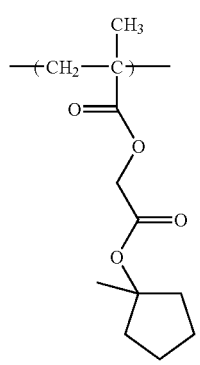
(a1-3-46) 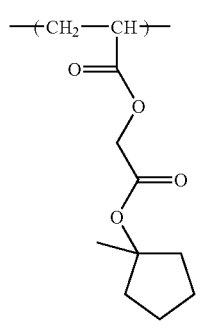
(a1-3-47) 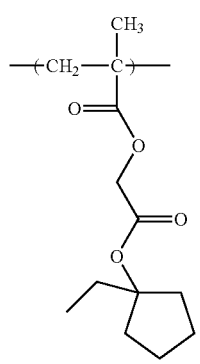
(a1-3-48) 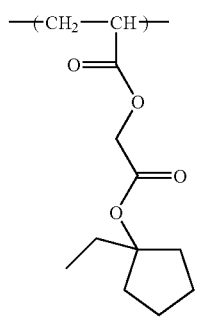
(a1-3-49) 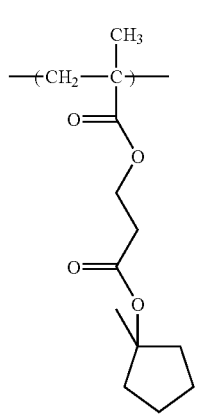
(a1-3-50) 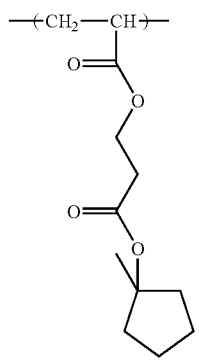
(a1-3-51) 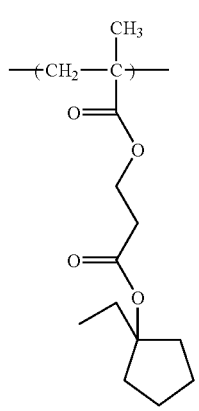

-continued
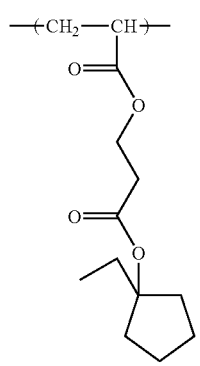
(a1-3-52)
[Chemical Formula 40]
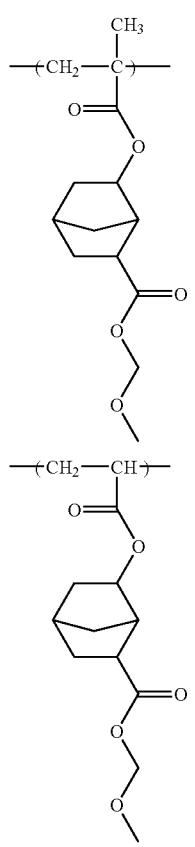
(a1-4-1)
(a1-4-2)
(a1-4-3)
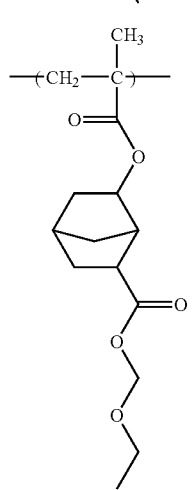
-continued
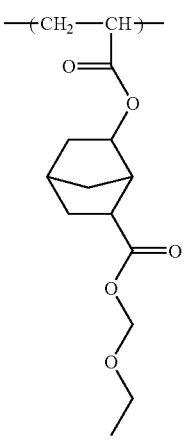
(a1-4-4)
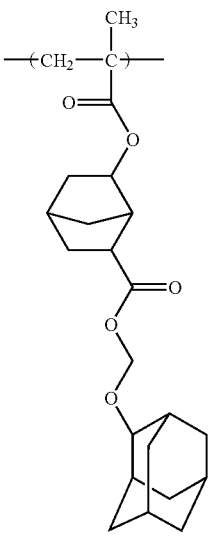
(a1-4-5)
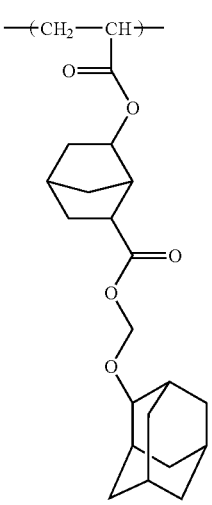
(a1-4-6)

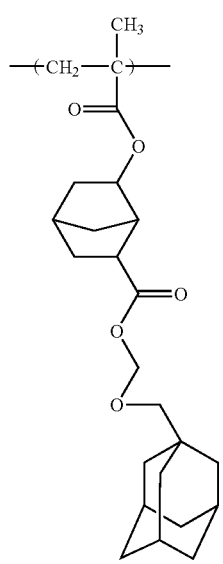
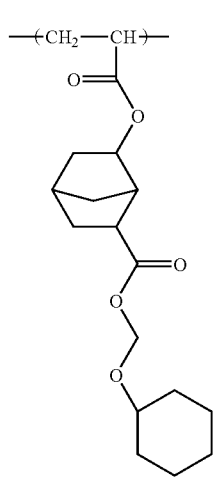

-continued
(a1-4-13)
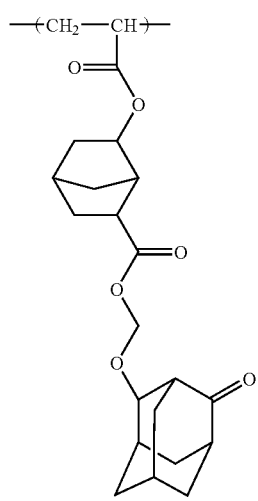
(a1-4-14)
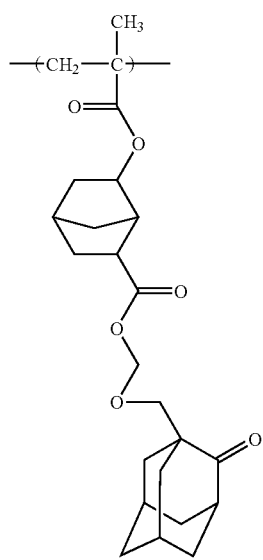
(a1-4-15)
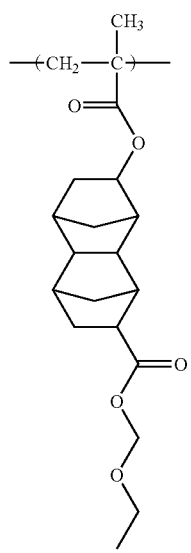
-continued
(a1-4-16)
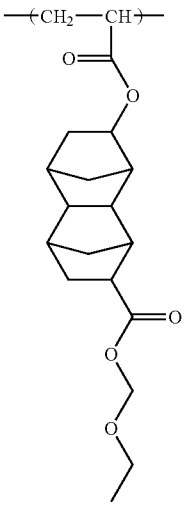
(a1-4-17)
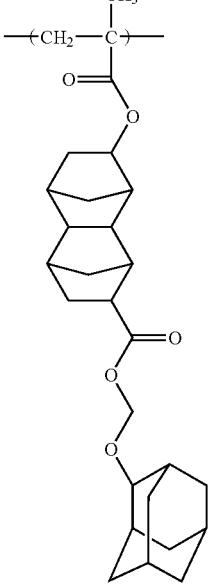
[Chemical Formula 41]
(a1-4-18)
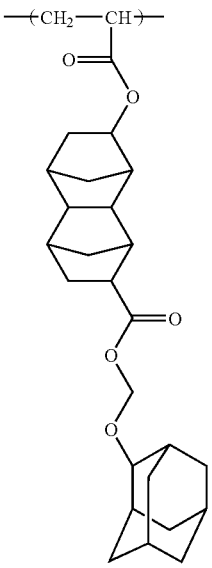

(a1-4-19) 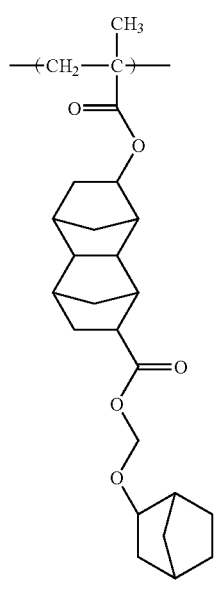
(a1-4-20) 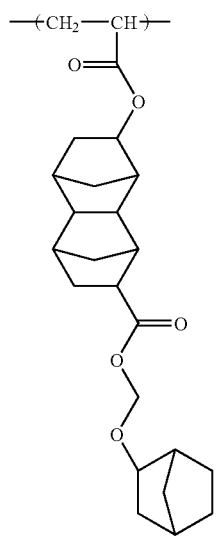
(a1-4-21) 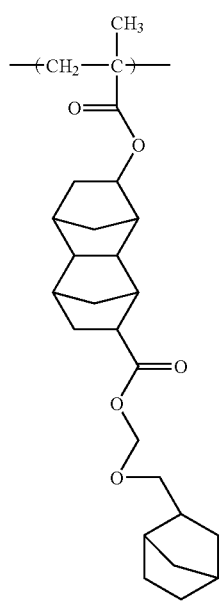
(a1-4-22) 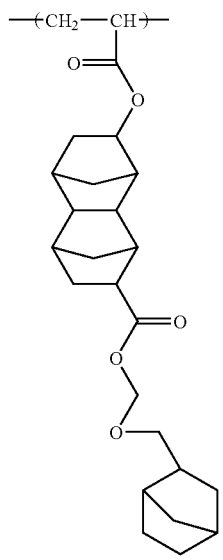
(a1-4-23) 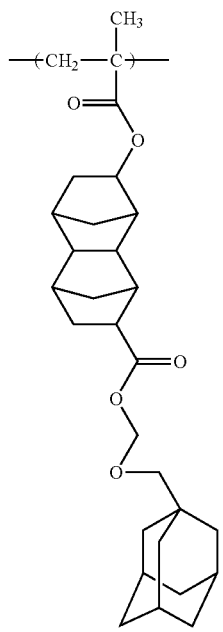

(a1-4-24)
(a1-4-25)
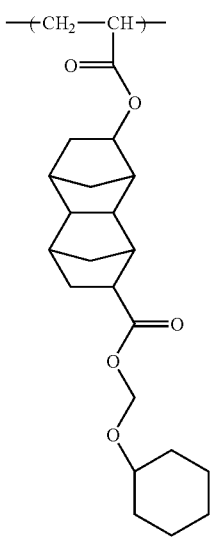
(a1-4-26)
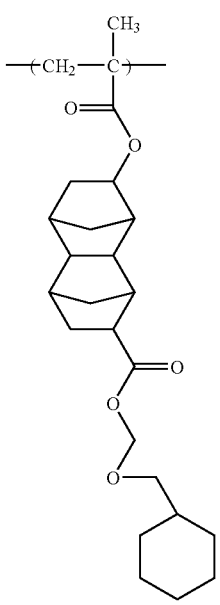
(a1-4-27)
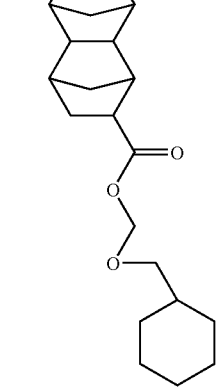
(a1-4-28)

-continued (a1-4-29)

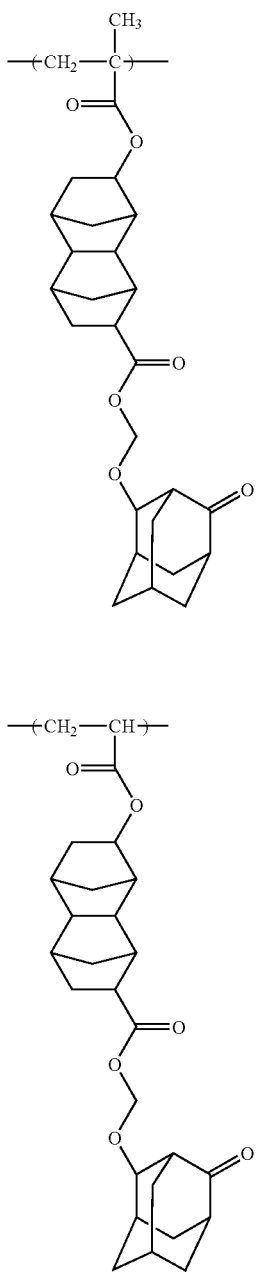

(a1-4-30)

[Chemical Formula 42]

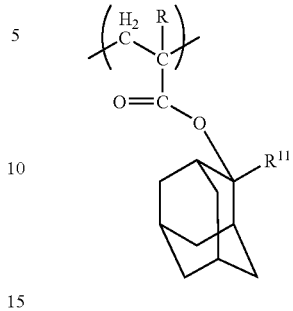

(a1-1-01)

wherein R represents a hydrogen atom, a lower alkyl group or a halogenated lower alkyl group, and $R^{11}$ represents a lower alkyl group.

[Chemical Formula 43]

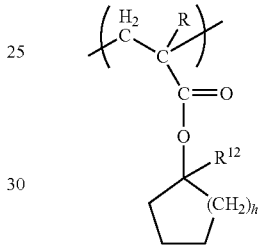

(a1-1-02)

wherein R represents a hydrogen atom, a lower alkyl group or a halogenated lower alkyl group, $R^{12}$ represents a lower alkyl group, and h represents an integer of 1 to 3.

In general formula (a1-1-01), the lower alkyl group or halogenated lower alkyl group for R is as defined above for the lower alkyl group or halogenated lower alkyl group that may be bonded to the α-position of the aforementioned acrylate ester. The lower alkyl group for $R^{11}$ is as defined for the lower alkyl group that may be bonded to the α-position of the aforementioned acrylate ester, and is preferably a methyl group or an ethyl group.

In general formula (a1-1-02), the lower alkyl group or halogenated lower alkyl group for R is as defined above for the lower alkyl group or halogenated lower alkyl group that may be bonded to the α-position of the aforementioned acrylate ester. The lower alkyl group for $R^{12}$ is as defined for the lower alkyl group that may be bonded to the α-position of the aforementioned acrylate ester. $R^{12}$ is preferably a methyl group or an ethyl group, and most preferably an ethyl group. h is preferably 1 or 2, and most preferably 2.

As the structural unit (a1), one type of unit may be used alone, or two or more types may be used in combination.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a resist composition prepared from the component (A1). On the other hand, by making the amount of the structural unit (a1) no more than the upper limit of the above-mentioned range, a good balance can be achieved with the other structural units.

Among these, structural units represented by general formula (a1-1) are preferable. More specifically, at least one structural unit selected from the group consisting of structural units represented by formulas (a1-1-1) to (a-1-1-6), (a1-1-35) to (a1-1-41), and (a1-3-31) to (a1-3-40) is particularly preferred.

Further, as the structural unit (a1), structural units represented by general formula (a1-1-01) shown below, which includes the structural units represented by formulas (a1-1-1) to (a1-1-4), and structural units represented by general formula (a1-1-02) shown below, which includes the structural units represented by formulas (a1-1-35) to (a1-1-41) are also preferable.

Structural Unit (a2)

The structural unit (a2) is a structural unit derived from an acrylate ester that contains a lactone-containing cyclic group.

The term "lactone-containing cyclic group" refers to a cyclic group including one ring containing a —O—C(O)— structure (namely, a lactone ring). The lactone ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility, with the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below,

[Chemical Formula 44]

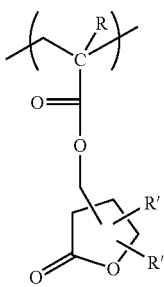
(a2-1)

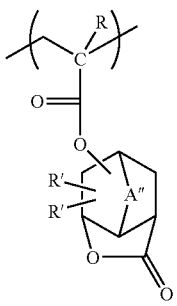
(a2-2)

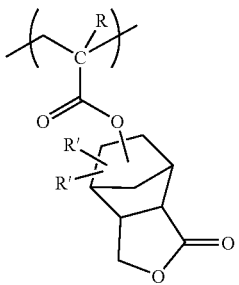
(a2-3)

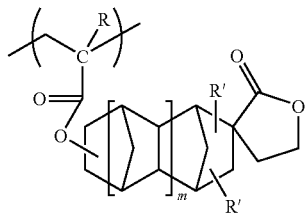
(a2-4)

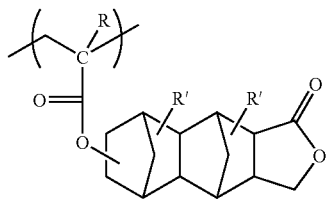
(a2-5)

wherein R represents a hydrogen atom, a lower alkyl group or a halogenated lower alkyl group; R' represents a hydrogen atom, a lower alkyl group, an alkoxy group of 1 to 5 carbon atoms or —COOR", wherein R" represents a hydrogen atom or a linear, branched or cyclic alkyl group of 1 to 15 carbon atoms; m represents 0 or 1; and A" represents an alkylene group of 1 to 5 carbon atoms that may include an oxygen atom or a sulfur atom, an oxygen atom, or a sulfur atom.

In general formulas (a2-1) to (a2-5), R is as defined for R in the structural unit (a1).

The lower alkyl group for R' is as defined for the lower alkyl group for R in the structural unit (a1).

When R" is a linear or branched alkyl group, R" preferably has 1 to 10 carbon atoms, and more preferably 1 to 5 carbon atoms.

When R" is a cyclic alkyl group, R" preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

In the structural units represented by general formulas (a2-1) to (a2-5), in consideration of factors such as industrial availability, R' is preferably a hydrogen atom.

Specific examples of the alkylene group of 1 to 5 carbon atoms that may include an oxygen atom or a sulfur atom for A" include a methylene group, ethylene group, n-propylene group, isopropylene group, —O—CH$_2$—, —CH$_2$—O—CH$_2$—, —S—CH$_2$—, and —CH$_2$—S—CH$_2$—.

Specific examples of structural units represented by general formulas (a2-1) to (a2-5) above are shown below.
[Chemical Formula 45]
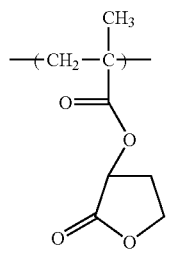
(a2-1-1)
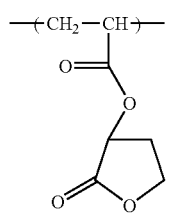
(a2-1-2)
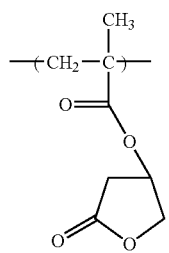
(a2-1-3)
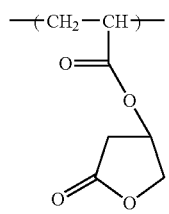
(a2-1-4)
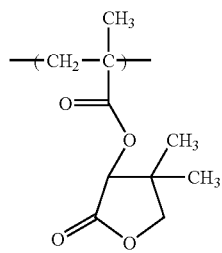
(a2-1-5)
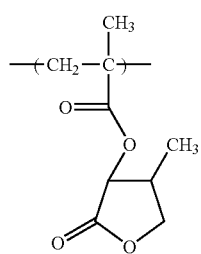
(a2-1-6)
[Chemical Formula 46]
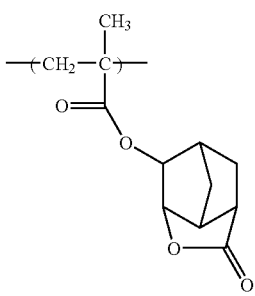
(a2-2-1)
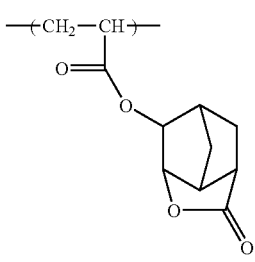
(a2-2-2)
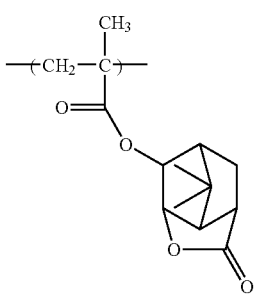
(a2-2-3)
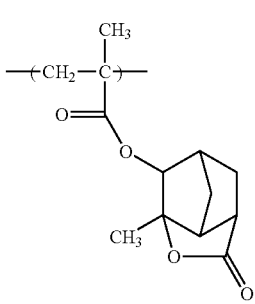
(a2-2-4)
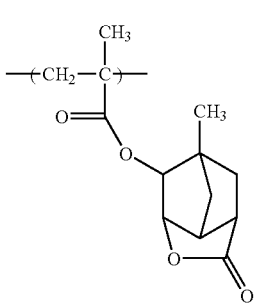
(a2-2-5)

(a2-2-6)
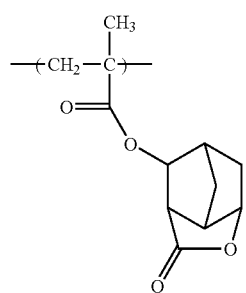
(a2-2-7)
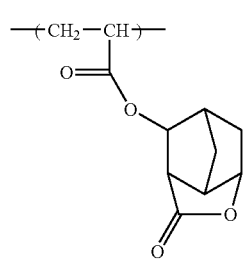
(a2-2-8)
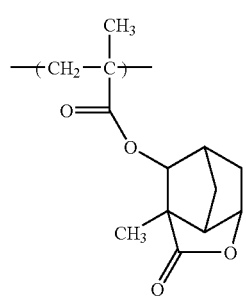
(a2-2-9)
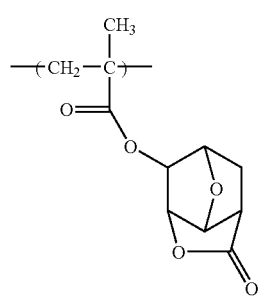
(a2-2-10)
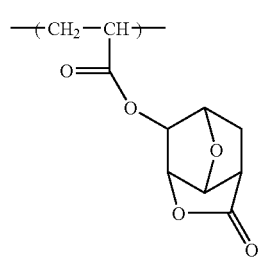
(a2-2-11)
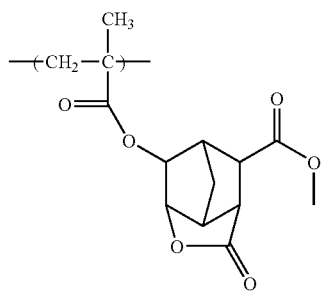
(a2-2-12)
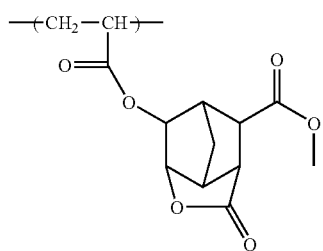
(a2-2-13)
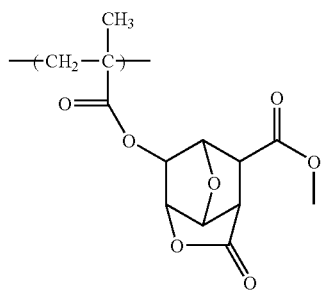
(a2-2-14)
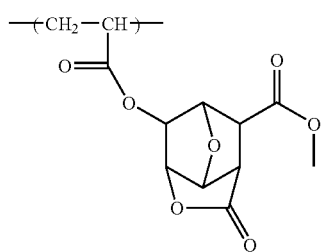
[Chemical Formula 47]
(a2-3-1)
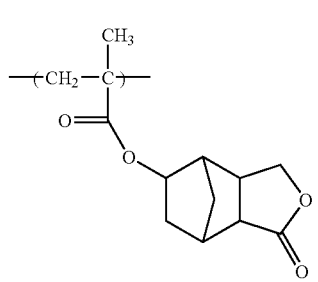
(a2-3-2)
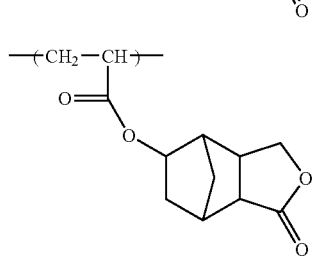

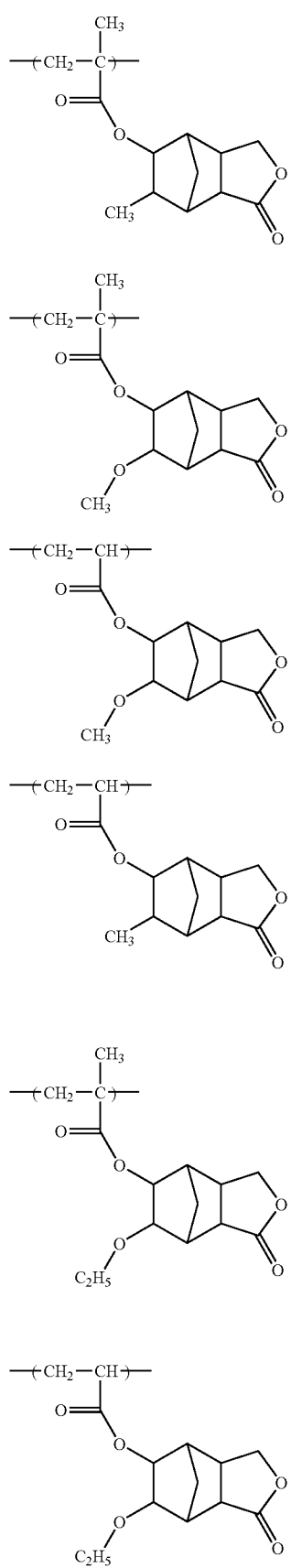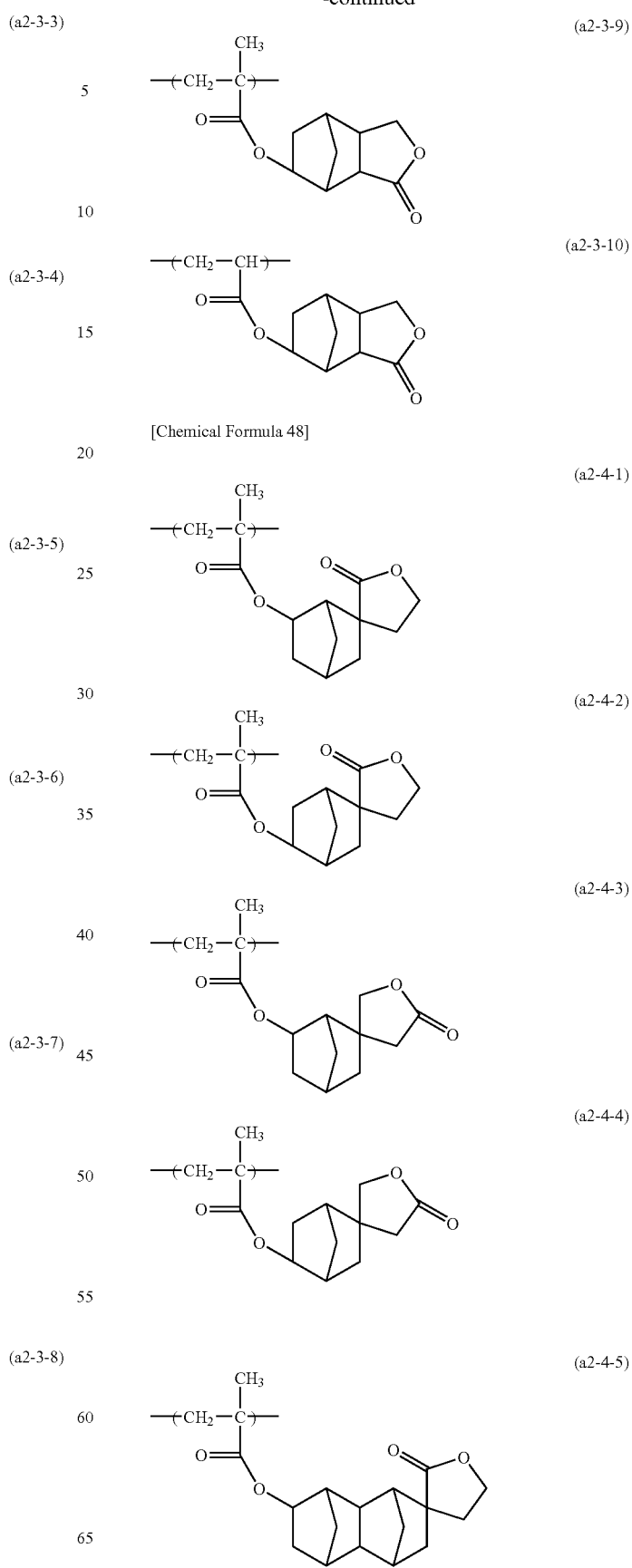

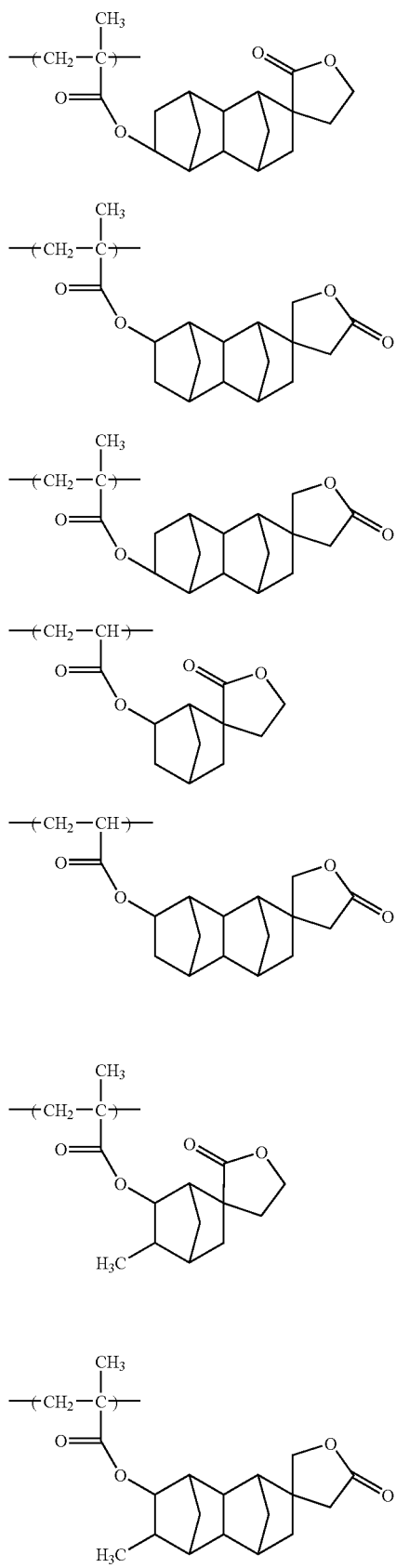

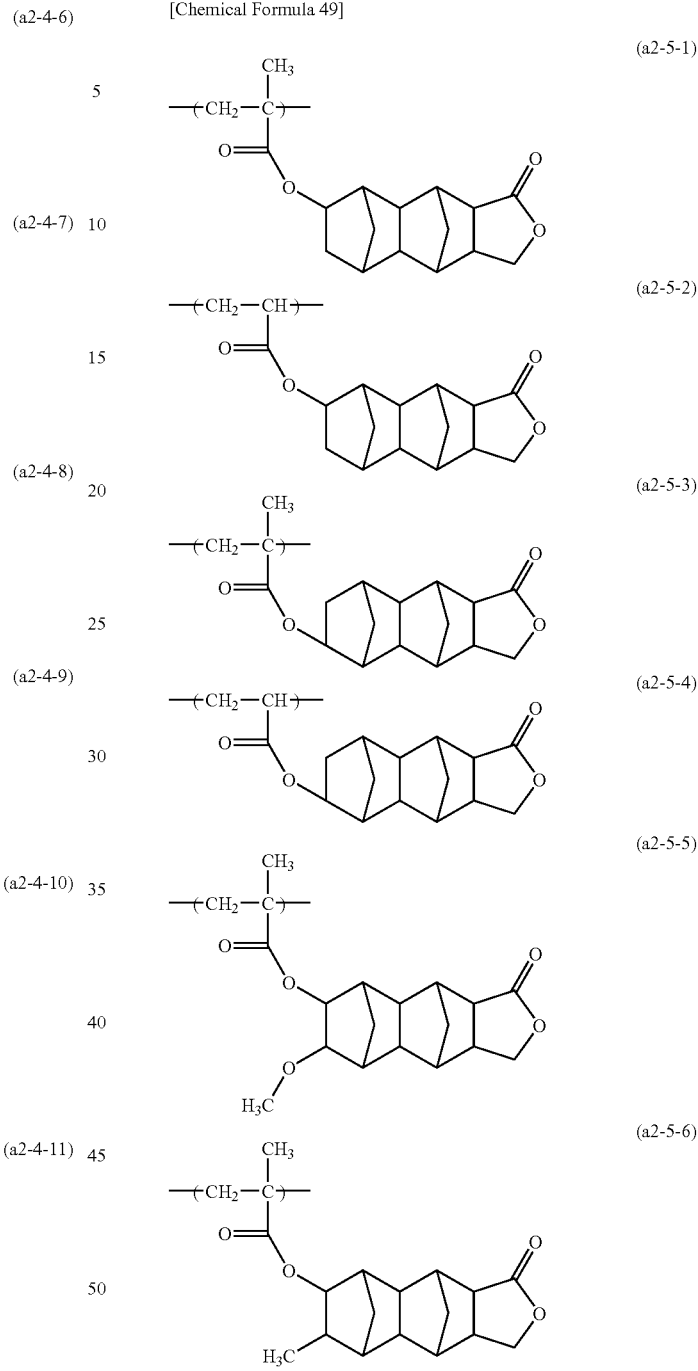

As the structural unit (a2), at least one structural unit selected from the group consisting of general formulas (a2-1) to (a2-5) is preferable, and at least one structural unit selected from the group consisting of general formulas (a2-1) to (a2-3) is more preferable. Specifically, it is preferable to use at least one structural unit selected from the group consisting of formulas (a2-1-1), (a2-1-2), (a2-2-1), (a2-2-2), (a2-2-9), (a2-2-10), (a2-3-1), (a2-3-2), (a2-3-9) and (a2-3-10).

In the component (A1), as the structural unit (a2), either one type of structural unit may be used alone, or two or more types may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

Structural Unit (a3)

The structural unit (a3) is a structural unit derived from an acrylate ester that contains a polar group-containing aliphatic hydrocarbon group.

When the component (A1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that includes an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane or tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 50]

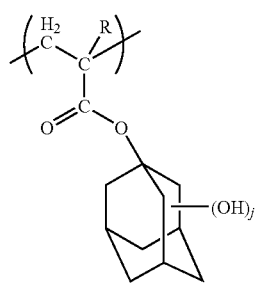

(a3-1)

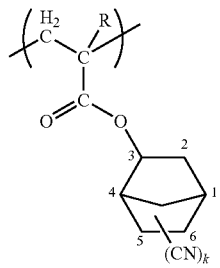

(a3-2)

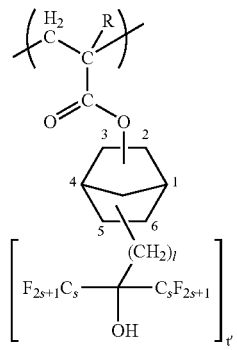

(a3-3)

wherein R is as defined above for R in the structural unit (a1), j is an integer of 1 to 3, k is an integer of 1 to 3, t' is an integer of 1 to 3, l is an integer of 1 to 5, and s is an integer of 1 to 3.

In formula (a3-1), j is preferably 1 or 2, and more preferably 1. When j is 2, it is preferable that the hydroxyl groups are bonded to the 3rd and 5th positions of the adamantyl group. When j is 1, it is preferable that the hydroxyl group is bonded to the 3rd position of the adamantyl group.

j is preferably 1, and it is particularly desirable that the hydroxyl group is bonded to the 3rd position of the adamantyl group.

In formula (a3-2), k is preferably 1. The cyano group is preferably bonded to the 5th or 6th position of the norbornyl group.

In formula (a3-3), t' is preferably 1, l is preferably 1 and s is preferably 1. Further, in formula (a3-3), it is preferable that a 2-norbornyl group or 3-norbornyl group is bonded to the terminal of the carboxyl group of the acrylic acid. The fluorinated alkyl alcohol is preferably bonded to the 5th or 6th position of the norbornyl group.

As the structural unit (a3), one type of structural unit may be used alone, or two or more types may be used in combination.

In the component (A1), the amount of the structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit derived from an acrylate ester that contains a non-acid-dissociable aliphatic polycyclic group is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to carbon atoms.

Specific examples of the structural unit (a4) include units with structures represented by general formulas (a4-1) to (a4-5) shown below.

[Chemcial Formula 51]

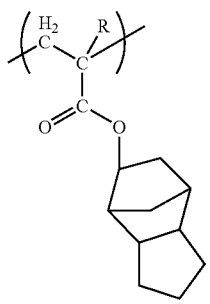
(a4-1)

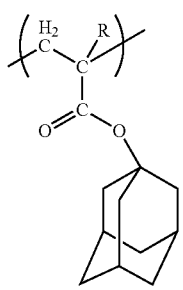
(a4-2)

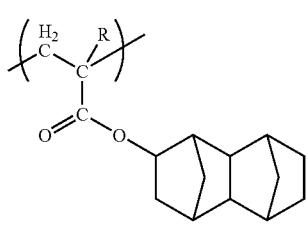
(a4-3)

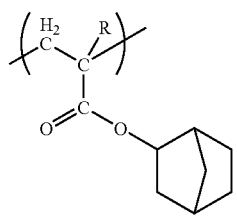
(a4-4)

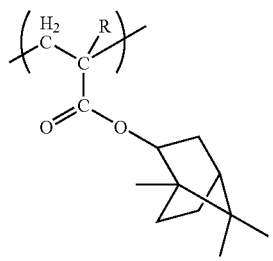
(a4-5)

wherein R is as defined above for R in the structural unit (a1).

When the structural unit (a4) is included in the component (A1), the amount of the structural unit (a4) based on the combined total of all the structural units that constitute the component (A1) is preferably within a range from 1 to 30 mol %, and more preferably from 10 to 20 mol %.

In the present invention, the component (A1) is a resin component (polymer) that exhibits increased solubility in an alkali developing solution under the action of acid. An example of a preferred form of this resin component (polymer) is a copolymer having the structural units (a1), (a2) and (a3). Examples of such a copolymer include a copolymer consisting of solely the structural units (a1) and (a2) and (a3), and a copolymer consisting of the structural units (a1), (a2), (a3) and (a4).

In the present invention, a copolymer (A1-1) that includes a combination of structural units such as that shown below in general formula (A1-1) is particularly preferred as the component (A1).

[Chemical Formula 52]

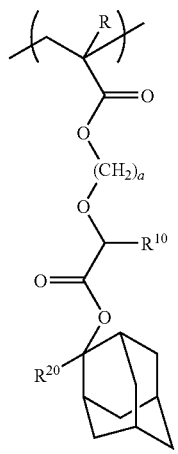
(A1-1)

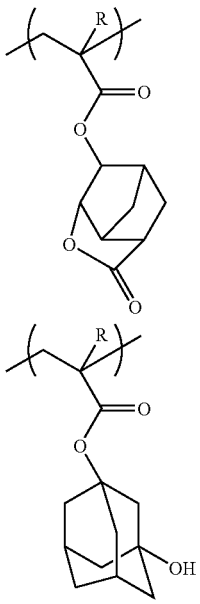

wherein each R is as defined above for R in the structural unit (a1), although the plurality of R groups may be the same or different, $R^{10}$ represents a hydrogen atom or a lower alkyl group, $R^{20}$ represents a lower alkyl group, and a is an integer of 1 to 3.

In formula (A1-1), R is as defined above for R in the structural unit (a1), and is preferably a hydrogen atom or a methyl group.

$R^{10}$ represents a hydrogen atom or a lower alkyl group, and is most preferably a hydrogen atom. When $R^{10}$ represents a lower alkyl group, the lower alkyl group is as defined above for the lower alkyl group for R in the structural unit (a1), is preferably a methyl group or ethyl group, and is most preferably a methyl group.

$R^{20}$ represents a lower alkyl group, which is as defined for the lower alkyl group for R in the structural unit (a1), is preferably a methyl group or ethyl group, and is most preferably a methyl group.

a represents an integer of 1 to 3, is preferably 1 or 2, and is most preferably 2.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having an introduced hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By making the weight average molecular weight no more than the upper limit of the above-mentioned range, the component (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A2)]

As the component (A2), it is preferable to use a compound that has a molecular weight of at least 500 and less than 2,000, contains a hydrophilic group, and also contains an acid-dissociable, dissolution-inhibiting group such as those exemplified above in connection with the component (A1). Specific examples include compounds containing a plurality of phenol structures in which some of the hydrogen atoms within the hydroxyl groups have been substituted with the aforementioned acid dissociable, dissolution-inhibiting groups.

Examples of the component (A2) include low molecular weight phenolic compounds in which a portion of hydrogen atoms of the hydroxyl group have been substituted with an aforementioned acid-dissociable, dissolution-inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid-dissociable, dissolution-inhibiting group, and suitable examples include the groups described above.

As the component (A), one type of component may be used alone, or two or more types may be used in combination.

In the resist composition of the present invention, the amount of the component (A) can be appropriately adjusted depending on factors such as the thickness of the resist film to be formed.

<Component (B)>

The component (B) includes an acid generator (B1) (hereafter, referred to as "component (B1)") consisting of a compound represented by general formula (b1-2) above. The component (B1) is the same as the compound (B1) of the present invention described above.

As the component (B1), one type may be used, or two or more types may be used in combination.

In the resist composition of the present invention, the amount of the component (B1) within the component (B) is preferably 40% by weight or more, more preferably 70% by weight or more, and may be even 100% by weight. It is particularly desirable that the amount of the component (B1)

within the component (B) is 100% by weight. By making the amount of the component (B1) at least as large as the lower limit of the above-mentioned range, lithography properties such as the resolution, mask reproducibility, and line width roughness (LWR) are improved when a resist pattern is formed using the resist composition of the present invention.

In the component (B), an acid generator (B2) other than the aforementioned component (B1) (hereafter, referred to as "component (B2)") may be used in combination with the component (B1), provided the effects of the present invention are not impaired.

As the component (B2), there is no particular limitation as long as it is an acid generator other than the component (B1), and any of the known acid generators used in conventional chemically amplified resist compositions can be used.

Examples of these acid generators are numerous, and include onium salt-based acid generators such as iodonium salts and sulfonium salts, oxime sulfonate-based acid generators, diazomethane-based acid generators such as bisalkyl or bisaryl sulfonyl diazomethanes and poly(bis-sulfonyl)diazomethanes, nitrobenzylsulfonate-based acid generators, iminosulfonate-based acid generators, and disulfone-based acid generators.

As the onium salt-based acid generator, a compound represented by general formula (b-1) or (b-2) shown below can be used.

[Chemical Formula 53]

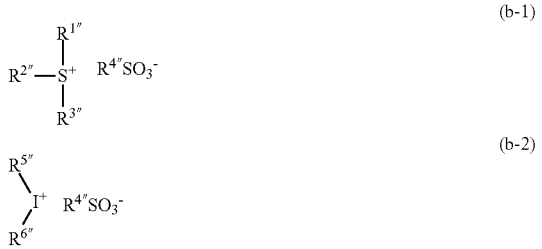

wherein $R^{1\prime\prime}$ to $R^{3\prime\prime}$, and $R^{5\prime\prime}$ and $R^{6\prime\prime}$ each independently represents an aryl group or alkyl group, wherein two of $R^{1\prime\prime}$ to $R^{3\prime\prime}$ in formula (b-1) may be bonded to each other to form a ring with the sulfur atom in the formula; and $R^{4\prime\prime}$ represents a linear, branched or cyclic alkyl group or fluorinated alkyl group; with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. In formula (b-1), two of $R^{1\prime\prime}$ to $R^{3\prime\prime}$ may be bonded to each other to form a ring with the sulfur atom in the formula.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group having 6 to 20 carbon atoms may be used, in which some or all of the hydrogen atoms of the aryl group may or may not be substituted with alkyl groups, alkoxy groups, halogen atoms or hydroxyl groups. The aryl group is preferably an aryl group having 6 to 10 carbon atoms because it can be synthesized at a low cost. Specific examples thereof include a phenyl group or a naphthyl group.

The alkyl group with which hydrogen atoms of the aryl group may be substituted is preferably an alkyl group having 1 to 5 carbon atoms, and most preferably a methyl group, ethyl group, propyl group, n-butyl group, or tert-butyl group.

The alkoxy group with which hydrogen atoms of the aryl group may be substituted is preferably an alkoxy group having 1 to 5 carbon atoms, and most preferably a methoxy group, ethoxy group, n-propoxy group, iso-propoxy group, n-butoxy group or tert-butoxy group.

The halogen atom with which hydrogen atoms of the aryl group may be substituted is preferably a fluorine atom.

The alkyl group for $R^{1\prime\prime}$ to $R^{3\prime\prime}$ is not particularly limited, and examples thereof include linear, branched or cyclic alkyl groups having 1 to 10 carbon atoms. In terms of achieving excellent resolution, the alkyl group preferably has 1 to 5 carbon atoms. Specific examples thereof include a methyl group, ethyl group, n-propyl group, isopropyl group, n-butyl group, isobutyl group, n-pentyl group, cyclopentyl group, hexyl group, cyclohexyl group, nonyl group and decanyl group, and a methyl group is most preferable because it yields excellent resolution and can be synthesized at a low cost.

It is particularly desirable that each of $R^{1\prime\prime}$ to $R^{3\prime\prime}$ is a phenyl group or a naphthyl group.

When two of $R^{1\prime\prime}$ to $R^{3\prime\prime}$ in formula (b-1) are bonded to each other to form a ring with the sulfur atom in the formula, it is preferable that the two of $R^{1\prime\prime}$ to $R^{3\prime\prime}$ form a 3- to 10-membered ring including the sulfur atom, and it is particularly desirable that the two of $R^{1\prime\prime}$ to $R^{3\prime\prime}$ form a 5- to 7-membered ring including the sulfur atom.

When two of $R^{1\prime\prime}$ to $R^{3\prime\prime}$ in formula (b-1) are bonded to each other to form a ring with the sulfur atom in the formula, the remaining one of $R^{1\prime\prime}$ to $R^{3\prime\prime}$ is preferably an aryl group. Examples of the aryl group include the same groups as those exemplified above for the aryl groups for $R^{1\prime\prime}$ to $R^{3\prime\prime}$.

$R^{4\prime\prime}$ represents a linear, branched or cyclic alkyl group or fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group such as that described for $R^{1\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (the percentage of fluorine atoms within the alkyl group) is preferably from 10 to 100% and more preferably from 50 to 100%, and a fluorinated alkyl group in which all of the hydrogen atoms are substituted with fluorine atoms (namely, a perfluoroalkyl group) is particularly desirable because the acid strength increases.

$R^{4\prime\prime}$ is most preferably a linear or cyclic alkyl group, or a fluorinated alkyl group.

In formula (b-2), $R^{5\prime\prime}$ and $R^{6\prime\prime}$ each independently represents an aryl group or an alkyl group. At least one of $R^{5\prime\prime}$ and $R^{6\prime\prime}$ represents an aryl group. It is preferable that both of $R^{5\prime\prime}$ and $R^{6\prime\prime}$ represent aryl groups.

As the aryl group for $R^{5\prime\prime}$ and $R^{6\prime\prime}$, the same groups as the aryl groups for $R^{1\prime\prime}$ to $R^{3\prime\prime}$ in formula (b-1) can be exemplified.

As the alkyl group for $R^{5\prime\prime}$ and $R^{6\prime\prime}$, the same groups as the alkyl groups for $R^{1\prime\prime}$ to $R^{3\prime\prime}$ in formula (b-1) can be exemplified.

It is particularly desirable that both of $R^{5\prime\prime}$ and $R^{6\prime\prime}$ represent phenyl groups.

Examples of $R^{4''}$ in formula (b-2) include the same groups as those exemplified above for $R^{4''}$ in formula (b-1).

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (and in which the cation moiety is the same as (b-1) or (b-2)) may also be used.

[Chemical Formula 54]

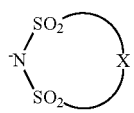

(b-3)

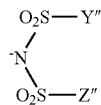

(b-4)

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, wherein the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, wherein the alkyl group has 1 to 10 carbon atoms, preferably 1 to 7 carbon atoms, and most preferably 1 to 3 carbon atoms.

The smaller the number of carbon atoms within the above-mentioned ranges for the alkylene group for X" or the alkyl group for Y" and Z", the more the solubility in a resist solvent is improved.

Further, in the alkylene group for X" or the alkyl group for Y" and Z", it is preferable that the number of hydrogen atoms substituted with fluorine atoms is as large as possible, because the acid strength increases and the transparency to high energy radiation of 200 nm or less or an electron beam is improved. The amount of fluorine atoms within the alkylene group or alkyl group, namely the fluorination ratio, is preferably from 70 to 100% and more preferably from 90 to 100%, and it is particularly desirable that the alkylene group or alkyl group is a perfluoroalkylene or perfluoroalkyl group in which all the hydrogen atoms are substituted with fluorine atoms.

Furthermore, as the onium salt-based acid generator, a sulfonium salt having a cation moiety represented by general formula (b-5) or (b-6) shown below may also be used.

[Chemical Formula 55]

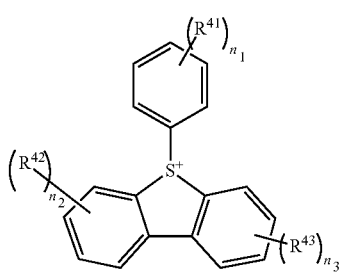

(b-5)

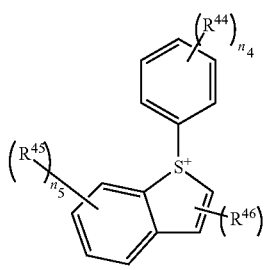

(b-6)

wherein $R^{41}$ to $R^{46}$ each independently represents an alkyl group, acetyl group, alkoxy group, carboxyl group, hydroxyl group or hydroxyalkyl group; $n_1$ to $n_5$ each independently represents an integer of 0 to 3; and $n_6$ represents an integer of 0 to 2.

The alkyl group for $R^{41}$ to $R^{46}$ is preferably an alkyl group having 1 to 5 carbon atoms, is more preferably a linear or branched alkyl group, and is most preferably a methyl group, ethyl group, propyl group, isopropyl group, n-butyl group or tert-butyl group.

The alkoxy group for $R^{41}$ to $R^{46}$ is preferably an alkoxy group having 1 to 5 carbon atoms, is more preferably a linear or branched alkoxy group, and is most preferably a methoxy group or ethoxy group.

The hydroxyalkyl group for $R^{41}$ to $R^{46}$ is preferably a group in which one or more hydrogen atoms within an aforementioned alkyl group have been substituted with hydroxyl groups, and is most preferably a hydroxymethyl group, hydroxyethyl group or hydroxypropyl group.

When the subscripts $n_1$ to $n_6$ of $R^{41}$ to $R^{46}$ represent an integer of 2 or more, the plurality of $R^{41}$ to $R^{46}$ groups may be the same or different.

$n_1$ is preferably 0 to 2, more preferably 0 or 1, and still more preferably 0.

It is preferable that $n_2$ and $n_3$ each independently represents 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties as those within onium salt-based acid generators that have previously been proposed may be used. Examples of such anion moieties include fluorinated alkylsulfonic acid ions, such as the anion moieties ($R^{4"'}SO_3$) within the onium salt-based acid generators represented by general formula (b-1) or (b-2) shown above; and anion moieties represented by general formula (b-3) or (b-4) shown above. Among these, fluorinated alkylsulfonic acid ions are preferable, fluorinated alkylsulfonic acid ions of 1 to 4 carbon atoms are more preferred, and linear perfluoroalkylsulfonic acid ions of 1 to 4 carbon atoms are particularly desirable. Specific examples include a trifluoromethylsulfonic acid ion, heptafluoro-n-propylsulfonic ion and nonafluoro-n-butylsulfonic acid ion.

In the present description, an oxime sulfonate-based acid generator is a compound having at least one group represented by general formula (B-1) shown below, and has a feature of generating acid upon irradiation. Such oxime sulfonate-based acid generators are widely used for chemically amplified resist compositions, and conventional compounds can be appropriately selected.

[Chemical Formula 56]

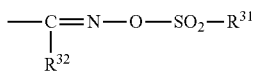

(B-1)

wherein $R^{31}$ and $R^{32}$ each independently represents an organic group.

The organic group for $R^{31}$ and $R^{32}$ refers to a group containing a carbon atom, and may include atoms other than carbon atoms (for example, a hydrogen atom, oxygen atom, nitrogen atom, sulfur atom, or a halogen atom (such as a fluorine atom or chlorine atom) or the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched or cyclic alkyl group having 1 to 6 carbon atoms. The expression "have a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereafter sometimes referred to as a "halogenated alkyl group") is particularly desirable. A "partially halogenated alkyl group" refers to an alkyl group in which some of the hydrogen atoms are substituted with halogen atoms, and a "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. A "partially halogenated aryl group" refers to an aryl group in which some of the hydrogen atoms are substituted with halogen atoms, and a "completely halogenated aryl group" refers to an aryl group in which all of hydrogen atoms are substituted with halogen atoms.

As $R^{31}$, an alkyl group of 1 to 4 carbon atoms that has no substituent or a fluorinated alkyl group of 1 to 4 carbon atoms is particularly desirable.

As the organic group for $R^{32}$, a linear, branched or cyclic alkyl group or aryl group, or a cyano group is preferred. Examples of the alkyl group and aryl group for $R^{32}$ include the same groups as those exemplified above for the alkyl group and aryl group for $R^{31}$.

As $R^{32}$, a cyano group, an alkyl group of 1 to 8 carbon atoms having no substituent, or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 57]

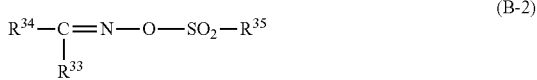

(B-2)

wherein $R^{33}$ represents a cyano group, an alkyl group having no substituent, or a halogenated alkyl group; $R^{34}$ represents an aryl group; and $R^{35}$ represents an alkyl group having no substituent, or a halogenated alkyl group.

[Chemical Formula 58]

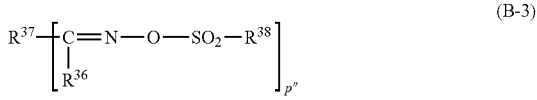

(B-3)

wherein $R^{36}$ represents a cyano group, an alkyl group having no substituent, or a halogenated alkyl group; $R^{37}$ represents a divalent or trivalent aromatic hydrocarbon group; $R^{38}$ represents an alkyl group having no substituent, or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferred, and a fluorinated alkyl group is more preferable.

The fluorinated alkyl group for $R^{33}$ preferably has 50% or more of the hydrogen atoms of the alkyl group fluorinated, more preferably 70% or more fluorinated, and most preferably 90% or more fluorinated.

Examples of the aryl group for $R^{34}$ include groups in which one hydrogen atom has been removed from an aromatic hydrocarbon ring, such as a phenyl group, biphenyl group, fluorenyl group, naphthyl group, anthryl group and phenanthryl group, and heteroaryl groups in which some of the carbon atoms constituting the ring(s) of these groups are substituted with hetero atoms such as an oxygen atom, a sulfur atom or a nitrogen atom. Of these, a fluorenyl group is preferable.

The aryl group for $R^{34}$ may have a substituent such as an alkyl group, halogenated alkyl group or alkoxy group of 1 to 10 carbon atoms. The alkyl group or halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferred, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more flourinated, still more preferably 90% or more flourinated. A completely flourinated alkyl group in which 100% of the hydrogen atoms are substituted with fluorine atoms is particularly desirable.

In genaral formula (B-3), the alkyl group having no substituent and the halogenated alkyl group for $R^{36}$ are the same as the alkyl group having no substituent and the halogenated alkyl group described for $R^{33}$ in general formula (B-2).

Examples of the divalent or trivalent aromatic hydrocarbon group for $R^{37}$ include groups in which one or two hydrogen atoms have been removed from the aryl group for $R^{34}$ in general formula (B-2).

Examples of the alkyl group having no substituent or the halogenated alkyl group for $R^{38}$ include the same groups as those exemplified above for the alkyl group having no substituent or the halogenated alkyl group for $R^{35}$ in general formula (B-2).

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(chlorobenzenesulfonyloxyimino)-4methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsfoylfonyloxyimio)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may also be used favorably.

Furthermore, preferred examples include the compounds shown below.

[Chemical Formula 59]

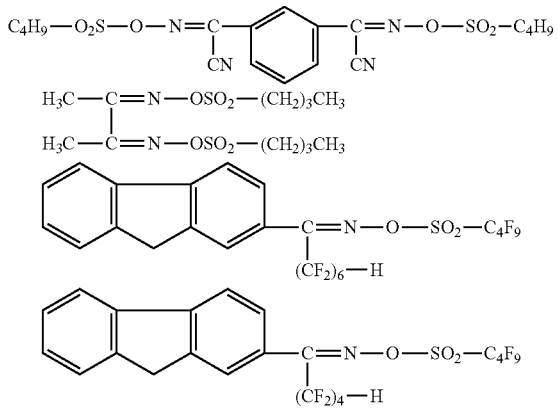

Of the aforementioned diazomethane-based acid generators, specific examples of bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenyl sulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be exemplified.

As the component (B2), one type of acid generator may be used alone, or two or more types may be used in combination. Of the various possibilities, it is preferable to use an onium salt-based acid generator having a fluorinated alkylsulfonic acid ion as the anion moiety.

The total amount of the component (B) within the resist composition of the present invention is typically 0.5 to 30 parts by weight, and preferably 1 to 10 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>

In the resist composition of the present invention, in order to improve the resist pattern shape and the post exposure stability of the latent image formed by the pattern-wise exposure of the resist layer, a nitrogen-containing organic compound (D) (hereafter referred to as "component (D)") may be added as an optional component.

A multitude of these components (D) have already been proposed, and any of these known compounds may be used, although an aliphatic amine, and particularly a secondary aliphatic amine or tertiary aliphatic amine is preferable. An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (namely, alkylamines or alkyl alcohol amines), and cyclic amines.

Specific examples of alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines in which the alkyl groups have 5 to 10 carbon atoms are preferable, and tri-n-pentylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

These compounds may be used either alone, or in combinations of two or more different compounds.

The component (D) is typically used in an amount within a range from 0.01 to 5.0 parts by weight, relative to 100 parts by weight of the component (A).

Furthermore, in the resist composition of the present invention, in order to prevent any deterioration in sensitivity, and improve the resist pattern shape and the post exposure stability of the latent image formed by the pattern-wise exposure of the resist layer, at least one compound (E) (hereafter referred to as "component (E)") selected from the group consisting of organic carboxylic acids, and phosphorus oxo acids and derivatives thereof may be added.

Examples of the organic carboxylic acids include acetic acid, malonic acid, citric acid, malic acid, succinic acid, benzoic acid, and salicylic acid.

Examples of the phosphorus oxo acids include phosphoric acid, phosphonic acid and phosphinic acid. Among these, phosphonic acid is particularly desirable.

Examples of oxo acid derivatives include esters in which a hydrogen atom within an above-mentioned oxo acids is substituted with a hydrocarbon group. Examples of the hydrocarbon group include an alkyl group of 1 to 5 carbon atoms or an aryl group of 6 to carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type of compound may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Organic Solvent (S)>

The resist composition of the present invention can be prepared by dissolving the materials for the resist composition in an organic solvent (S) (hereafter, frequently referred to as "component (S)").

The component (S) may be any organic solvent which can dissolve the respective components to give a uniform solution, and any one or more types of organic solvent can be appropriately selected from those that have been conventionally known as solvents for chemically amplified resists.

Examples thereof include lactones such as γ-butyrolactone; ketones such as acetone, methyl ethyl ketone, cyclohexanone, methyl-n-pentyl ketone, methyl isopentyl ketone and 2-heptanone; polyhydric alcohols such as ethylene glycol, diethylene glycol, propylene glycol and dipropylene glycol; polyhydric alcohol derivatives, including compounds having an ester bond such as ethylene glycol monoacetate, diethylene glycol monoacetate, propylene glycol monoacetate and dipropylene glycol monoacetate, and compounds having an ether bond such as a monoalkyl ether (such as a monomethyl ether, monoethyl ether, monopropyl ether or monobutyl ether) or a monophenyl ether of any of the above polyhydric alcohols or compounds having an ester bond [among these derivatives, propylene glycol monomethyl ether acetate (PGMEA) and propylene glycol monomethyl ether (PGME) are preferred]; cyclic ethers such as dioxane; esters such as methyl lactate, ethyl lactate (EL), methyl acetate, ethyl acetate, butyl acetate, methyl pyruvate, ethyl pyruvate, methyl methoxypropionate and ethyl ethoxypropionate; and aromatic organic solvents such as anisole, ethyl benzyl ether, cresyl methyl ether, diphenyl ether, dibenzyl ether, phenetol, butyl phenyl ether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME), and ethyl lactate (EL) are preferable.

Further, among the mixed solvents, a mixed solvent obtained by mixing PGMEA with a polar solvent is preferable. The mixing ratio (weight ratio) of the mixed solvent can be determined appropriately with due consideration of the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the organic solvent is not particularly limited, and may be adjusted appropriately to a concentration that enables coating of a coating solution to a substrate in accordance with the thickness of the coating film. In general, the organic solvent is used in an amount that yields a solid content for the resist composition that is within a range from 2 to 20% by weight, and preferably from 5 to 15% by weight.

<<Method of Forming a Resist Pattern>>

The method of forming a resist pattern according to the present invention includes: forming a resist film on a substrate using the resist composition according to the present invention described above, conducting exposure of the resist film, and alkali developing the resist film to form a resist pattern.

More specifically, the method of forming a resist pattern according to the present invention can be performed, for example, as follows. Firstly, a resist composition of the present invention is applied onto a substrate using a spinner or the like, and a prebake (post applied bake (PAB)) is conducted under temperature conditions of 80 to 150° C. for 40 to 120 seconds, and preferably 60 to 90 seconds, to form a resist film. Then, for example, using an ArF exposure apparatus or the like, the resist film is selectively exposed to an ArF excimer laser beam through a desired mask pattern, and then subjected to a post exposure bake (PEB) under temperature conditions of 80 to 150° C. for 40 to 120 seconds, and preferably 60 to 90 seconds. Subsequently, developing is conducted using an alkali developing solution such as a 0.1 to 10% by weight aqueous solution of tetramethylammonium hydroxide (TMAH), preferably followed by rinsing with pure water, and drying. If desired, a bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be exemplified. Specific examples of the material of the substrate include metals such as silicon wafer, copper, chromium, iron and aluminum; and glass. Suitable materials for the wiring pattern include copper, aluminum, nickel and gold.

Further, as the substrate, any one of the above-exemplified substrates provided with an inorganic and/or organic film on the surface thereof may also be used. As the inorganic film, an inorganic anti-reflection film (inorganic BARC) can be exemplified. As the organic film, an organic anti-reflection film (organic BARC) can be exemplified.

The wavelength to be used for exposure is not particularly limited and the exposure can be conducted using radiation such as an ArF excimer laser, KrF excimer laser, $F_2$ excimer laser, extreme ultraviolet rays (EUV), vacuum ultraviolet rays (VUV), electron beam (EB), X-rays, and soft X-rays. The positive resist composition of the present invention is effective for use with a KrF excimer laser, ArF excimer laser, EB and EUV, and is particularly effective for use with a ArF excimer laser.

The exposure of the resist film may be either a general exposure (dry exposure) conducted in air or an inert gas such as nitrogen, or immersion exposure (immersion lithography).

In immersion lithography, exposure (immersion exposure) is conducted in a state where the region between the lens and the resist film formed on a wafer (which is conventionally filled with air or an inert gas such as nitrogen) is filled with a solvent (an immersion medium) that has a larger refractive index than the refractive index of air.

More specifically, in immersion lithography, the region between the resist film formed in the above-described manner and the lens at the lowermost portion of the exposure apparatus is filled with a solvent (an immersion medium) that has a larger refractive index than the refractive index of air, and in this state, the resist film is subjected to exposure (immersion exposure) through a desired mask pattern.

The immersion medium preferably exhibits a refractive index that is larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C., and preferably from 80 to 160° C. A fluorine-based inert liquid having a boiling point within the above-mentioned range is advantageous in that the removal of the immersion medium after the exposure can be conducted by a simple method.

As the fluorine-based inert liquid, a perfluoroalkyl compound in which all of the hydrogen atoms of the alkyl group are substituted with fluorine atoms is particularly desirable. Examples of such perfluoroalkyl compounds include perfluoroalkyl ether compounds and perfluoroalkylamine compounds.

Specifically, one example of a suitable perfluoroalkyl ether compound is perfluoro(2-butyl-tetrahydrofuran) (boiling point 102° C.), and an example of a suitable perfluoroalkylamine compound is perfluorotributylamine (boiling point 174° C.).

The resist composition of the present invention is a novel composition that has been unknown until now.

By using the resist composition of the present invention, the mask reproducibility (for example, the mask linearity) obtained upon formation of a resist pattern improves, and a resist pattern having superior lithography properties (such as superior circularity of the holes of a contact hole pattern) can be formed. The reason for these observations is not entirely clear yet, but is presumed as follows.

In the resist composition of the present invention, the aforementioned component (B1) is used as an acid generator.

The anion moiety of the component (B1) includes a ring structure, and is a bulky structure that exhibits considerable steric hindrance. On this ring structure is included not only an anion moiety-containing group, but also another ester linkage-containing group, and the carbon atom that constitutes part of the ester linkage is bonded directly to the ring structure. In other words, the anion moiety of the component (B1) has highly polar groups both on the ring structure and in the close vicinity of the ring structure. Accordingly, as a result of the fact that the anion moiety of the component (B1) has a three-dimensionally bulky structure compared with the anion moiety of conventional acid generators such as a nonafluorobutanesulfonate anion, and also as a result of the intermolecular forces generated by the high polarity, it is presumed that diffusion of the anion moiety within the resist film is suppressed both chemically and physically. Therefore, by using the component (B31), diffusion of the acid generated in the exposed regions to the unexposed regions can be suppressed, and hence, the difference in alkali solubility between the exposed regions and the unexposed regions (namely, the solubility contrast) can be improved, and it is presumed that this results in an improvement in the resist pattern shape.

Further, for the same reasons as described above, an improvement in the exposure margin (EL margin) is also expected. The EL margin is the exposure dose range over which a resist pattern can be formed with a size that falls within a predetermined range of variation from a target size, when exposure is conducted by changing the exposure dose, namely, the exposure dose range over which a resist pattern faithful to the mask pattern can be formed. The larger the EL margin, the smaller the variation in the pattern size that accompanies change in the exposure dose, thereby resulting in a favorable improvement in the process margin.

EXAMPLES

As follows is a description of examples of the present invention, although the scope of the present invention is in no way limited by these examples.

Synthesis Example 1

Synthesis of Compound (I-1-101)

(i) 150 g of methyl fluorosulfonyl(difluoro)acetate and 375 g of pure water were maintained at 10° C. or lower in an ice bath, and 343.6 g of a 30% aqueous solution of sodium hydroxide was added dropwise to the mixture. Following completion of the dropwise addition, the resulting mixture was refluxed at 100° C. for 3 hours, and was then cooled and neutralized with concentrated hydrochloric acid. The resulting solution was added dropwise to 8.888 g of acetone, and the resulting precipitate was collected by filtration and dried, thereby obtaining 184.5 g of a compound (I-1-101b) in the form of a white solid (purity: 88.9%, yield: 95.5%).

[Chemial Formula 60]

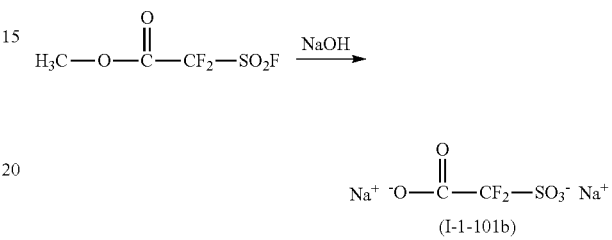

(ii) A flask was charged with 56.2 g of the compound (I-1-101b) and 562.2 g of acetonitrile, 77.4 g of p-toluenesulfonic acid monohydrate was added, and the resulting mixture was refluxed at 110° C. for 3 hours.

Subsequently, the reaction liquid was filtered, and the filtrate was concentrated and dried to obtain a solid. 900 g of t-butyl methyl ether was then added to the obtained solid and stirred. Thereafter, the resulting mixture was filtered, and the residue was dried, yielding 22.2 g of a compound (I-1-101) in the form of a white solid (purity: 91.0%, yield: 44.9%).

[Chemical Formula 61]

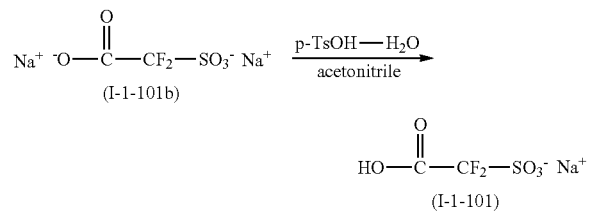

Example 1

Synthesis of Compound (I-101)

A flask was charged with 5.00 g of a compound represented by formula (I-10-201) shown below, 4.98 g of the compound (I-1-101) (purity: 94.1%) and 49.8 g of toluene, 0.55 g of p-toluenesulfonic acid monohydrate was then added, and the resulting mixture was refluxed at 130° C. for 26 hours. Subsequently, the reaction liquid was filtered, and 92.5 g of methyl ethyl ketone was added to the residue and stirred. Thereafter, the resulting mixture was filtered, and the filtrate was concentrated and dried, yielding 3.41 g of a compound (I-101) in the form of a brownish viscous solid (purity: 60.7%, yield: 22.4%).

[Chemical Formula 62]

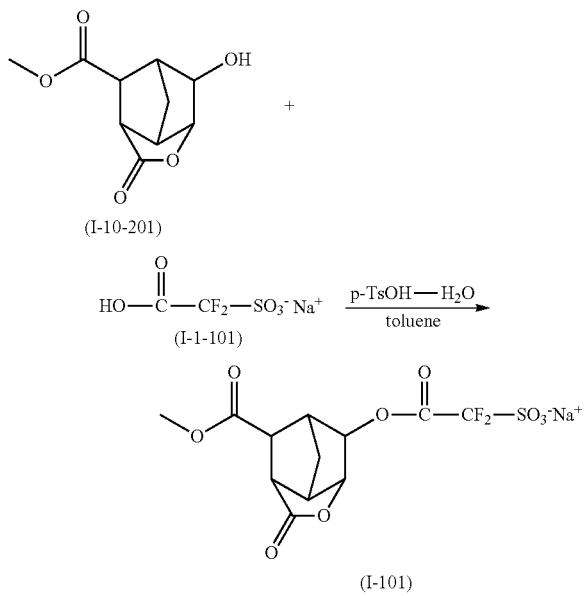

(I-10-201)

(I-1-101)

(I-101)

Example 2

Synthesis of Compound (b1-2-101)

2.0 g of the compound (I-101) (purity: 60.7%) was dissolved in 9.22 g of dichloromethane. To this solution was added a solution prepared by dissolving 0.92 g of 4-methylphenyldiphenylsulfonium bromide in 4.61 g of pure water, and following stirring of the resulting mixture for 3 hours at room temperature, the organic phase was separated and extracted. The organic phase was washed with a further 4.61 g of pure water, and the organic phase was then concentrated and dried, yielding 1.4 g of a compound (b1-2-101) in the form of a white solid (purity: 84.9%, yield: 71.1%).

[Chemical Formula 63]

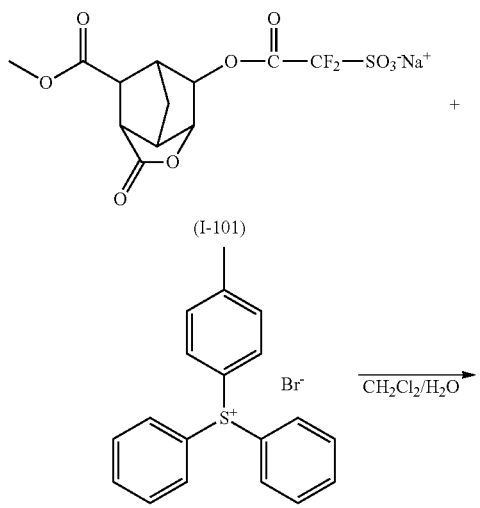

(I-101)

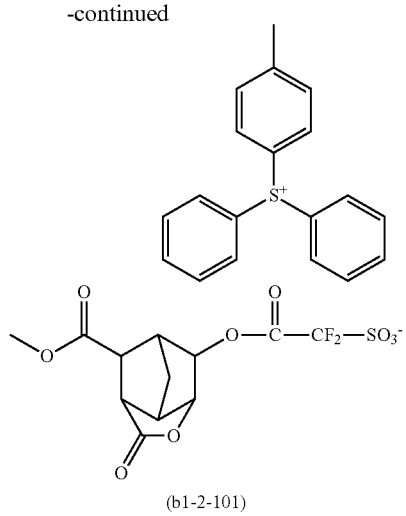

(b1-2-101)

The thus obtained compound (b1-2-101) was analyzed by NMR.

$^1$H-NMR (DMSO, 400 MHz): δ (ppm)=7.88 to 7.60 (m, 14H, H$^i$), 5.24 (t, 1H, H$^a$), 4.59 (m, 1H, H$^b$), 3.62 (m, 3H, H$^h$), 3.40 to 3.30 (m, 2H, H$^f$+H$^g$), 2.89 (m, 1H, H$^e$), 2.71 (t, 1H, H$^c$), 2.51 to 2.41 (m, 3H, H$^j$), 1.98, 1.71 (m, 2H, H$^d$).

$^{19}$F-NMR (DMSO, 376 MHz): δ (ppm)=−107.6 to −107.8

From the above results, it was confirmed that the compound (b1-2-101) had a structure shown below.

[Chemical Formula 64]

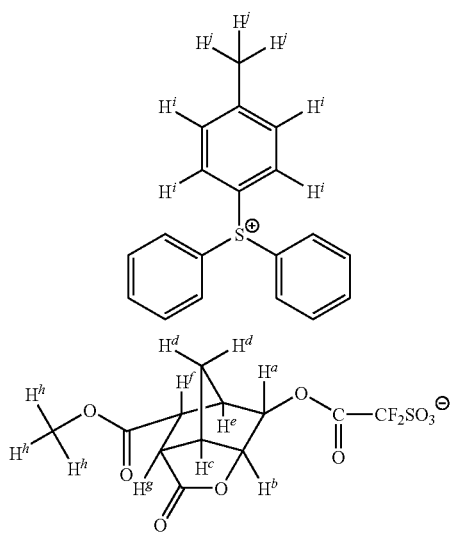

Reference Example 1

Synthesis of Compound (5)

A 1 liter three-necked flask was charged with 4.8 g of sodium hydride (NaH), and with the temperature maintained at 0° C. in an ice bath, 300 g of tetrahydrofuran (THF) was added. With the mixture undergoing constant stirring, 124 g of a compound (1) shown below was added, and the resulting mixture was stirred for a further 10 minutes. Subsequently, 30 g of a compound (2) shown below was added under constant stirring, and the mixture was then reacted for 12 hours. Following completion of the reaction, the reaction liquid was filtered by suction filtration, and the THF was removed from the recovered filtrate by concentration under reduced pressure. Subsequently, an extraction was performed by adding water and ethyl acetate to the concentrated liquid, and the extracted ethyl acetate solution was concentrated under reduced pressure and then purified using column chromatography (SiO$_2$, heptane:ethyl acetate=8:2). The isolated fraction was concentrated under reduced pressure and then dried under reduced pressure, yielding 12 g of a compound (3).

[Chemical Formula 65]

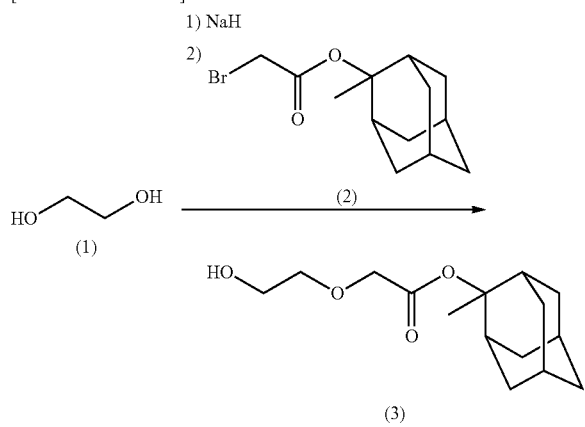

The thus obtained compound (3) was measured by $^1$H-NMR. The results are shown below.

$^1$H-NMR (solvent: CDCl$_3$, 400 MHz): δ (ppm)=4.09 (s, 2H($H^a$)), 3.75 (t, 2H ($H^b$)), 3.68 (t, 2H ($H^c$)), 3.03 (brs, 2H ($H^d$)), 1.51 to 2.35 (m, 17H ($H^e$)).

From the above results, it was confirmed that the compound (3) had a structure shown below.

[Chemical Formula 66]

Next, a 300 ml three-necked flask was charged with 5 g of the compound (3), 3.04 g of triethylamine (Et$_3$ N) and 10 g of THF were added, and the resulting mixture was stirred for 10 minutes. Subsequently, 2.09 g of a compound (4) shown below and 10 g of THF were added, and the resulting mixture was reacted for 12 hours at room temperature. Following completion of the reaction, the reaction liquid was filtered by suction filtration, and the THF was removed from the recovered filtrate by concentration under reduced pressure. Subsequently, an extraction was performed by adding water and ethyl acetate to the concentrated liquid. The thus obtained ethyl acetate solution was purified using column chromatography (SiO$_2$, heptane:ethyl acetate=8:2), and the isolated fraction was concentrated under reduced pressure and then dried under reduced pressure, yielding 4.9 g of a compound (5).

[Chemical Formula 67]

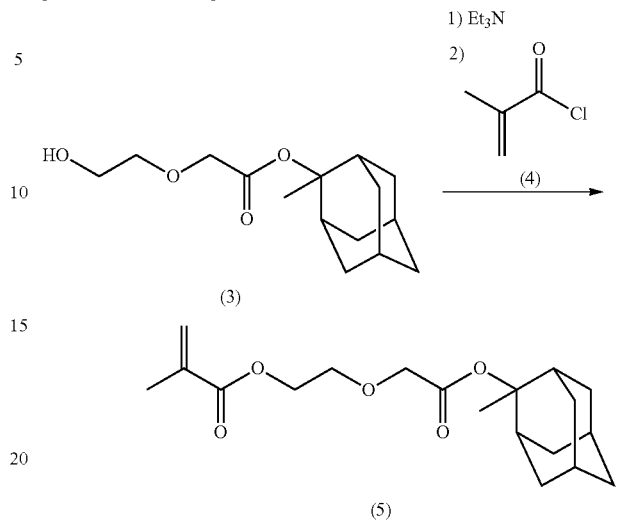

The thus obtained compound (5) was measured by $^1$H-NMR. The results are shown below.

$^1$H-NMR (solvent: CDCl$_3$, 400 MHz): δ (ppm)=6.15 (s, 1H ($H^a$)), 5.58 (s, 1H ($H^b$)), 4.35 (t, 2H ($H^c$)), 4.08 (s, 2H ($H^d$)), 3.80 (t, 2H ($H^e$)), 1.51 to 2.35 (m, 20H ($H^f$)).

From the above results, it was confirmed that the compound (5) had a structure shown below.

[Chemical Formula 68]

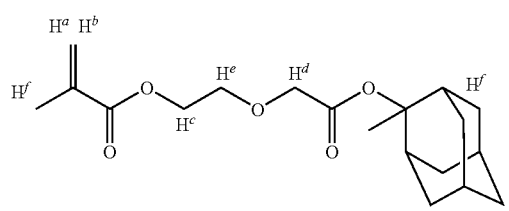

Reference Example 2

Synthesis of Polymer Compound (A)-1

[Chemical Formula 69]

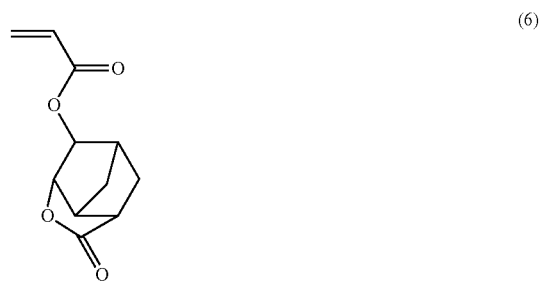

-continued (5)

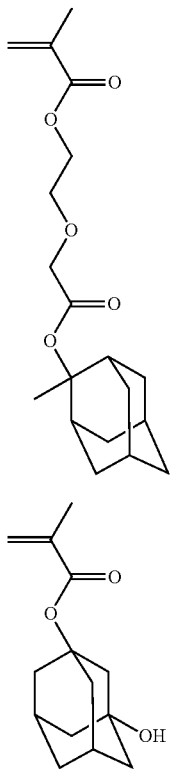

(7)

6.19 g (29.76 mmol) of a compound (6), 10.00 g (29.76 mmol) of the above-mentioned compound (5), and 3.51 g (14.88 mmol) of a compound (7) were dissolved in 78.80 g of methyl ethyl ketone. To this solution was added and dissolved 13.39 mmol of V-601 (a polymerization initiator, manufactured by Wako Pure Chemical Industries, Ltd.). The resulting solution was then added dropwise, over a 6 hour period and under a nitrogen atmosphere, to 32.83 g of methyl ethyl ketone heated at 75° C. Following completion of the dropwise addition, the reaction solution was stirred for a further one hour under heat, and the reaction solution was then cooled to room temperature.

The polymer solution was concentrated down to a solid fraction of 30% by weight, and was then added dropwise to 370 ml of n-heptane at room temperature, thereby precipitating a copolymer. Subsequently, 66 g of a THF solution of this copolymer was prepared, and the resulting solution was once again added dropwise to 370 ml of n-heptane to re-precipitate the copolymer.

A washing operation was performed by dispersing the resulting copolymer in a mixed solution of methanol/water=60/40 (volumetric ratio), an additional washing operation was performed by dispersing the copolymer in a mixed solution of methanol/water=70/30 (volumetric ratio), and the copolymer was then recovered by filtration.

The thus obtained copolymer was dried at 40° C. for 3 days, yielding 14.9 g of a white powder (yield: 76%).

The thus obtained copolymer was termed "polymer compound (A)-1", and the structure of the copolymer is shown below. Analysis of this polymer compound (A)-1 using carbon-13 nuclear magnetic resonance spectrometry (600 MHz $^{13}$C-NMR) revealed a polymer composition (the proportion (molar ratio) of each of the structural units in the structural formula shown below) of l/m/n=42.4/37.2/19.9. Furthermore, the polystyrene equivalent weight average molecular weight determined by GPC measurement was 6,400, and the dispersity was 1.80. These results confirmed that the obtained polymer compound (A)-1 was a copolymer of the compound (6), the compound (5) and the compound (7).

[Chemical Formula 70]

Polymer compound (A)-1

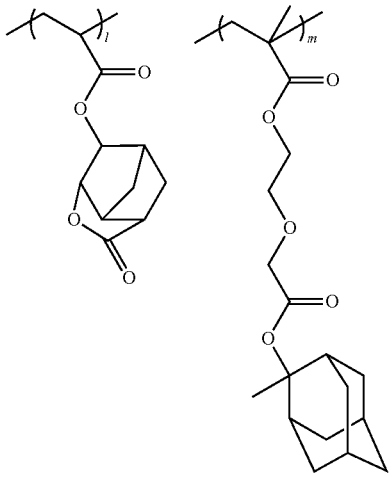

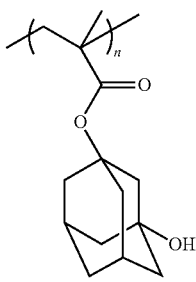

Example 1

Comparative Example 1

The components shown in Table 1 were mixed together and dissolved in the amounts shown to obtain positive resist composition solutions.

TABLE 1

|  | (A) | (B) | (S) |
| --- | --- | --- | --- |
| Example 1 | (A)-1 | (B)-1 | (S)-1 |
|  | [100] | [5.24] | [2200] |
| Comparative example 1 | (A)-1 | (B)-2 | (S)-1 |
|  | [100] | [4.67] | [2200] |

The meanings of the abbreviations used in Table 1 are as shown below. Further, the values in brackets [ ] indicate the amount (in terms of parts by weight) of the component. The amount of the component (B)-1 in example 1 is equimolar with the amount of the component (B)-2 in comparative example 1.

(A)-1: the polymer compound (A)-1 of reference example 2.

(B)-1: the acid generator represented by chemical formula (b1-2-101) above.

(B)-2: 4-methylphenyldiphenylsulfonium nonafluoro-n-butanesulfonate (S)-1: a mixed solvent of PGMEA/PGME=6/4 (weight ratio)

<Evaluation of Lithography Properties>

Resist patterns were formed using the prepared positive resist composition solutions, and the lithography properties described below were evaluated.

[Resolution•Sensitivity]

An organic anti-reflection film composition (product name: ARC29, manufactured by Brewer Science Ltd.) was applied onto an 8-inch silicon wafer using a spinner, and the composition was then baked on a hotplate at 205° C. for 60 seconds and dried, thereby forming an organic anti-reflection film having a film thickness of 82 nm. Subsequently, a positive resist composition of example 1 or comparative example 1 was applied onto the anti-reflection film using a spinner, and was then prebaked (PAB) on a hotplate at 90° C. for 60 seconds and dried, thereby forming a resist film having a film thickness of 120 nm.

Thereafter, using an ArF exposure apparatus (product name: NSR-S302, manufactured by Nikon Corporation, NA (numerical aperture)=0.60, ⅔ annular illumination), the resist film was selectively irradiated with an ArF excimer laser (193 nm) through a mask pattern (6% half-tone).

Subsequently, a post exposure bake (PEB) treatment was conducted at 90° C. for 60 seconds, followed by alkali development for 30 seconds at 23° C. in a 2.38% by weight aqueous solution of tetramethylammonium hydroxide (TMAH) (product name: NMD-3; manufactured by Tokyo Ohka Kogyo Co., Ltd.). The resist film was then rinsed for 30 seconds with pure water, and shaken dry.

As a result, in each of the examples, a contact hole pattern having holes of diameter 130 nm arranged at an equidistant spacing (pitch: 260 nm) was formed on the resist film.

For each example, the optimum exposure dose (sensitivity: Eop, mJ/cm$^2$) with which a contact hole pattern having a hole diameter of 130 nm and a pitch of 260 nm was formed was determined. The results are shown in Table 2.

[Circularity]

The contact hole pattern having a hole diameter of 130 nm and a pitch of 260 mm formed in the manner described above was inspected from directly above the pattern using a scanning electron microscope, and the circularity of the hole pattern was evaluated using the following criteria. The results of the evaluation are shown in Table 2.

A: extremely high circularity (observation of the hole pattern from directly above the pattern revealed an extremely favorable shape with no unevenness within the circular portions of the pattern).

B: observation of the hole pattern from directly above the pattern revealed slight unevenness within the circular portions of the pattern.

TABLE 2

|  | Eop (mJ/cm$^2$) | Circularity |
|---|---|---|
| Example 1 | 12.2 | A |
| Comparative example 1 | 5.8 | B |

The above results confirmed that the resist composition of example 1 according to the present invention exhibited excellent lithography properties.

The present invention is able to provide a novel compound that is useful as an acid generator for a resist composition, a compound that is useful as a precursor to the novel compound and a method of producing the same, an acid generator, a resist composition and a method of forming a resist pattern, and the invention is therefore extremely useful industrially.

What is claimed is:

1. A resist composition comprising a base component (A) that exhibits changed solubility in an alkali developing solution under action of acid, and an acid generator component (B) that generates acid upon exposure, wherein said acid generator component (B) comprises an acid generator (B1) consisting of a compound represented by general formula (b1-2) shown below:

$$A^+Z^- \quad (b1-2)$$

wherein A$^+$ represents an organic cation; and Z$^-$ represents an anionic cyclic group, wherein said cyclic group comprises an ester linkage within a ring structure thereof, two mutually different groups are bonded to said ring structure; one of said groups comprises an ester linkage in which a carbon atom that constitutes part of said ester linkage is bonded directly to said ring structure; and another of said groups comprises an anion moiety having an ester linkage in which the carbon atom that constitutes part of said ester linkage is not directly bonded to said ring structure.

2. A resist composition according to claim 1, wherein said compound represented by said general formula (b1-2) is represented by general formula (b1-2-1) shown below:

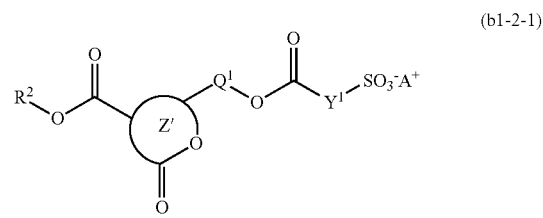

(b1-2-1)

wherein A$^+$ represents an organic cation, ring Z' represents a cyclic group of 3 to 20 carbon atoms that may have a substituent, R$^2$ represents an alkyl group that may have a substituent, Q$^1$ represents an alkylene group of 1 to 12 carbon atoms or a single bond, and Y$^1$ represents an alkylene group or fluorinated alkylene group of 1 to 4 carbon atoms.

3. A resist composition according to claim 2, wherein said compound represented by said general formula (b1-2-1) is represented by general formula (b1-2-10) shown below:

(b1-2-10)

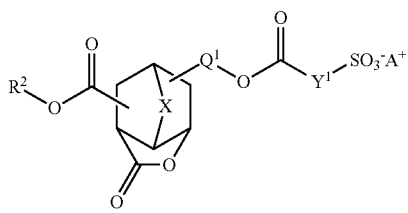

wherein A⁺ represents an organic cation; X represents an alkylene group, —O—, —S—, —O—R⁷—or —S—R⁸—, wherein R⁷ and R⁸ each independently represents an alkylene group of 1 to 5 carbon atoms; R² represents an alkyl group that may have a substituent; Q¹ represents an alkylene group of 1 to 12 carbon atoms or a single bond; and Y¹ represents an alkylene group or fluorinated alkylene group of 1 to 4 carbon atoms.

4. A resist composition according to claim 1, wherein said base component (A) exhibits increased solubility in an alkali developing solution under action of acid.

5. A resist composition according to claim 4, wherein said base component (A) comprises a resin component (A1) that exhibits increased solubility in an alkali developing solution under action of acid, and said resin component (A1) comprises a structural unit (a1) derived from an acrylate ester containing an acid-dissociable, dissolution-inhibiting group.

6. A resist composition according to claim 5, wherein said resin component (A1) further comprises a structural unit (a2) derived from an acrylate ester that contains a lactone-containing cyclic group.

7. A resist composition according to claim 5, wherein said resin component (A1) further comprises a structural unit (a3) derived from an acrylate ester that contains a polar group-containing aliphatic hydrocarbon group.

8. The resist composition according to claim 1, further comprising a nitrogen-containing organic compound (D).

9. A compound represented by general formula (b1-2) shown below:

A⁺Z⁻ (b1-2)

wherein A⁺ represents an organic cation; and Z⁻ represents an anionic cyclic group, wherein said cyclic group comprises an ester linkage within a ring structure thereof, two mutually different groups are bonded to said ring structure, one of said groups comprises an ester linkage in which a carbon atom that constitutes part of said ester linkage is bonded directly to said ring structure, and another of said groups comprises an anion moiety having an ester linkage in which the carbon atom that constitutes s art of said ester linkage is not directly bonded to said ring structure.

10. A compound according to claim 9, represented by general formula (b1-2-1) shown below:

(b1-2-1)

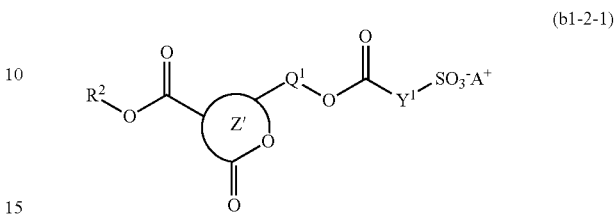

wherein A⁺ represents an organic cation, ring Z' represents a cyclic group of 3 to 20 carbon atoms that may have a substituent, R² represents an alkyl group that may have a substituent, Q¹ represents an alkylene group of 1 to 12 carbon atoms or a single bond, and Y¹ represents an alkylene group or fluorinated alkylene group of 1 to 4 carbon atoms.

11. A compound according to claim 10, represented by general formula (b1-2-10) shown below:

(b1-2-10)

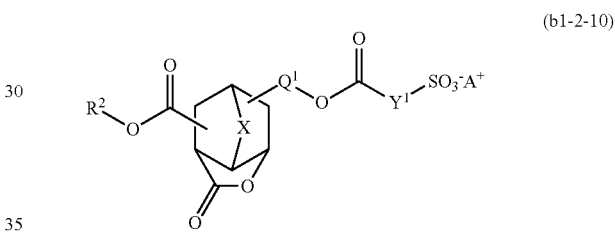

wherein A⁺ represents an organic cation; X represents an alkylene group, —O—, —S—, —O—R⁷—or —S—R⁸—, wherein R⁷ and R⁸ each independently represents an alkylene group of 1 to 5 carbon atoms; R² represents an alkyl group that may have a substituent; Q¹ represents an alkylene group of 1 to 12 carbon atoms or a single bond; and Y¹ represents an alkylene group or fluorinated alkylene group of 1 to 4 carbon atoms.

12. An acid generator consisting of a compound according to claim 9.

* * * * *

UNITED STATES PATENT AND TRADEMARK OFFICE
CERTIFICATE OF CORRECTION

PATENT NO. : 8,252,505 B2
APPLICATION NO. : 12/371876
DATED : August 28, 2012
INVENTOR(S) : Akiya Kawaue et al.

It is certified that error appears in the above-identified patent and that said Letters Patent is hereby corrected as shown below:

In Column 1, Line 29, Change "It" to --In--.

In Column 7, Line 7, Change "to" to --to 20--.

In Column 8, Line 63, Change "—CH(CH$_2$ CH$_3$) —," to -- —CH(CH$_2$CH$_3$) —,--.

In Column 14, Line 31, Change "—CF(CF$_3$)CF$_2$ CF$_2$—," to -- —CF(CF$_3$)CF$_2$CF$_2$—,--.

In Column 15, Line 35, Change "Z$^{01}$-(Z$^{01}$)'" to --Z$^{02}$-(Z$^{01}$)'--.

In Column 16, Line 38, Change "(ii) ')," to --(ii)").--.

In Column 16, Line 42 (Approx.), Change "(I-1-1-1a)" to --(I-1-1a)--.

In Column 17, Line 20, Change "(I-1-b)" to --(I-1-1b)--.

In Column 18, Lines 61-64, Delete "When a dehydrating............compound (I-1-2)." and insert the same below "used." on Col. 18, Line 62, as a new paragraph.

In Column 25, Line 30, Change "(I-1-235)" to --(I-10-235)--.

In Column 26, Line 2, Change "(I-1-239)" to --(I-10-239)--.

In Column 30, Line 22, Change "dimethyl)" to --dimethylphenyl)--.

In Column 34, Line 56, Change "nano-level" to --nano level--.

In Column 42, Lines 58-67,

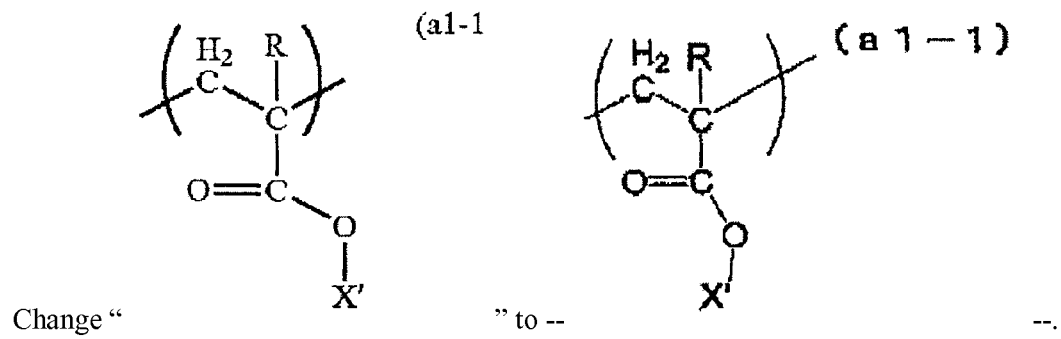

In Column 83, Line 15, Change "compatibility," to --compatibility--.

Signed and Sealed this
Nineteenth Day of February, 2013

Teresa Stanek Rea
*Acting Director of the United States Patent and Trademark Office*

In Column 83, Line 28, Change "below," to --below.--.

In Column 95, Line 21, Change "to" to --to 5--.

In Column 105, Line 40, Change "flourinated," to --fluorinated,--.

In Column 105, Line 41, Change "flourinated." to --fluorinated.--.

In Column 105, Line 41, Change "flourinated" to --fluorinated--.

In Column 105, Line 44, Change "genaral" to --general--.

In Column 106, Line 9, Change "(trifluoromethylsfoylfonyloxyimio)" to --(trifluoromethylsulfonyloxyimino)--.

In Column 106, Line 64, Change "dimethylphenyl sulfonyl)" to --dimethylphenylsulfonyl)--.

In Column 108, Line 31, Change "to" to --to 15--.

In Column 109, Line 17, Change "phenetol," to --phenetole,--.

In Column 111, Line 38, Change "(B31)," to --(B1),--.

In Column 115, Line 53, Change "(Et$_3$ N)" to --(Et$_3$N)--.

In Column 119, Line 19, Change "[Resolution•Sensitivity]" to --[Resolution Sensitivity]--.

In Column 120, Line 33, In Claim 1, change "A$^+$represents" to --A$^+$ represents--.

In Column 120, Line 33, In Claim 1, change "Z$^-$represents" to --Z$^-$ represents--.

In Column 120, Line 58, In Claim 2, change "A$^+$represents" to --A$^+$ represents--.

In Column 121, Line 43, In Claim 9, change "A$^+$represents" to --A$^+$ represents--.

In Column 121, Line 43, In Claim 9, change "Z$^-$represents" to --Z$^-$ represents--.

In Column 122, Line 2, In Claim 9, change "s art" to --part--.

In Column 122, Line 18, In Claim 10, change "A$^+$represents" to --A$^+$ represents--.